US011806364B2

(12) United States Patent
Shin et al.

(10) Patent No.: US 11,806,364 B2
(45) Date of Patent: Nov. 7, 2023

(54) METHOD FOR PRODUCING MYELOID-DERIVED SUPPRESSOR CELLS, MYELOID-DERIVED SUPPRESSOR CELLS PRODUCED THEREBY, AND METHODS THEREOF

(71) Applicants: Industry-Academic Cooperation Foundation, Yonsei University, Seoul (KR); Research & Business Foundation Sungkyunkwan University, Gyeonggi-do (KR)

(72) Inventors: Sung Jae Shin, Seoul (KR); Woo Sik Kim, Seoul (KR); Hong Min Kim, Seoul (KR); Kee Woong Kwon, Seoul (KR); Joo Heon Yoon, Seoul (KR); Won Jung Koh, Seoul (KR)

(73) Assignees: Industry-Academic Cooperation Foundation, Yonsei University, Seoul (KR); Research & Business Foundation Sungkyunkwan University, Gyeonggi-do (KR)

(*) Notice: Subject to any disclaimer, the term of this patent is extended or adjusted under 35 U.S.C. 154(b) by 622 days.

(21) Appl. No.: 16/652,349

(22) PCT Filed: Sep. 28, 2018

(86) PCT No.: PCT/KR2018/011558
§ 371 (c)(1),
(2) Date: Mar. 30, 2020

(87) PCT Pub. No.: WO2019/066571
PCT Pub. Date: Apr. 4, 2019

(65) Prior Publication Data
US 2020/0316117 A1    Oct. 8, 2020

(30) Foreign Application Priority Data

Sep. 28, 2017  (KR) .................. 10-2017-0125968
Sep. 28, 2017  (KR) .................. 10-2017-0125990
Sep. 28, 2017  (KR) .................. 10-2017-0126379

(51) Int. Cl.
*A61K 35/15*    (2015.01)
*C12N 5/077*    (2010.01)

(52) U.S. Cl.
CPC ............ *A61K 35/15* (2013.01); *C12N 5/0669* (2013.01); *C12N 2501/22* (2013.01); *C12N 2501/2306* (2013.01); *C12N 2501/24* (2013.01)

(58) Field of Classification Search
None
See application file for complete search history.

(56) References Cited

U.S. PATENT DOCUMENTS

| | | |
|---|---|---|
| 8,951,529 B2 | 2/2015 | Chen |
| 2007/0105800 A1 | 5/2007 | Agrawal et al. |
| 2008/0292648 A1 | 11/2008 | Kandimalla et al. |
| 2009/0041809 A1 | 2/2009 | Emtage |
| 2009/0053206 A1 | 2/2009 | Kandimalla et al. |
| 2010/0016250 A1 | 1/2010 | Nagata et al. |
| 2012/0082688 A1 | 4/2012 | Chen et al. |
| 2012/0294885 A1 | 11/2012 | David et al. |

FOREIGN PATENT DOCUMENTS

| | | |
|---|---|---|
| KR | 10-2003-0084826 A | 11/2003 |
| KR | 10-2015-0026301 A | 3/2015 |
| KR | 10-2015-0026301 A | 3/2015 |
| KR | 10-1546482 B1 | 8/2015 |
| KR | 10-2017-0010731 A | 2/2017 |
| KR | 10-2017-0031395 A | 3/2017 |
| KR | 10-1734697 B1 | 5/2017 |
| KR | 10-2017-0104694 A | 9/2017 |
| WO | WO-1998/018810 A1 | 5/1998 |
| WO | WO-2001/007055 A1 | 2/2001 |
| WO | WO-2003/035695 A2 | 5/2003 |
| WO | WO-2005/042018 A2 | 5/2005 |
| WO | WO-2007/084237 A2 | 7/2007 |
| WO | WO-2008/073959 A2 | 6/2008 |
| WO | WO-2008/131926 A1 | 11/2008 |
| WO | WO-2009/018431 A2 | 2/2009 |
| WO | WO-2010/088395 A2 | 8/2010 |
| WO | WO-2012/066335 A1 | 5/2012 |
| WO | WO-2012/066336 A1 | 5/2012 |
| WO | WO-2012/085291 A1 | 6/2012 |
| WO | WO-2015/168269 A1 | 11/2015 |
| WO | WO-2015/168279 A1 | 11/2015 |

OTHER PUBLICATIONS

Chaimin et al., J Clin Invest. 2010;120:457-71 (Year: 2010).*
Greifenberg et al., Eur J Immunol. 2009;39:2865-76 (Year: 2009).*
Sioud et al., J Mol Biol. Dec. 15, 2006;364(5):945-54 (Year: 2006).*
Buechler et al., J Immunol. Oct. 1, 2016;197(7):2577-82 (Year: 2016).*
Brinkmann et al., The interaction between the ER membrane protein UNC93B and TLR3, 7, and 9 is crucial for TLR signaling, *J. Cell. Biol.* 177:265-75 (2007).
De Weerd et al., Type I interferon receptors: biochemistry and biological functions, *J. Biol. Chem.* 282:20053-7 (2007).
Galluzzi et al., Trial Watch: Experimental Toll-like receptor agonists for cancer therapy, *Oncoimmunology.* 1:699-716 (2012).
Gibbard et al., Conserved features in the extracellular domain of human toll-like receptor 8 are essential for pH-dependent signaling, *J. Biol. Chem.* 281:27503-11 (2006).

(Continued)

*Primary Examiner* — Daniel C Gamett
(74) *Attorney, Agent, or Firm* — MARSHALL, GERSTEIN & BORUN LLP

(57) ABSTRACT

The present invention relates to a method for inducing differentiation of bone marrow cells into myeloid-derived suppressor cells (MDSCs) by treating the bone marrow cells with a toll-like receptor agonist (TLR agonist) or type I interferon, or for inducing dendritic cells from the MDSCs.

15 Claims, 41 Drawing Sheets

(56) References Cited

OTHER PUBLICATIONS

Hsu et al., Vaccination of patients with B-cell lymphoma using autologous antigen-pulsed dendritic cells, *Nat. Med.* 2:52-8 (1996).
Inaba et al., Dendritic cell progenitors phagocytose particulates, including bacillus Calmette-Guerin organisms, and sensitize mice to mycobacterial antigens in vivo, *J. Exp. Med.* 178:479-88 (1993).
Inaba et al., Dendritic cells as antigen presenting cells in vivo, *Int. Rev. Immunol.* 6:197-206 (1990).
International Search Report, PCT/KR2018/011558 (dated Mar. 29, 2019).
Kim et al., UNC93B1 delivers nucleotide-sensing toll-like receptors to endolysosomes, *Nature*. 452:234-8 (2008).
Korean Final Office Action, KR 10-2017-0125968, dated Jan. 4, 2019.
Korean Office Action, KR 10-2017-0125968, dated Sep. 7, 2018.
Korean Office Action, KR 10-2017-0126379, dated Aug. 30, 2018.
Korean Office Action, KR-10-2017-0125990, dated Sep. 7, 2018.
Krieg, Antitumor applications of stimulating toll-like receptor 9 with CpG oligodeoxynucleotides, *Curr. Oncol. Rep.* 6:88-95 (2004).
Krug et al., Identification of CpG oligonucleotide sequences with high induction of IFN-alpha/beta in plasmacytoid dendritic cells, *Eur. J. Immunol.* 31:2154-63 (2001).
Latz et al., TLR9 signals after translocating from the ER to CpG DNA in the lysosome, *Nat. Immunol.* 5:190-8 (2004).
Millrud et al., On the origin of myeloid-derived suppressor cells, *Oncotarget*. 8:3649-65 (2017).
Nishiya et al., TLR3 and TLR7 are targeted to the same intracellular compartments by distinct regulatory elements, *J. Biol. Chem.* 280:37107-17 (2005).
Park et al., Proteolytic cleavage in an endolysosomal compartment is required for activation of Toll-like receptor, *Nat. Immunol.* 9:1407-14 (2008).
Ranjith-Kumar et al., Biochemical and functional analyses of the human Toll-like receptor 3 ectodomain, *J. Biol. Chem.* 282:7668-78 (2007).
Smith et al., Antisense c-myc and immunostimulatory oligonucleotide inhibition of tumorigenesis in a murine B-cell lymphoma transplant model, *J. Natl. Cancer Inst.* 90:1146-54 (1998).
Tabeta et al., The Unc93b1 mutation 3d disrupts exogenous antigen presentation and signaling via Toll-like receptors 3, 7 and 9, *Nat. Immunol.* 7:156-64 (2006).
Taleb et al., Chronic Type I IFN Is Sufficient To Promote Immunosuppression through Accumulation of Myeloid-Derived Suppressor Cells, *J. Immunol.* 198:1156-63 (2017).
Weiner et al., Immunostimulatory oligodeoxynucleotides containing the CpG motif are effective as immune adjuvants in tumor antigen immunization, *Proc. Natl. Acad. Sci. USA*. 94:10833-7 (1997).
Xueqing et al., Toll-like receptor 9 signaling by CpG-B oligodeoxynucleotides induces an apoptotic pathway in human chronic lymphocytic leukemia B cells, *Blood*. 115:5041-52 (2010).
Youn et al., The biology of myeloid-derived suppressor cells: the blessing and the curse of morphological and functional heterogeneity, *Eur. J. Immunol.* 40:2969-75 (2010).
Greifenberg et al., "Myeloid-derived suppressor cell activation by combined LPS and IFN-y treatment impairs DC development", Eur. J. Immunol., 39:2865-2876 (2009).
Ray et al., "Immunosuppressive MDSCs inducted by TLR signaling during infection and role in resolution of inflammation", Frontiers in Cellular and Infection Microbiology, vol. 3, Article 52, pp. 1-8 (2013).
Sioud et al., "Signaling through Toll-like Receptor 7/8 Induces the Differentiation of Human Bone Marrow CD34+ Progenitor Cells Along the Myeloid Lineage", J. Mol. Biol., 364:945-954 (2006).
Talmadge et al., "History of myeloid-derived suppressor cells", Nature Review/Cancer, vol. 13, pp. 739-752 (2013).
Wang et al., "Effect of TLR Agonists on the Differentiation and Function of Human Monocytic Myeloid Derived Suppressor Cells", J. Immunol., 194(9):4215-4221 (2015).

\* cited by examiner

[FIG. 1]
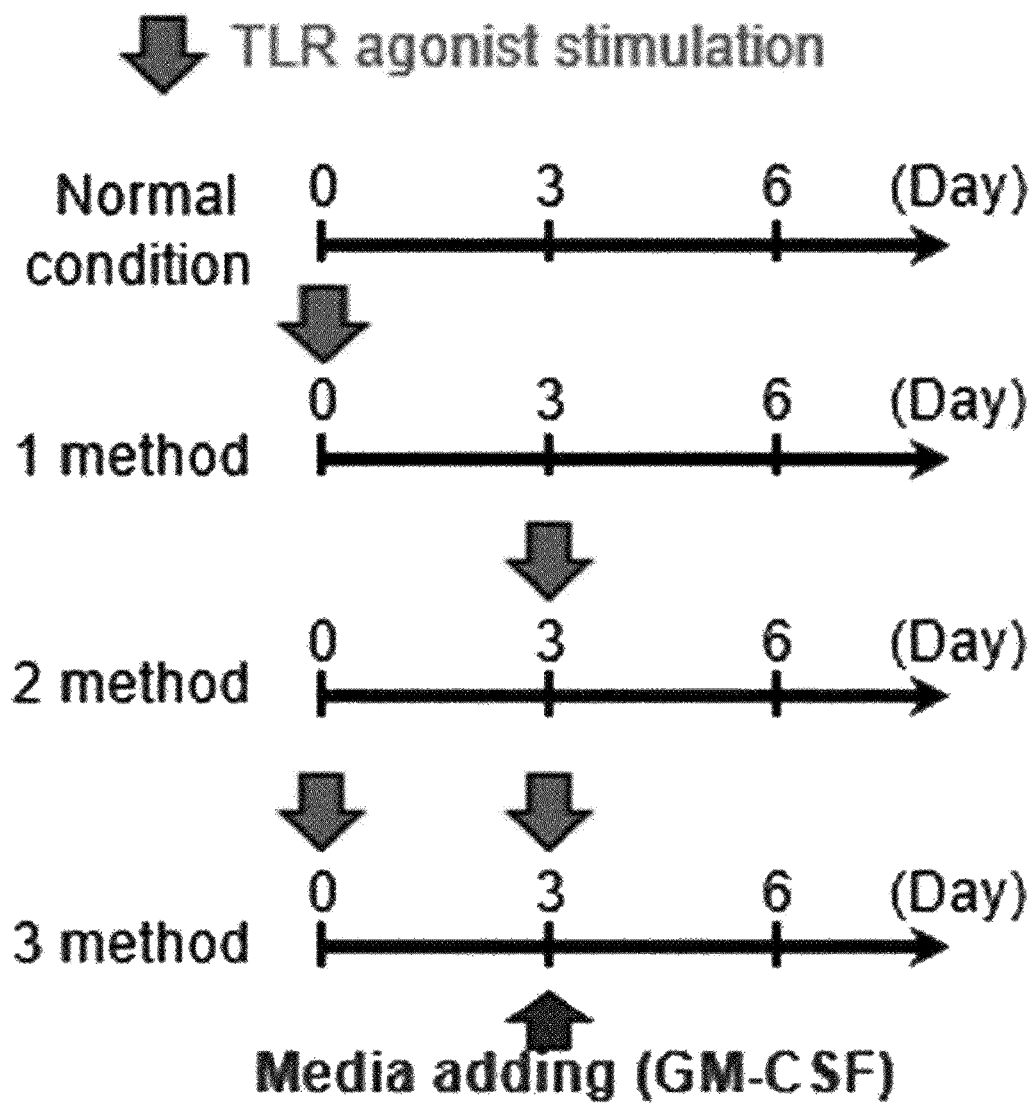

[FIG. 2]
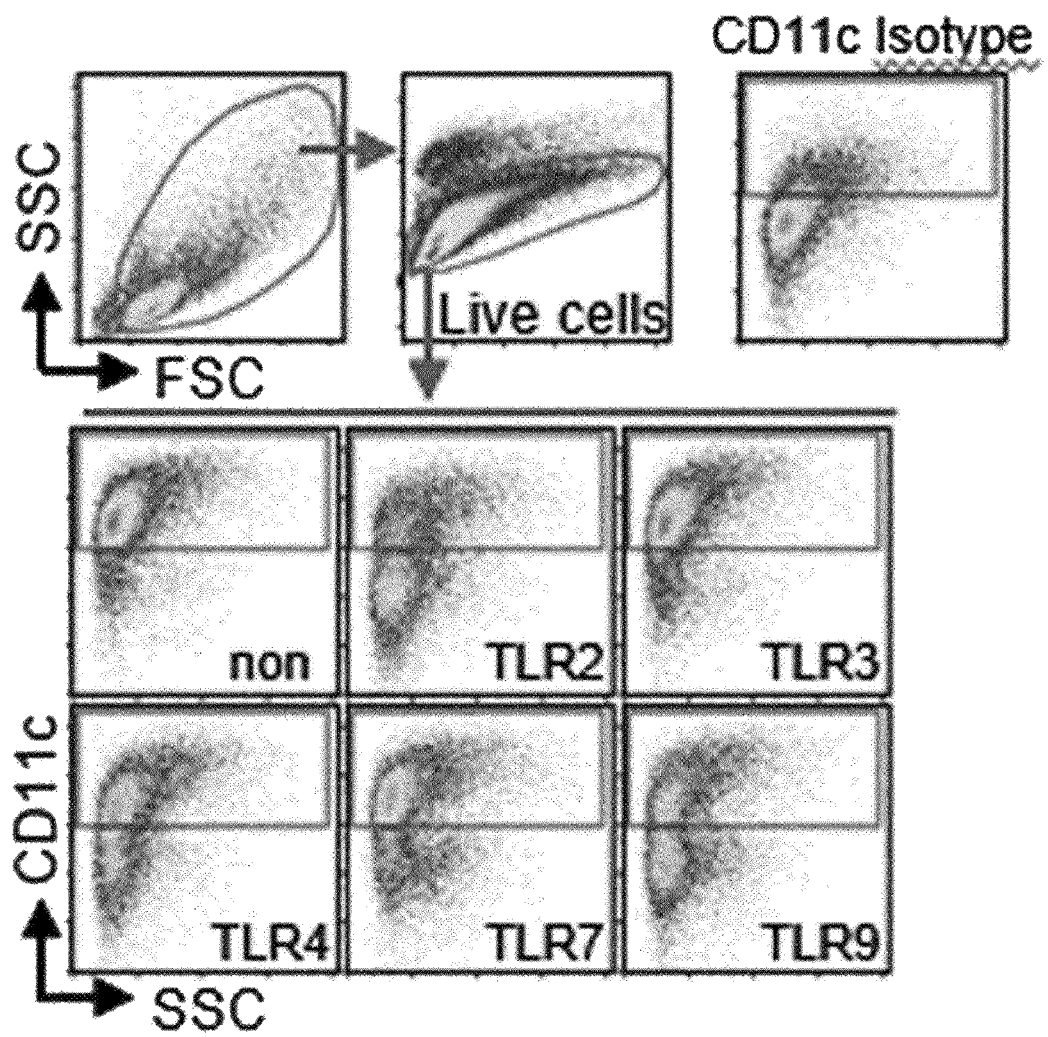

[FIG. 3]
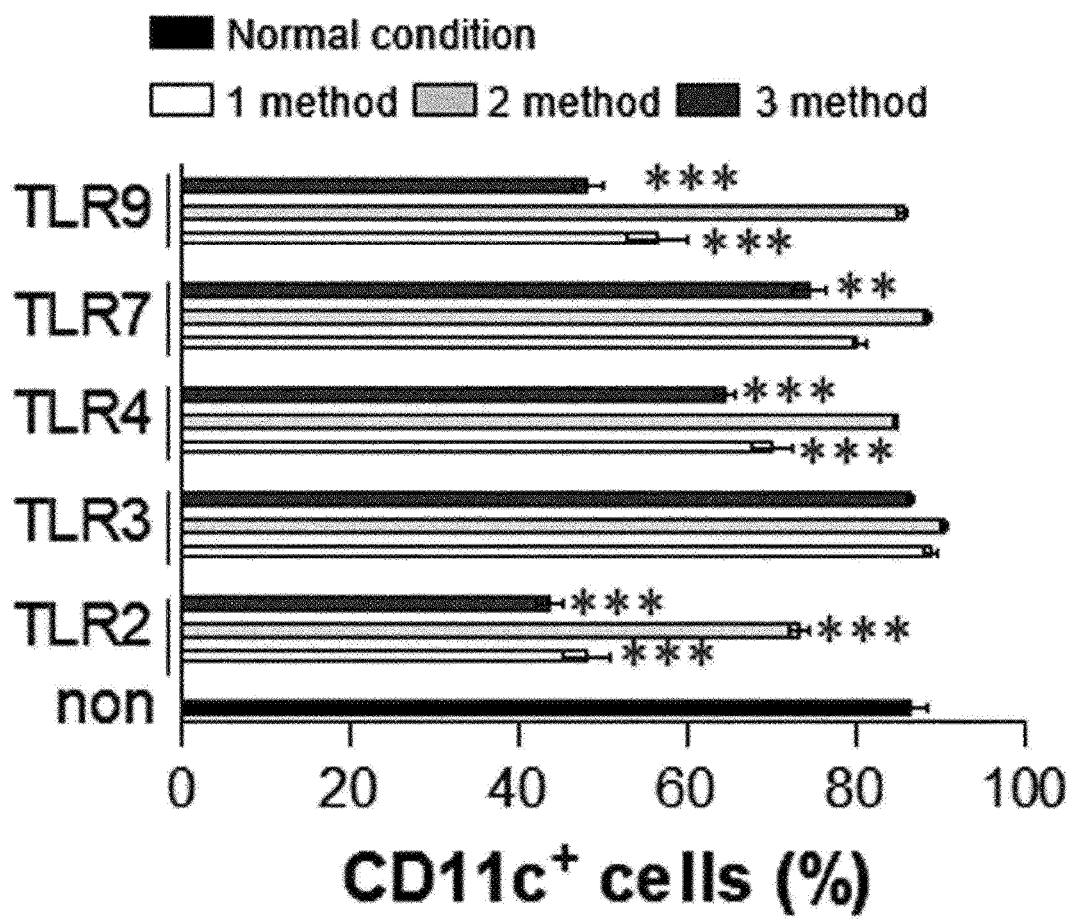

[FIG. 4]
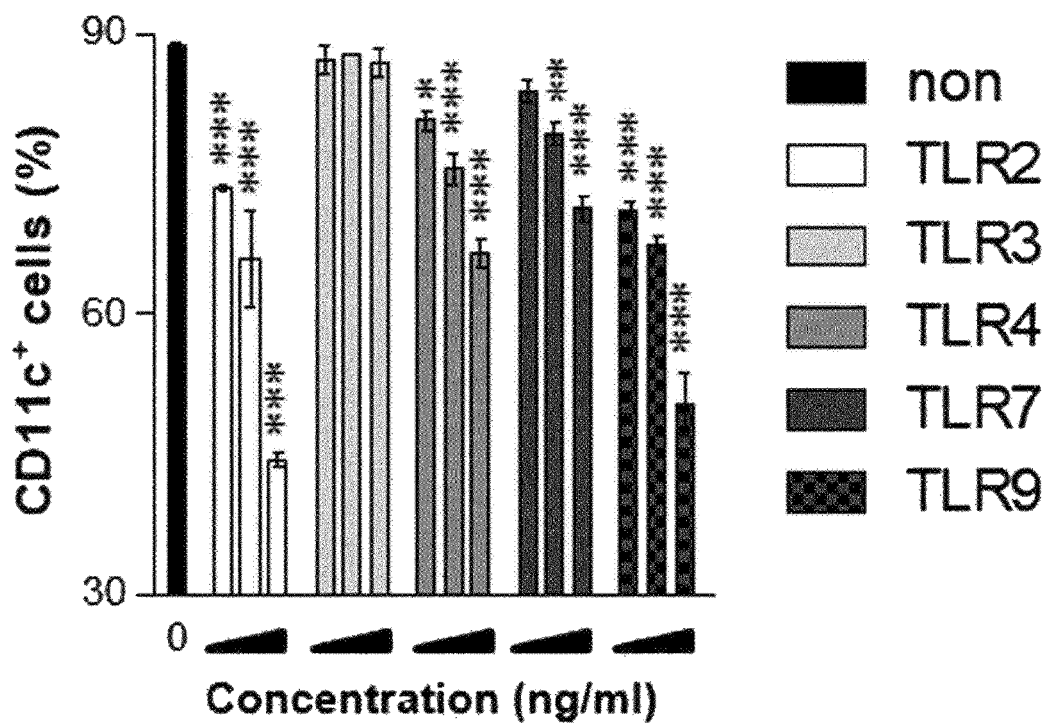
[FIG. 5]
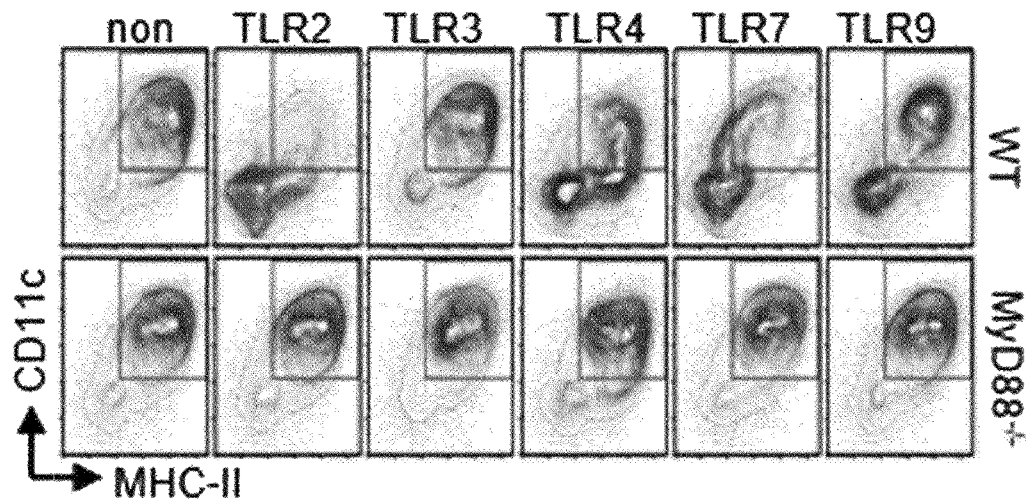

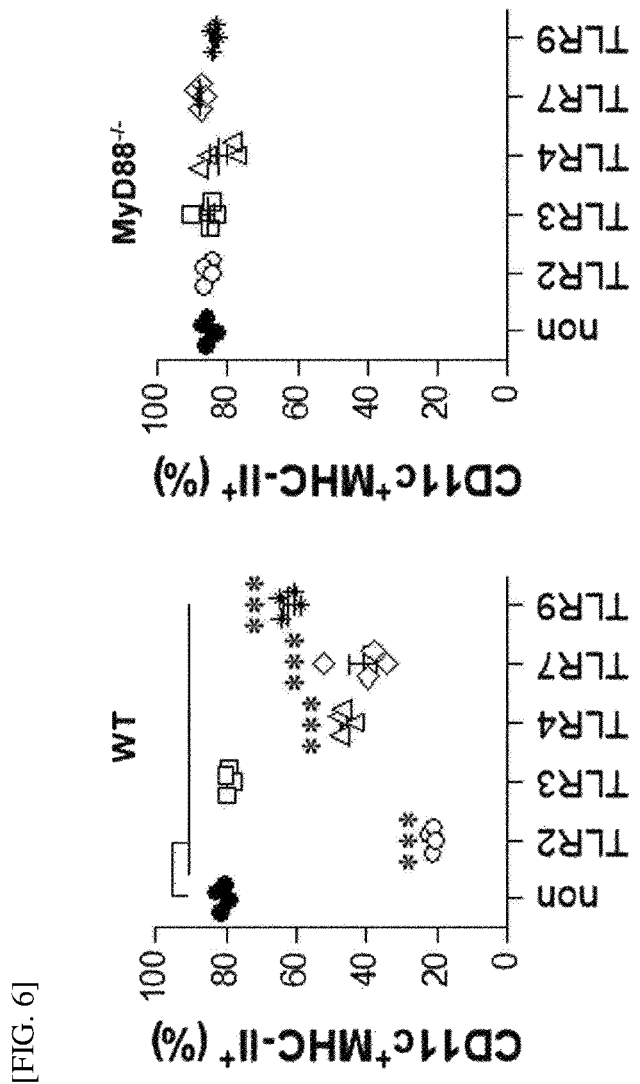
[FIG. 6]

[FIG. 7]
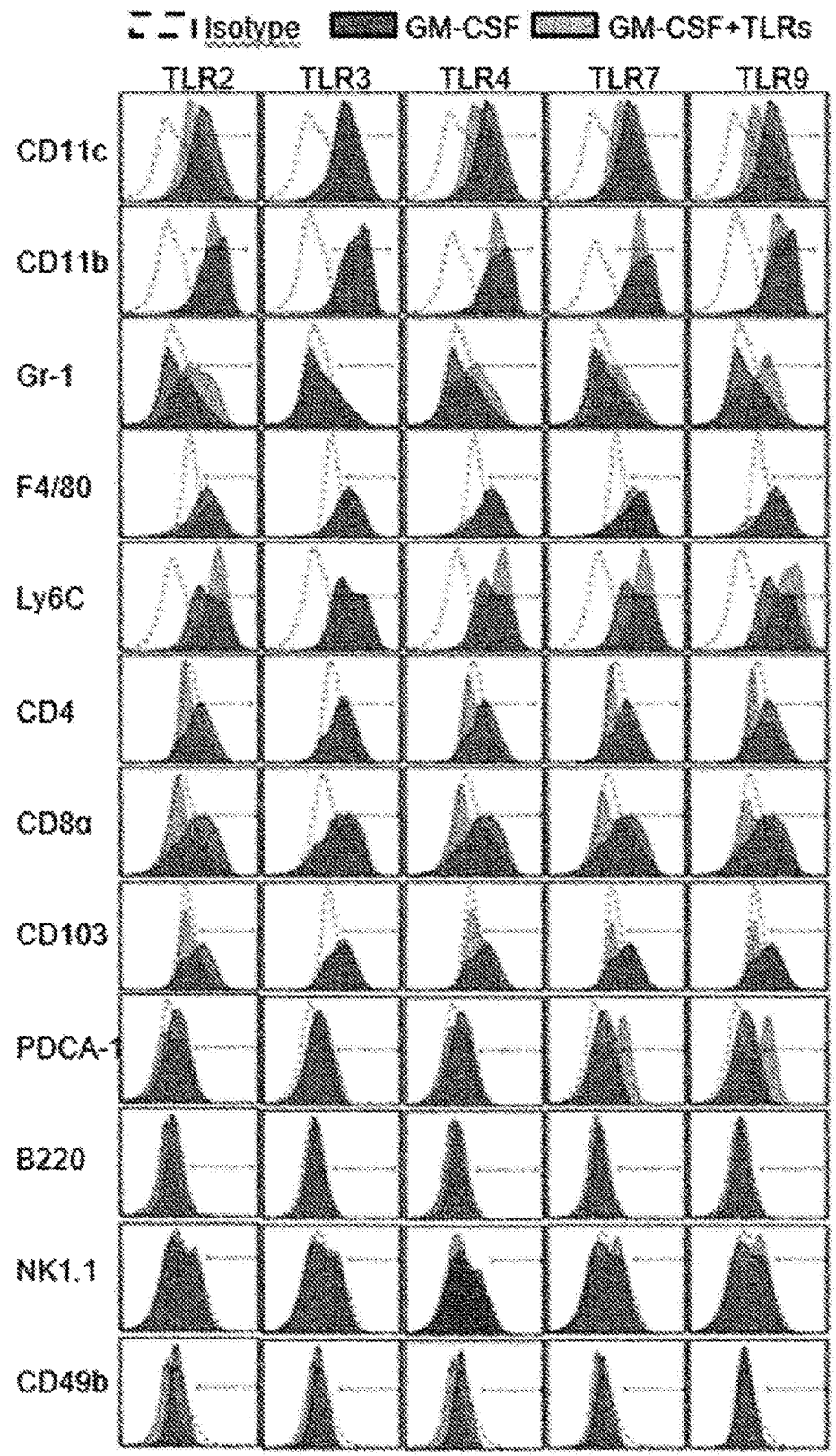

[FIG. 8]
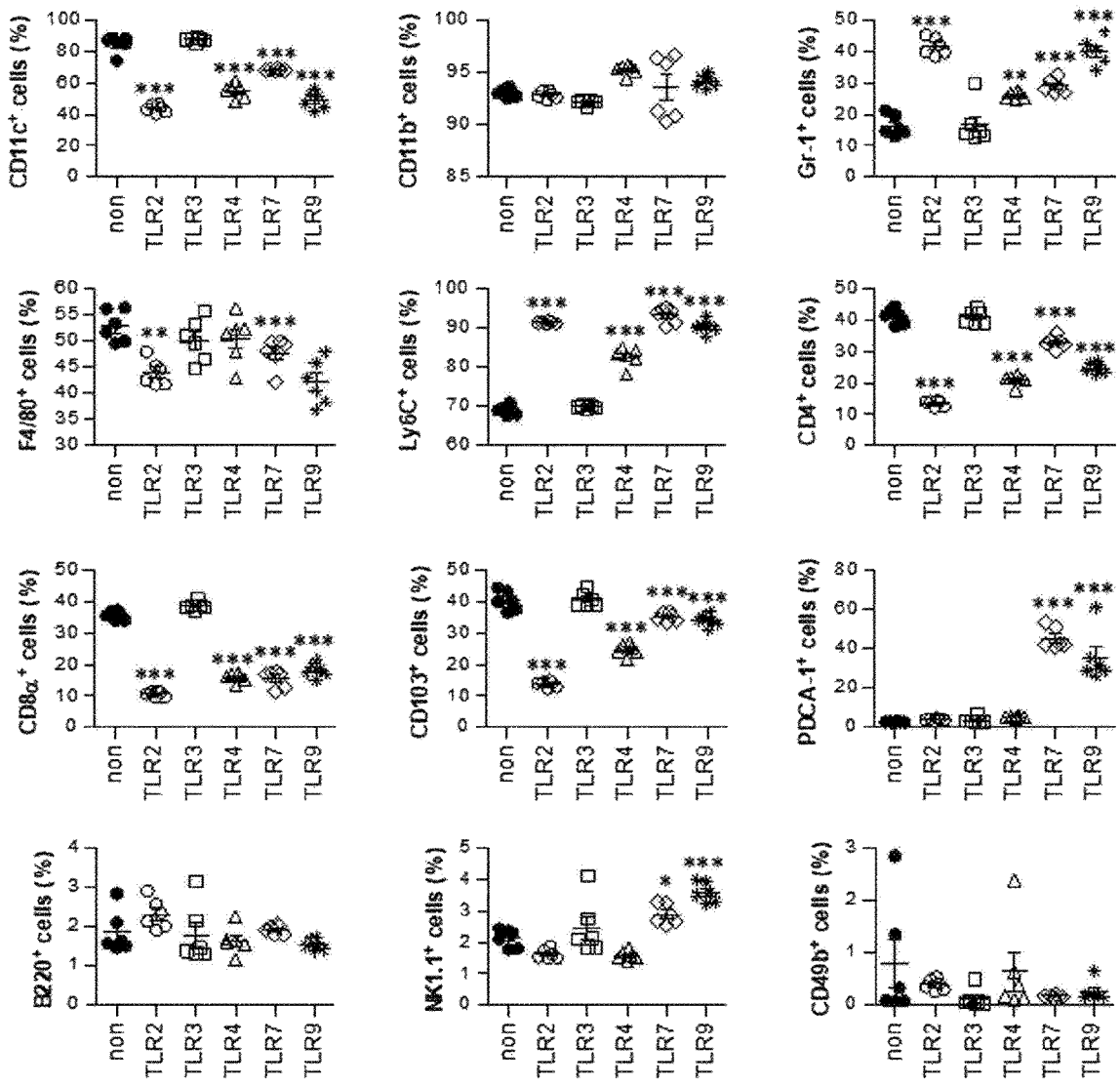

[FIG. 9]
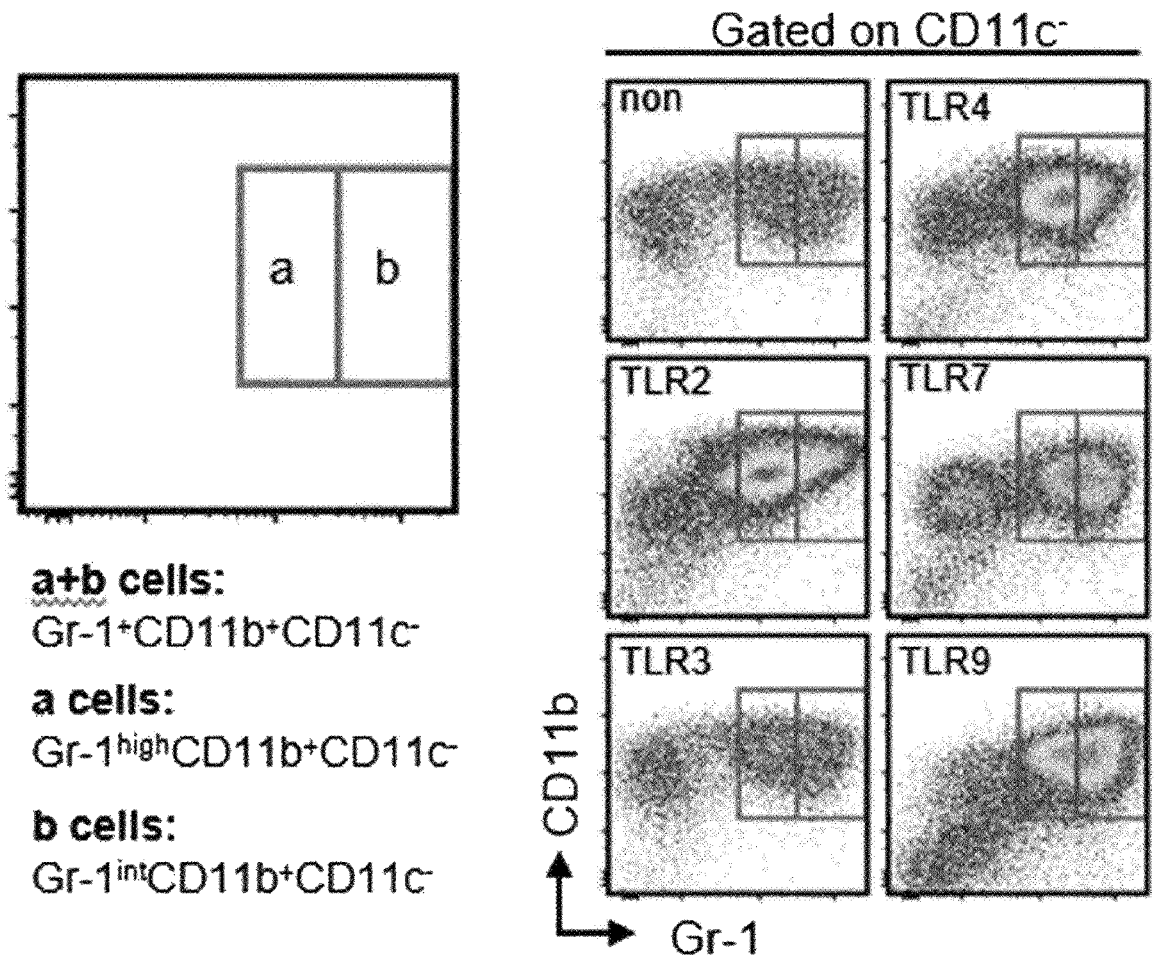
[FIG. 10]
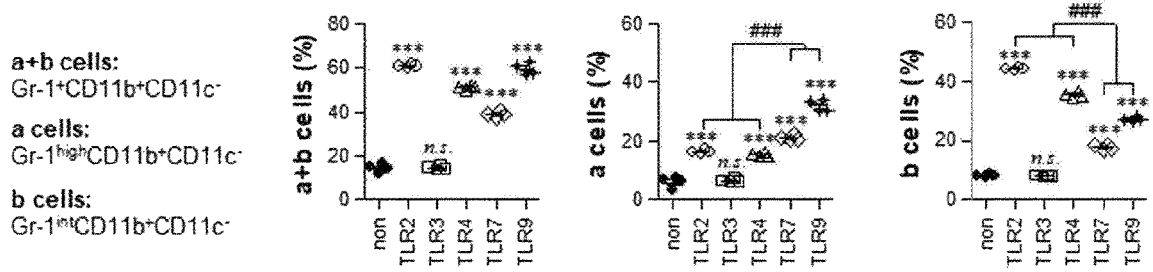

[FIG. 11]
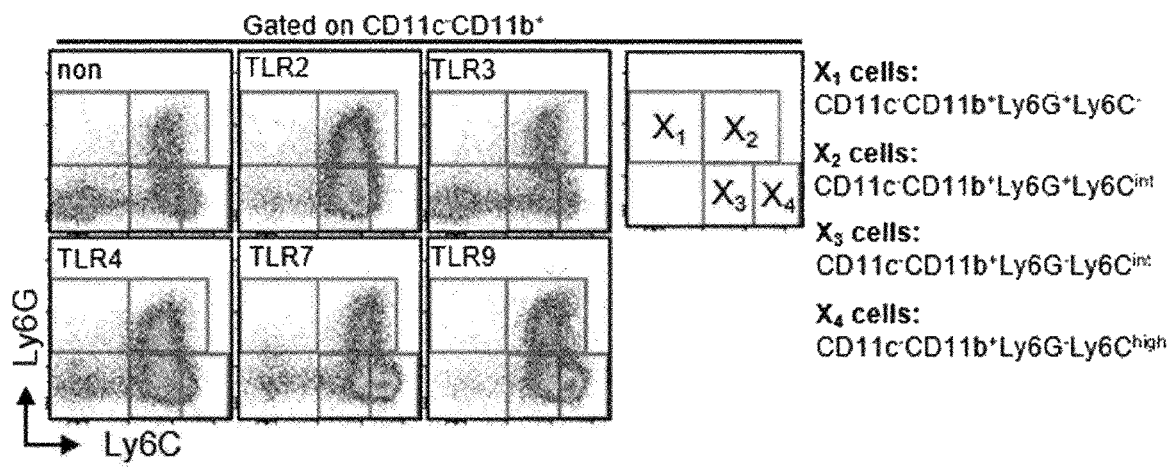
[FIG. 12]
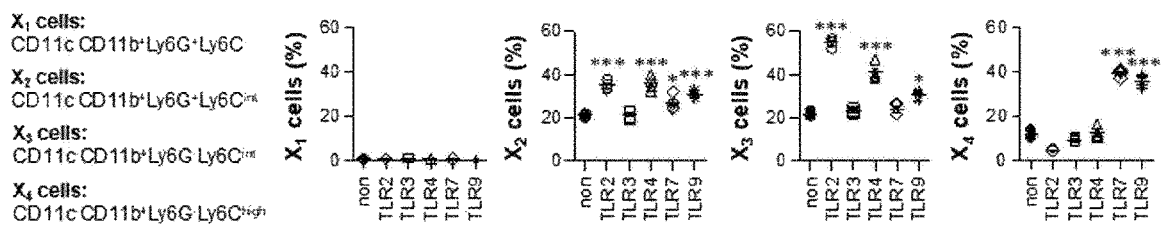

[FIG. 13]
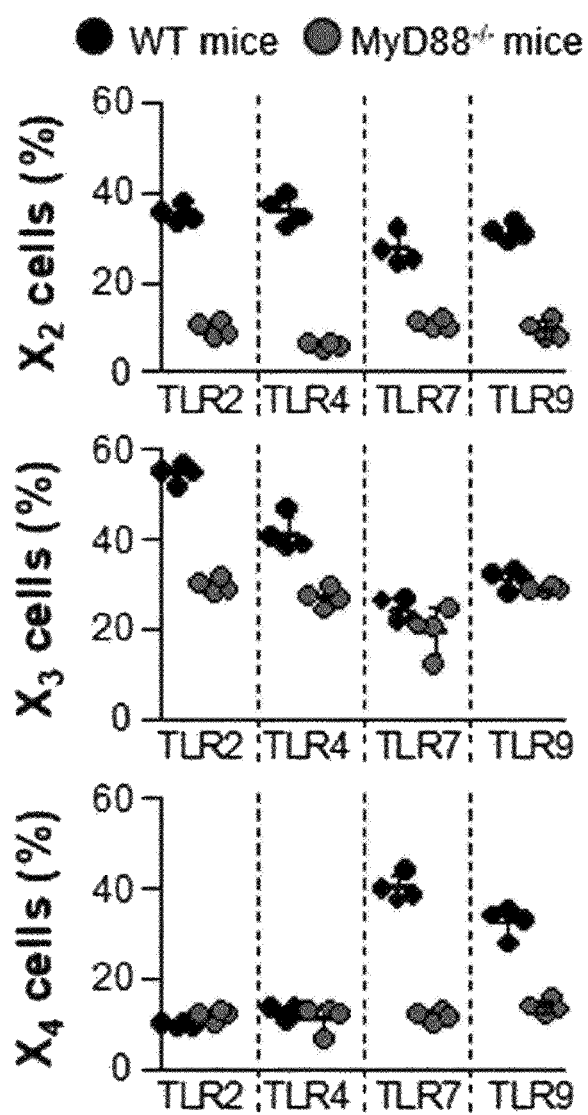
$X_1$ cells:
CD11c⁻CD11b⁺Ly6G⁺Ly6C⁻
$X_2$ cells:
CD11c⁻CD11b⁺Ly6G⁺Ly6C$^{int}$
$X_3$ cells:
CD11c⁻CD11b⁺Ly6G⁻Ly6C$^{int}$
$X_4$ cells:
CD11c⁻CD11b⁺Ly6G⁻Ly6C$^{high}$

[FIG. 14]
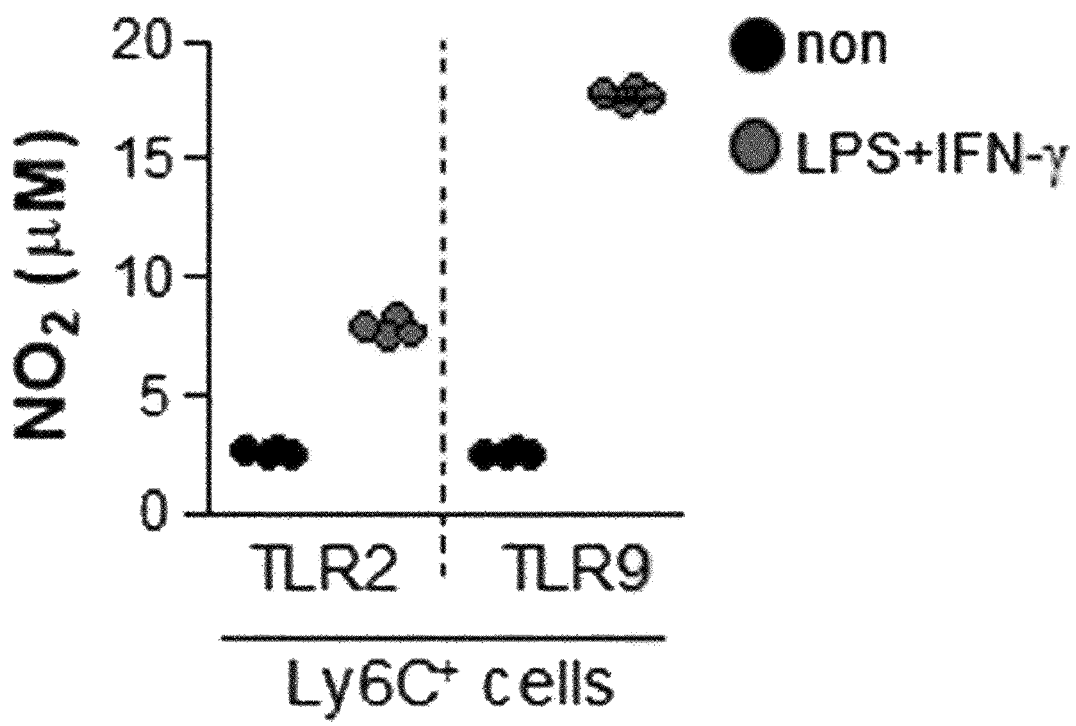
[FIG. 15]
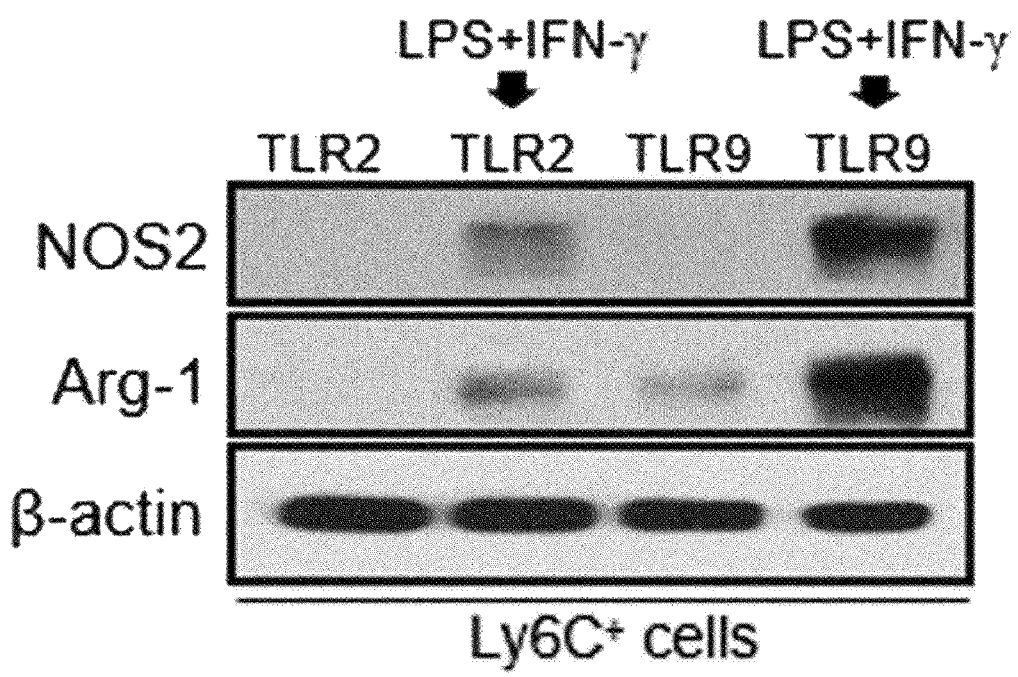

[FIG. 16]
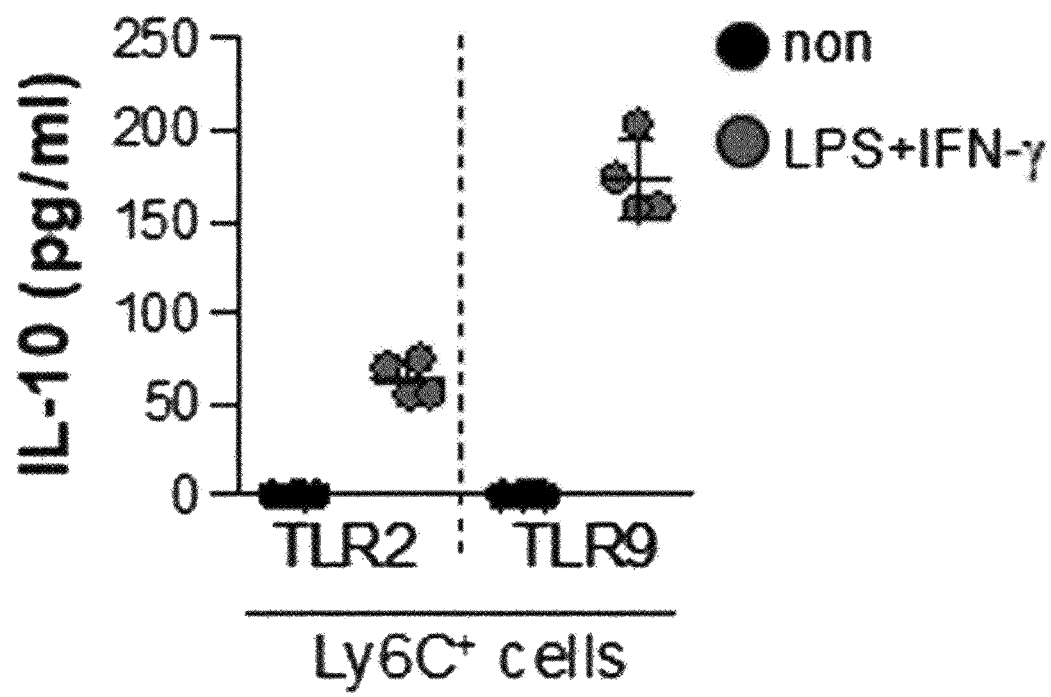

[FIG. 17]
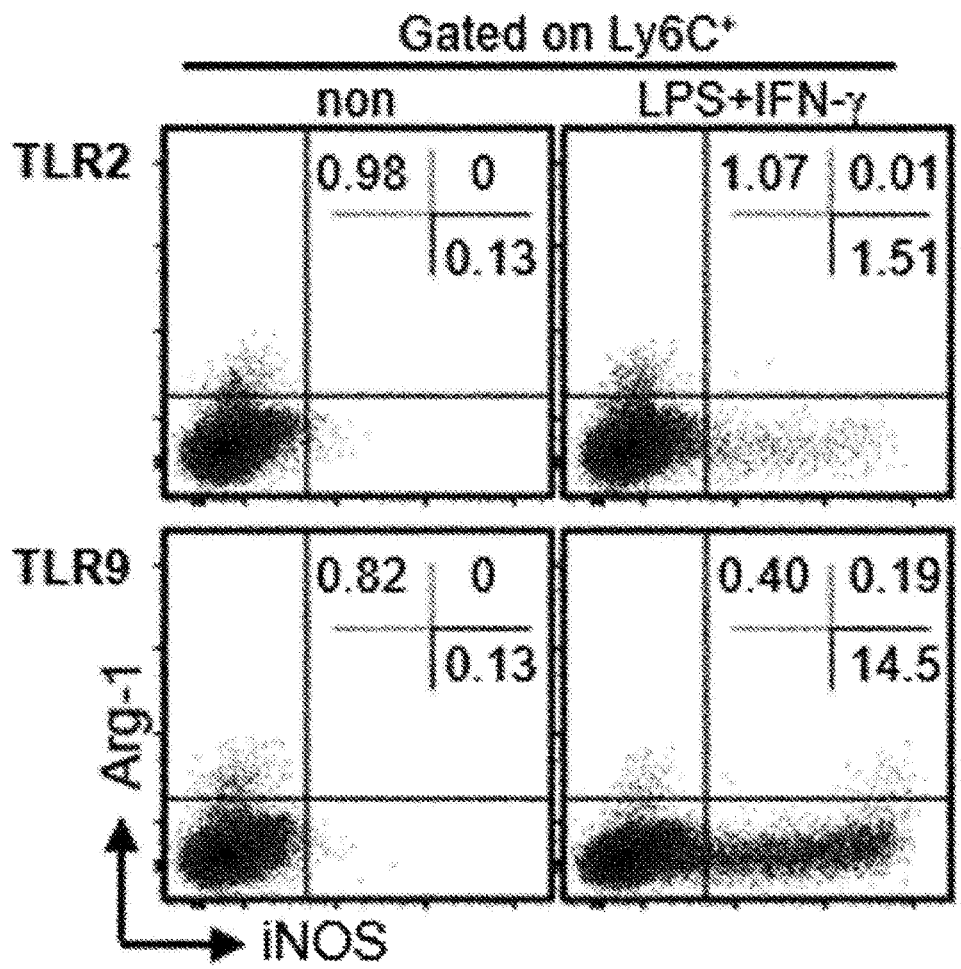
[FIG. 18]
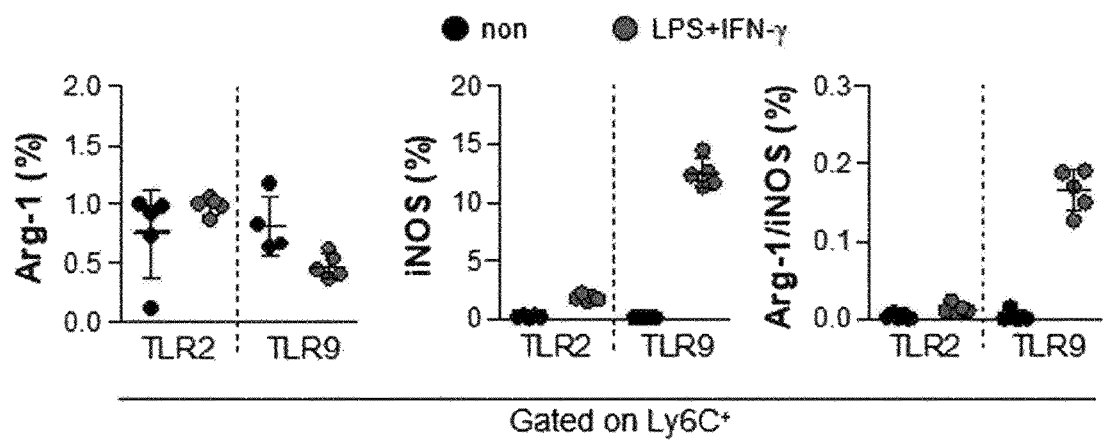

[FIG. 19]
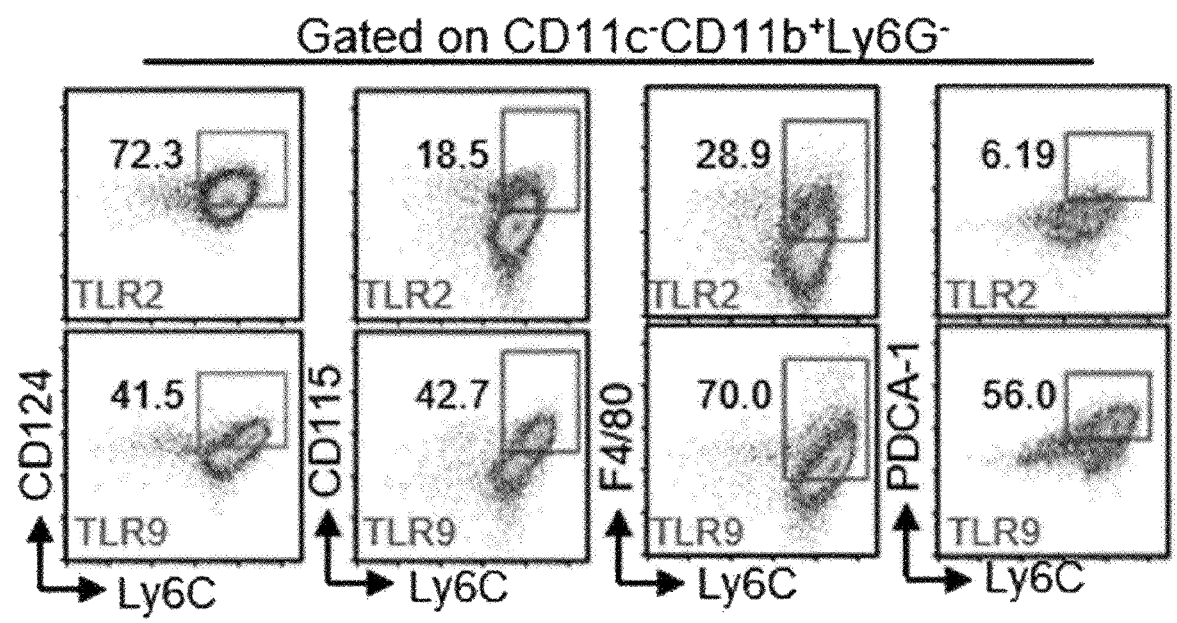
[FIG. 20]
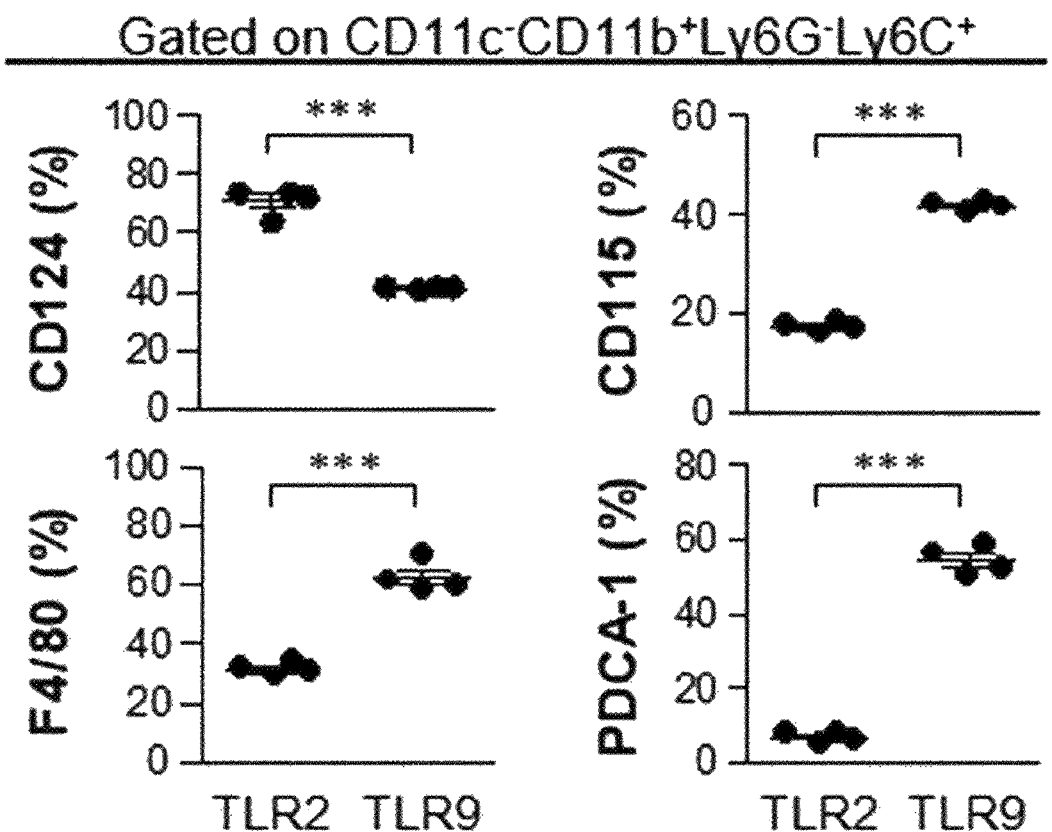

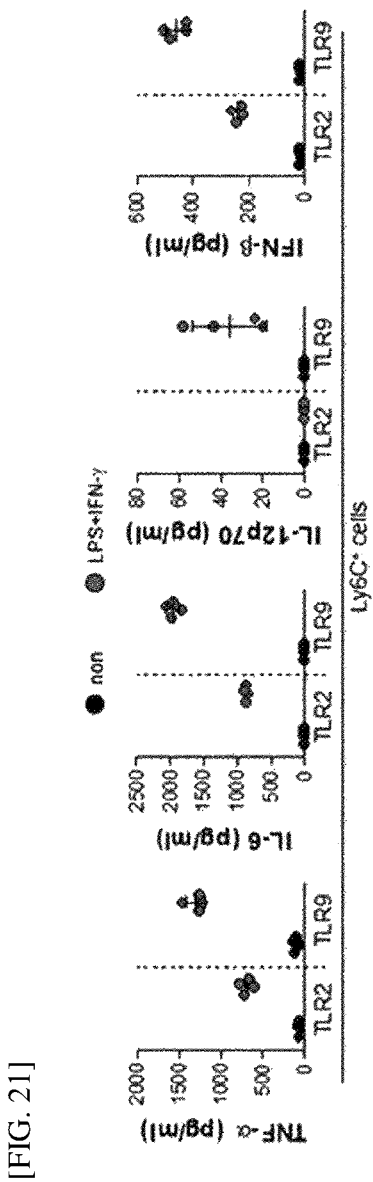
[FIG. 21]

[FIG. 22]
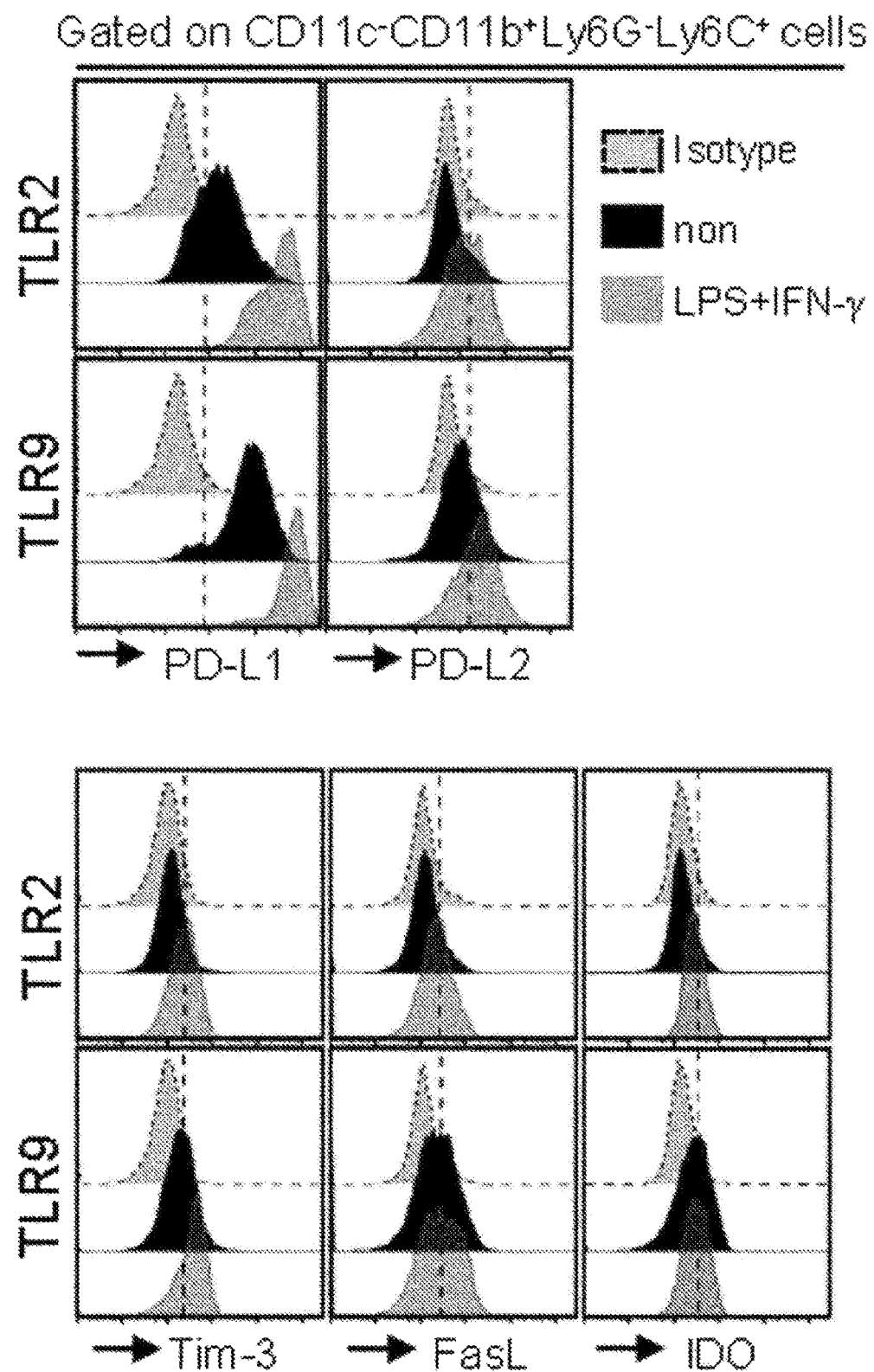

[FIG. 23]
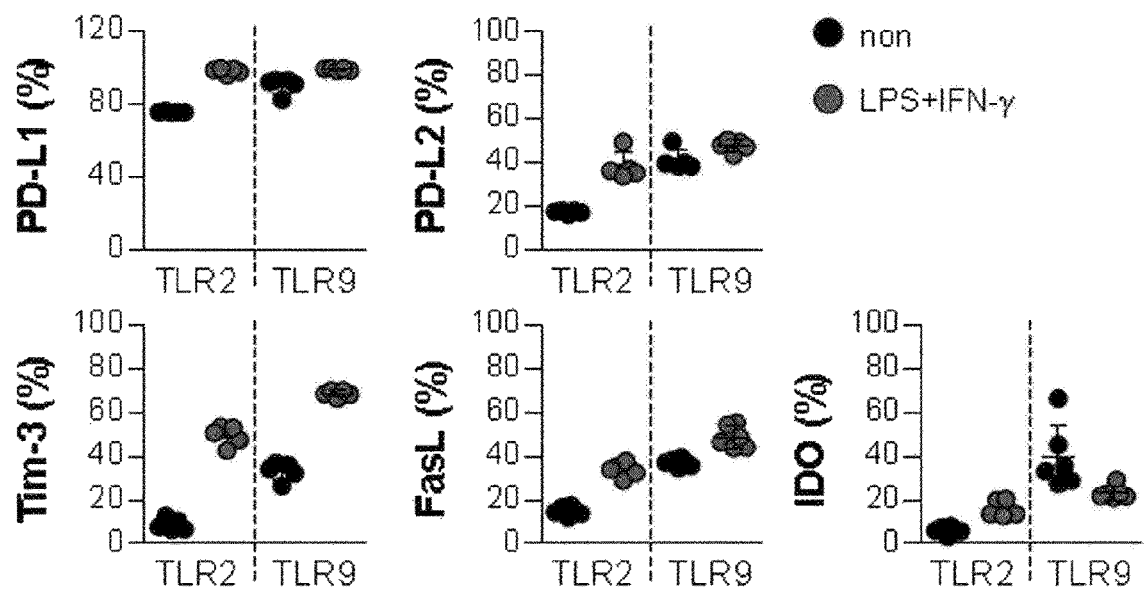
[FIG. 24]
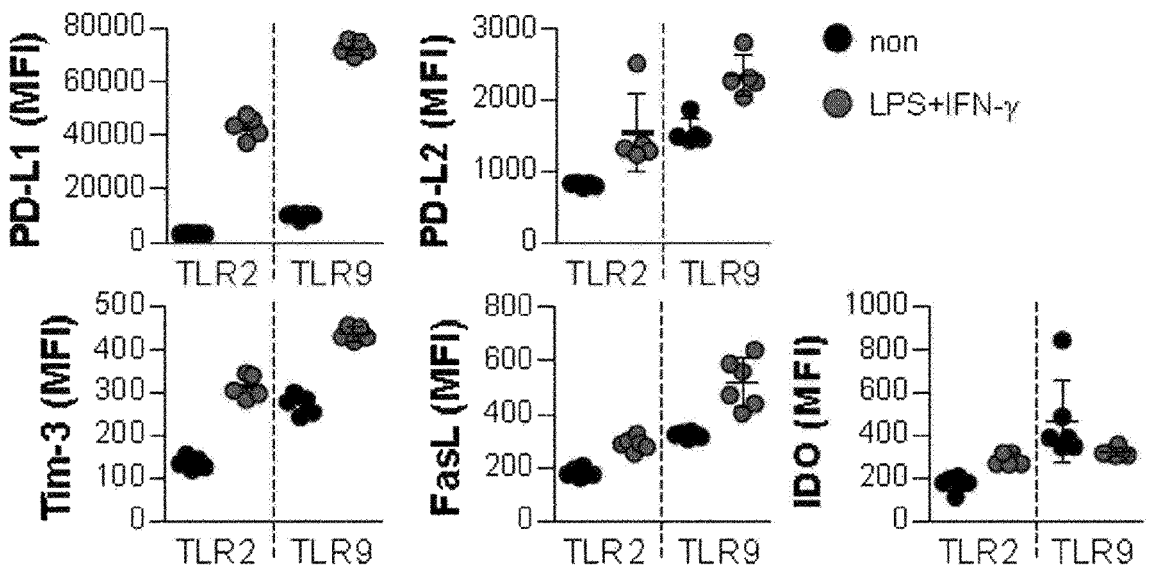

[FIG. 25]
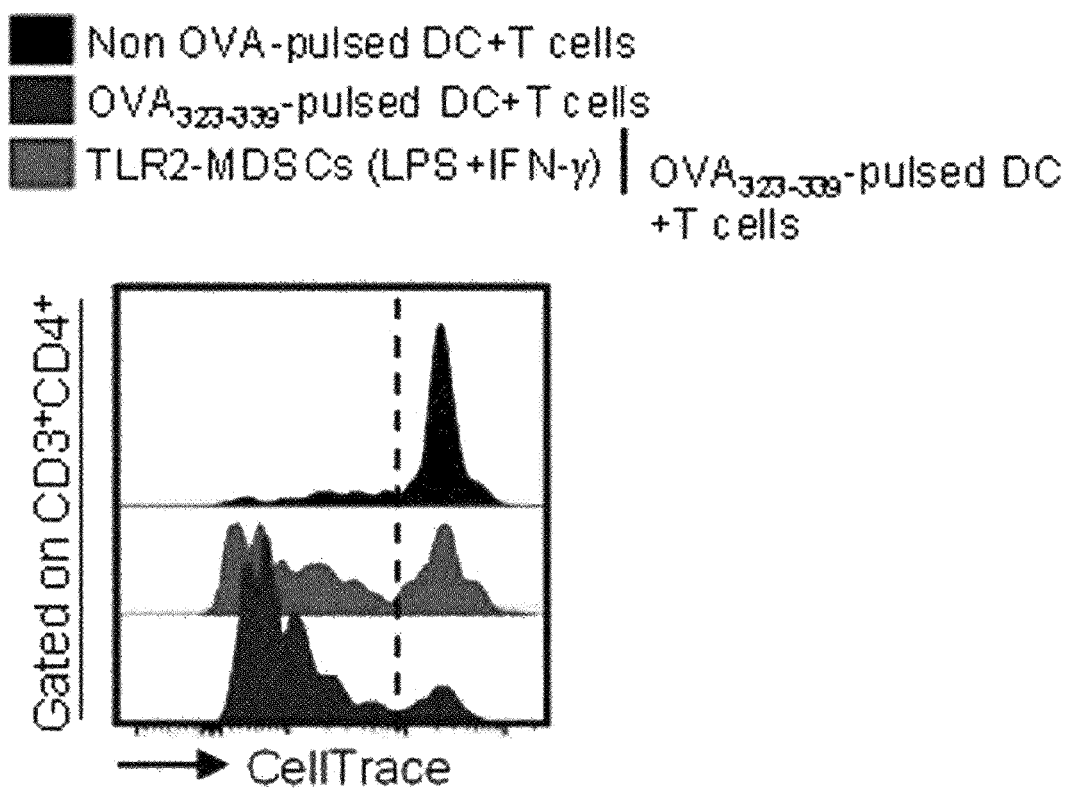

[FIG. 26]
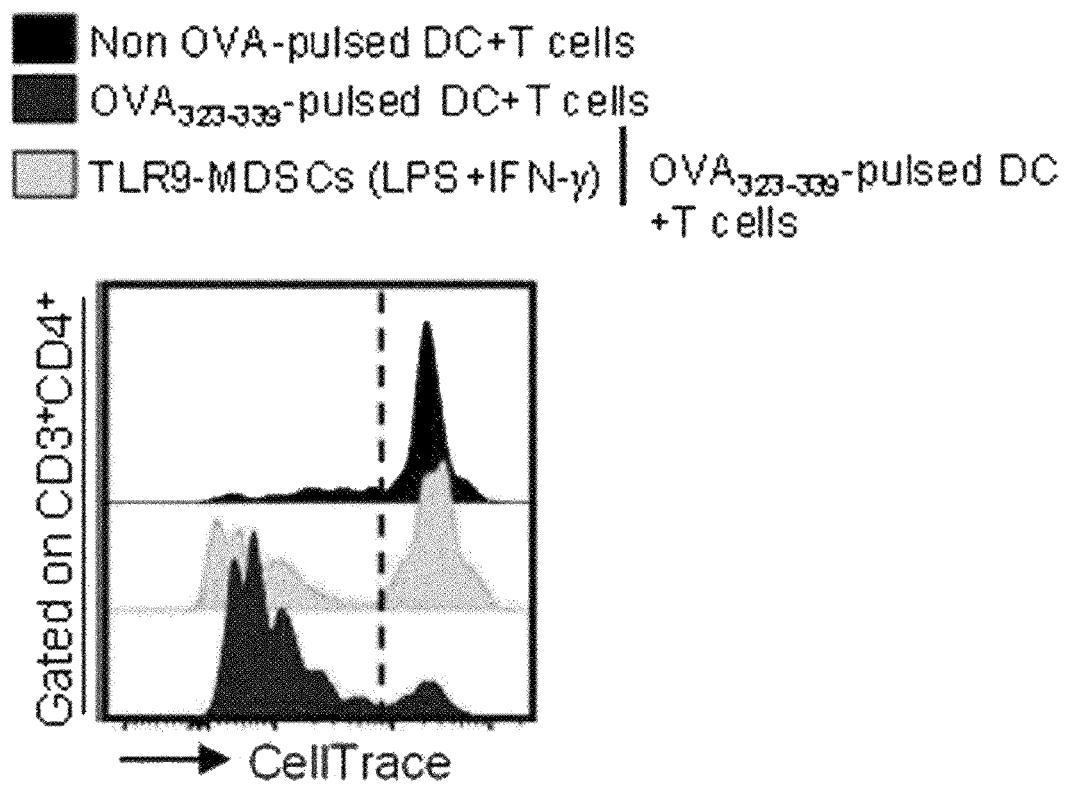

[FIG. 27]
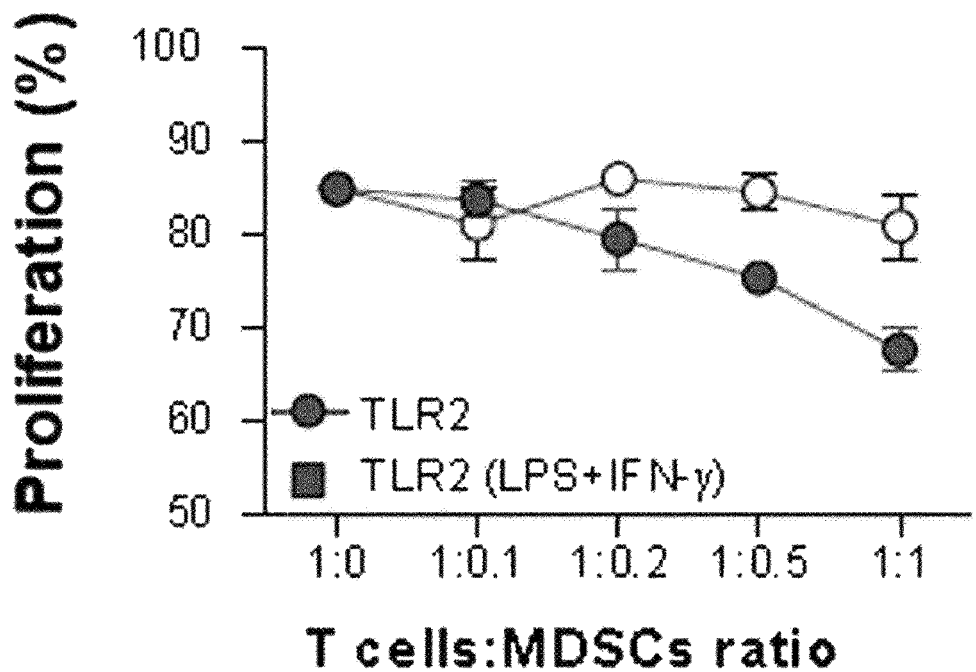
[FIG. 28]
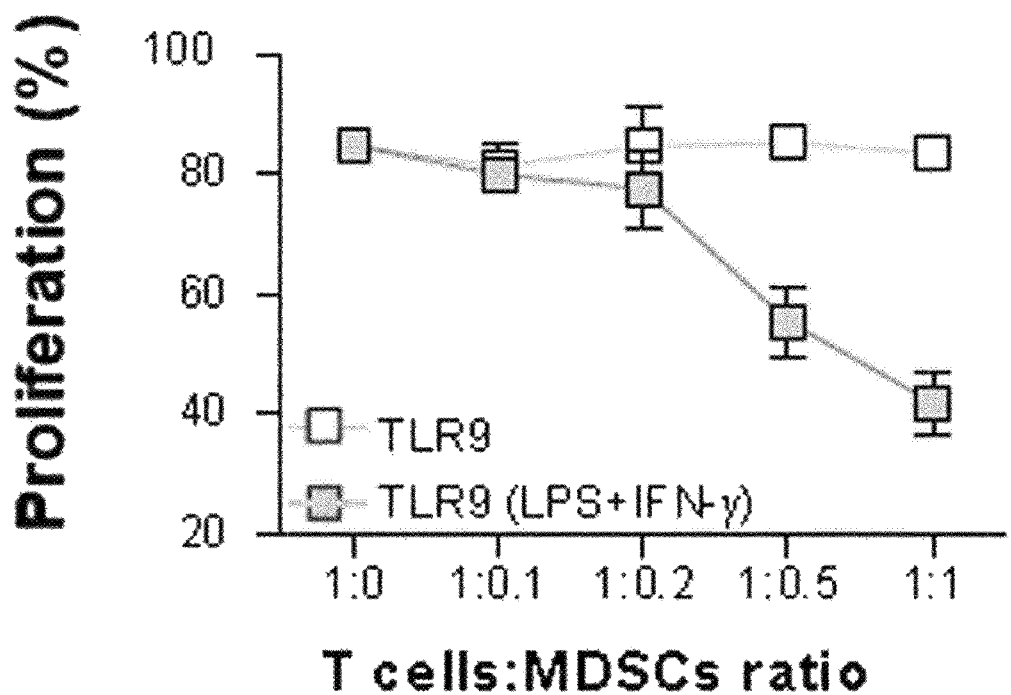

[FIG. 29]
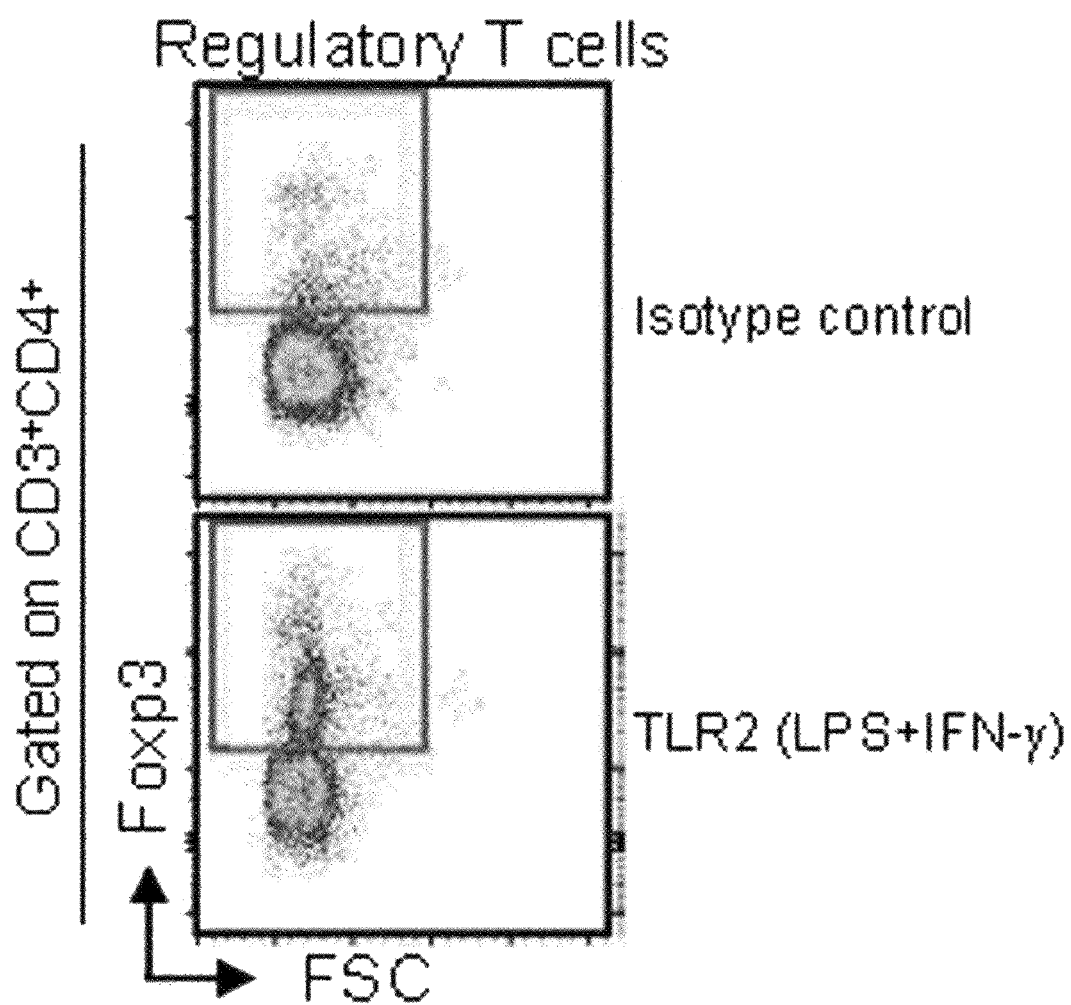

[FIG. 30]
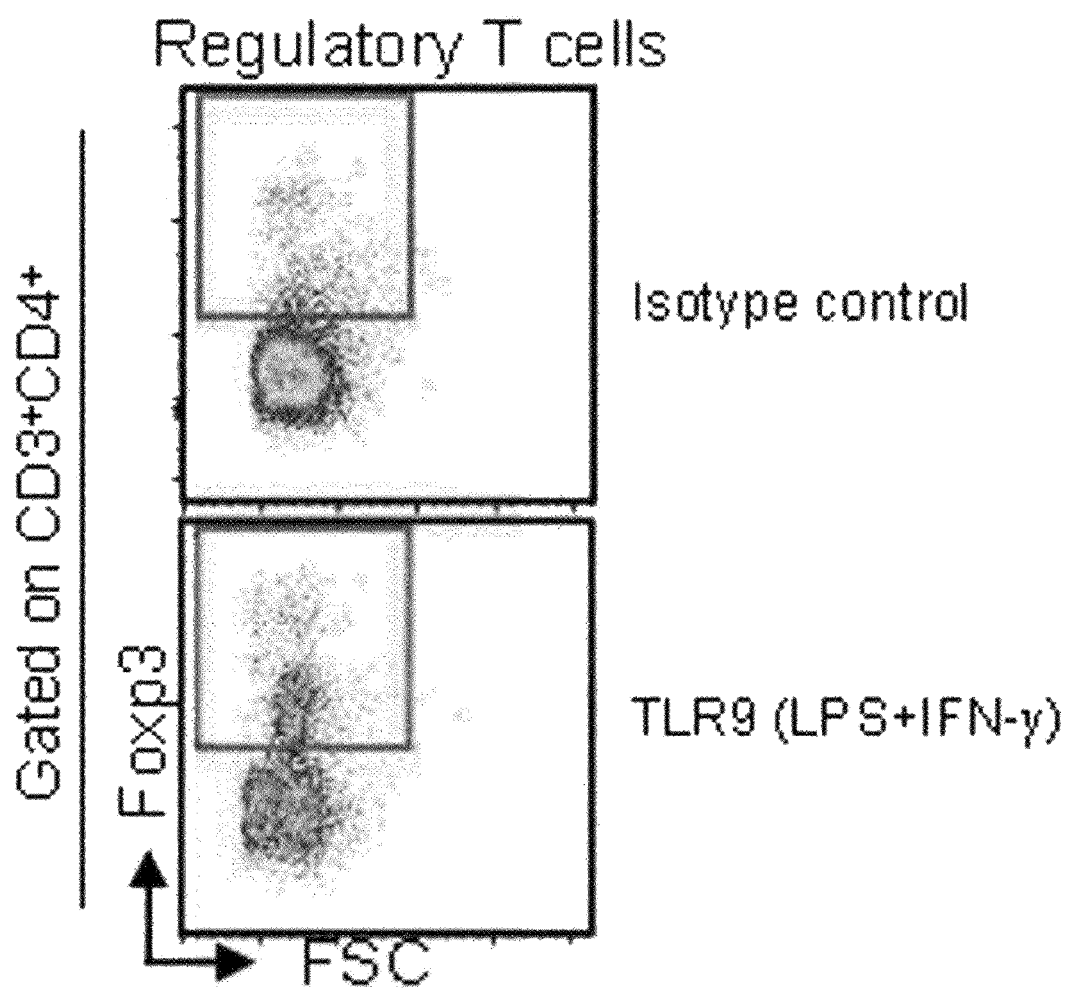

[FIG. 31]
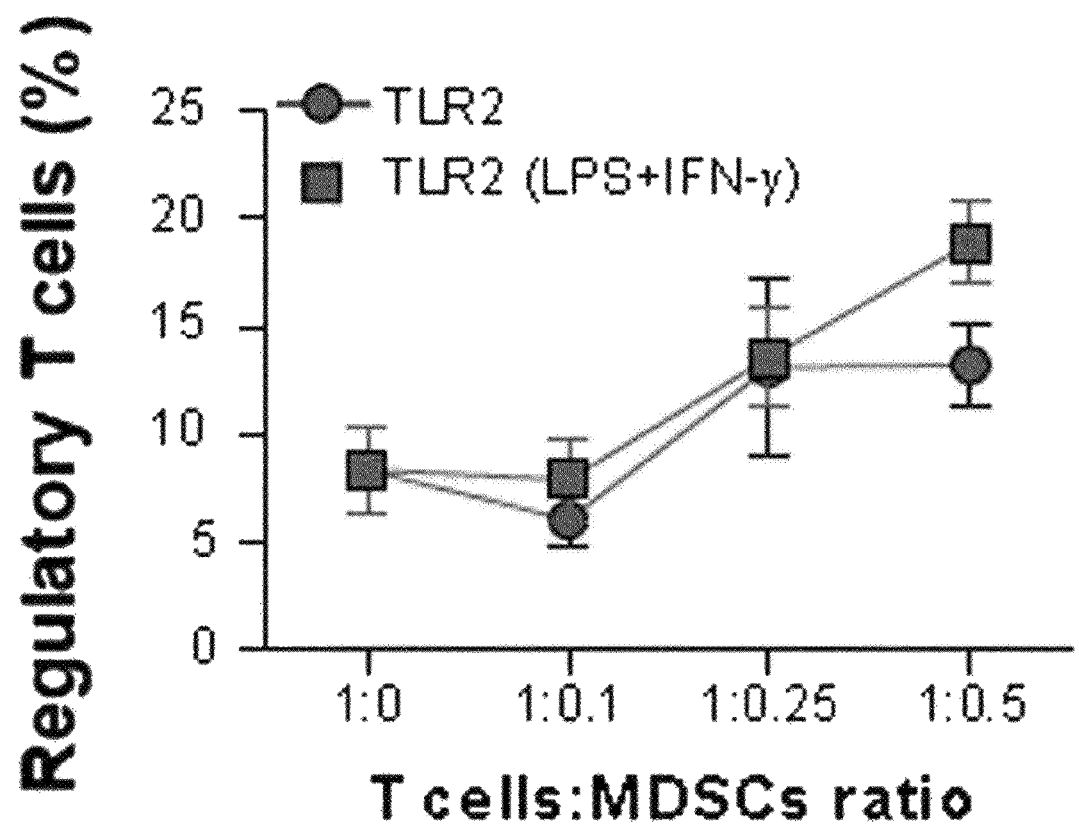

[FIG. 32]
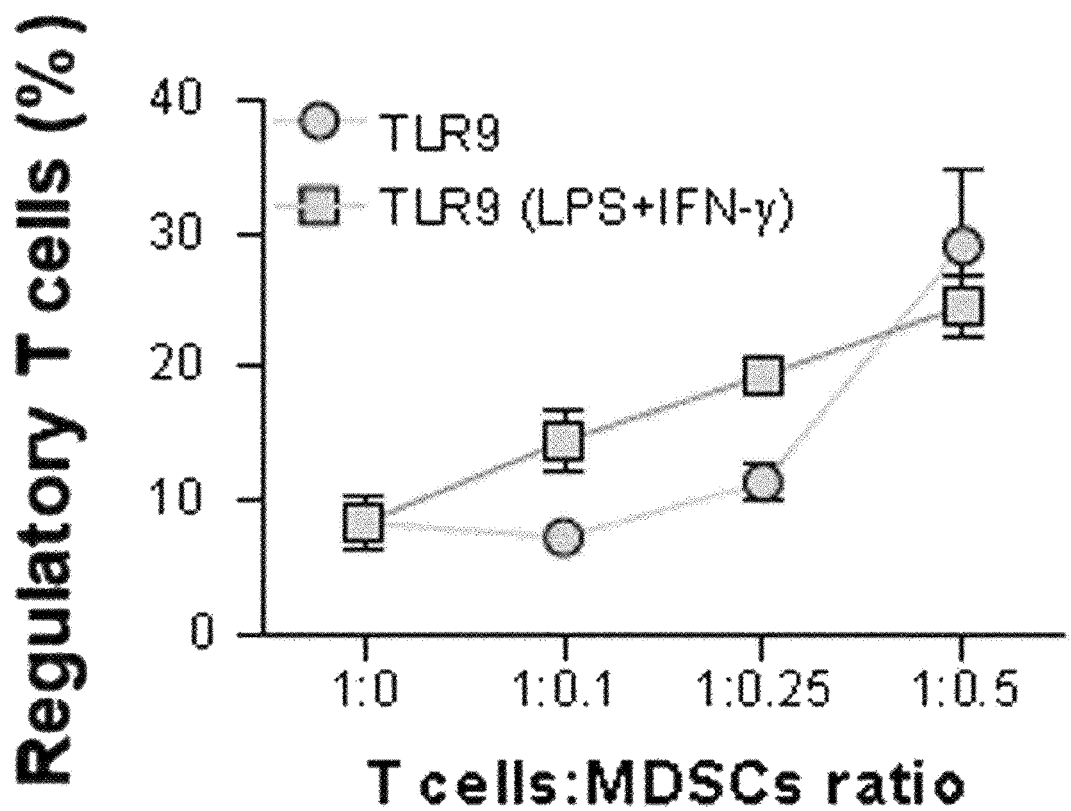

[FIG. 33]
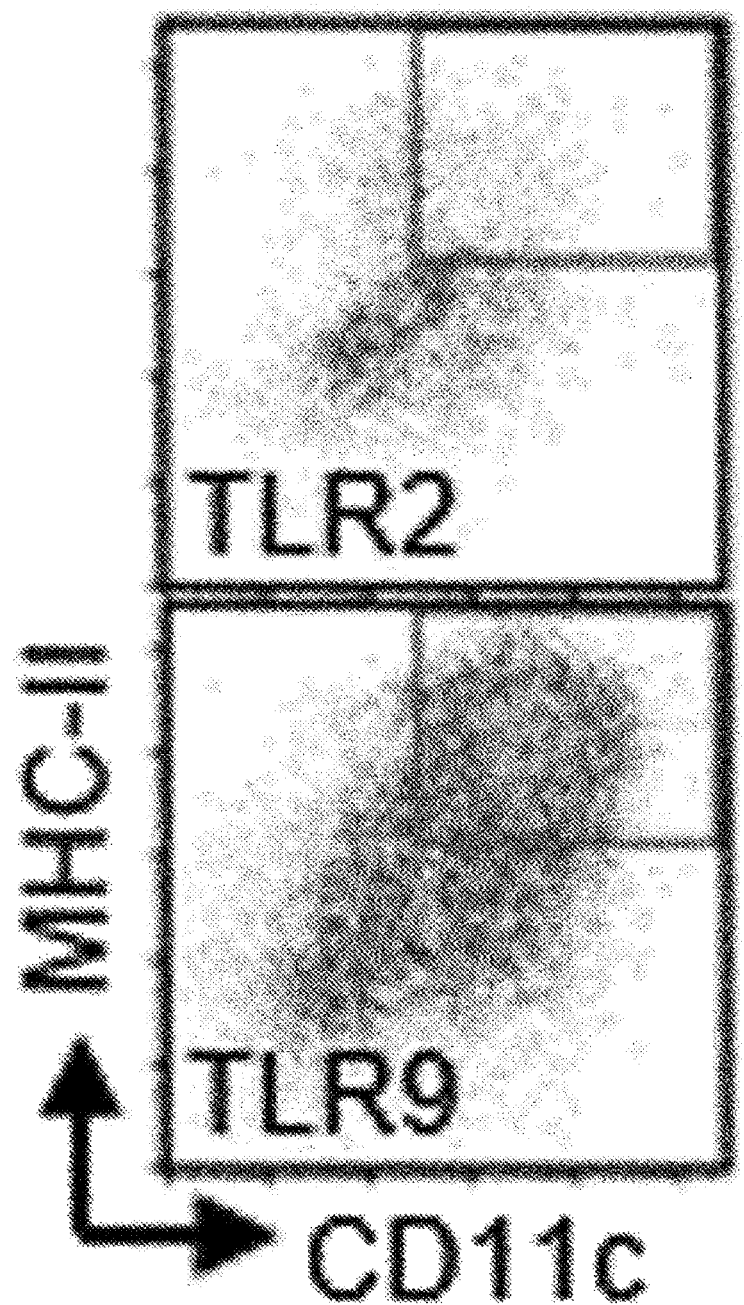

[FIG. 34]
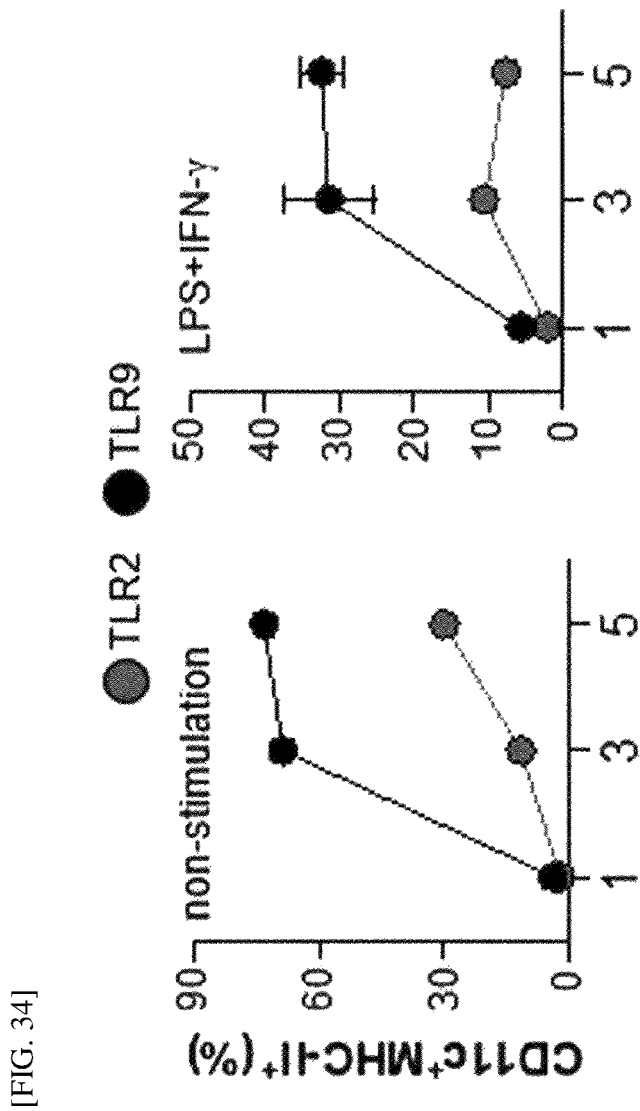

[FIG. 35]

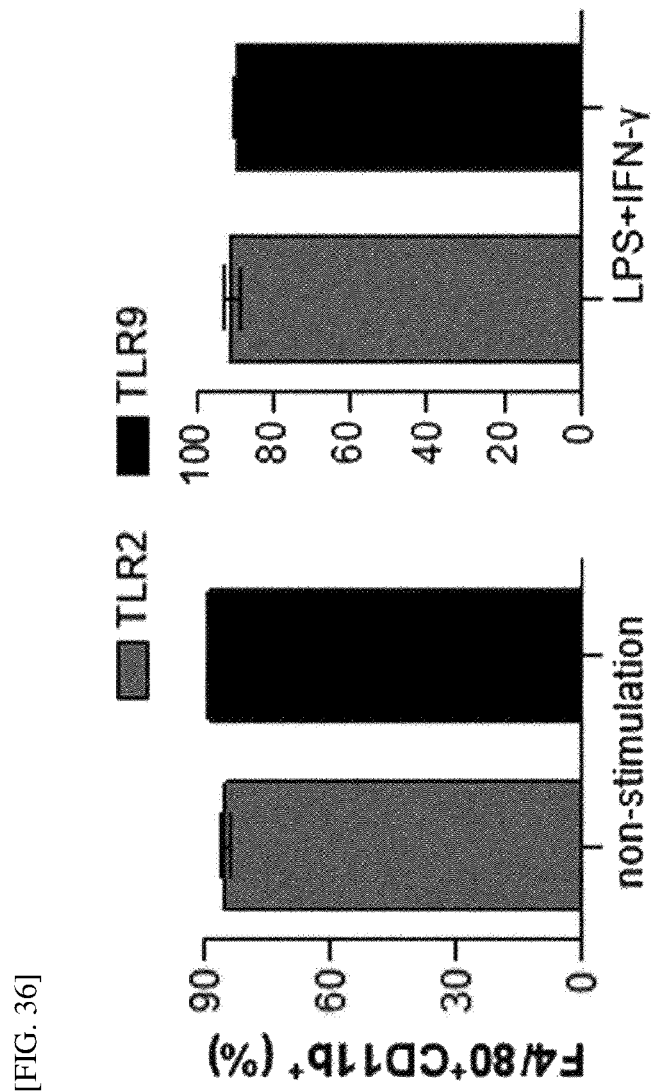
[FIG. 36]

[FIG. 37]
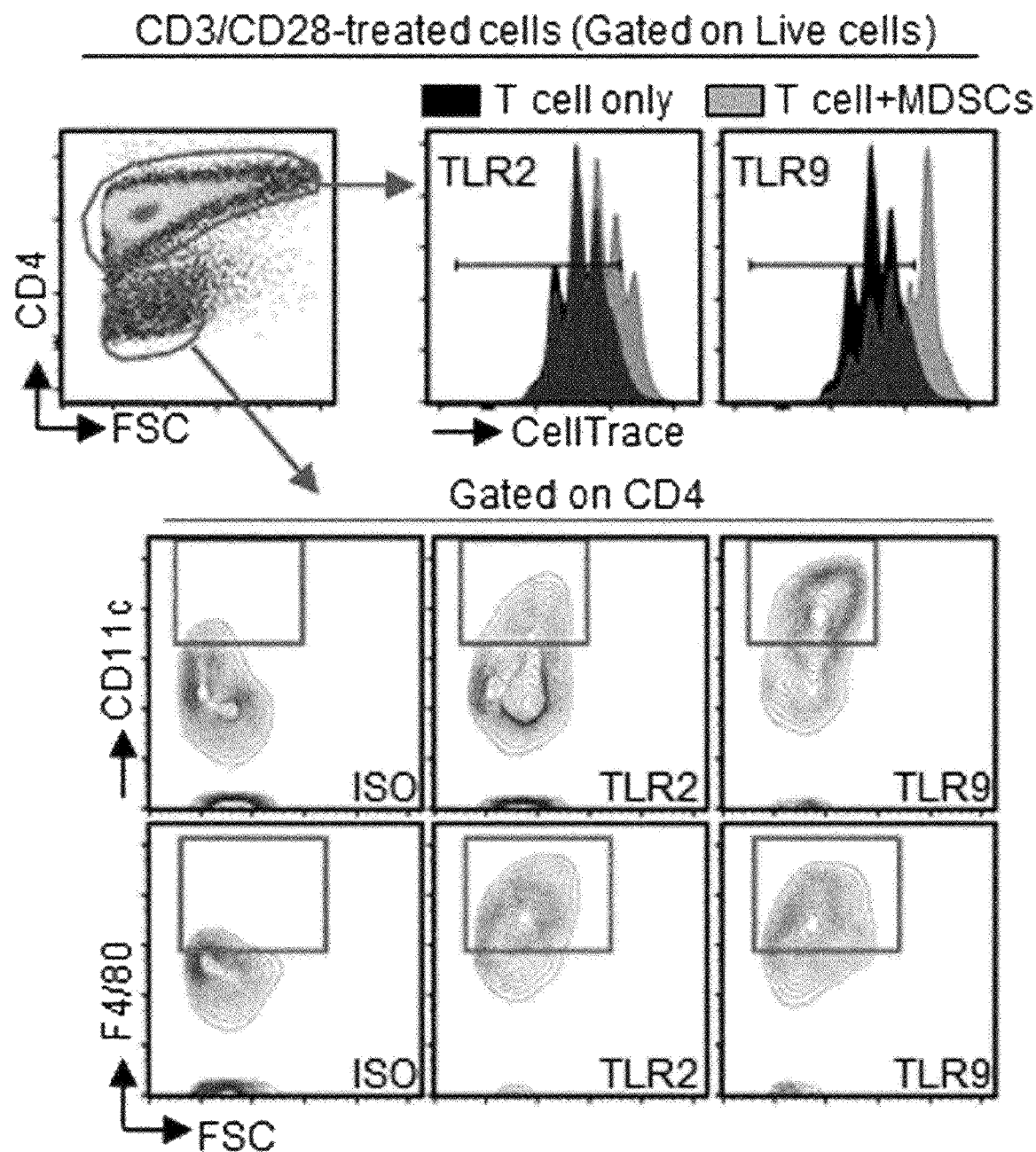

[FIG. 38]
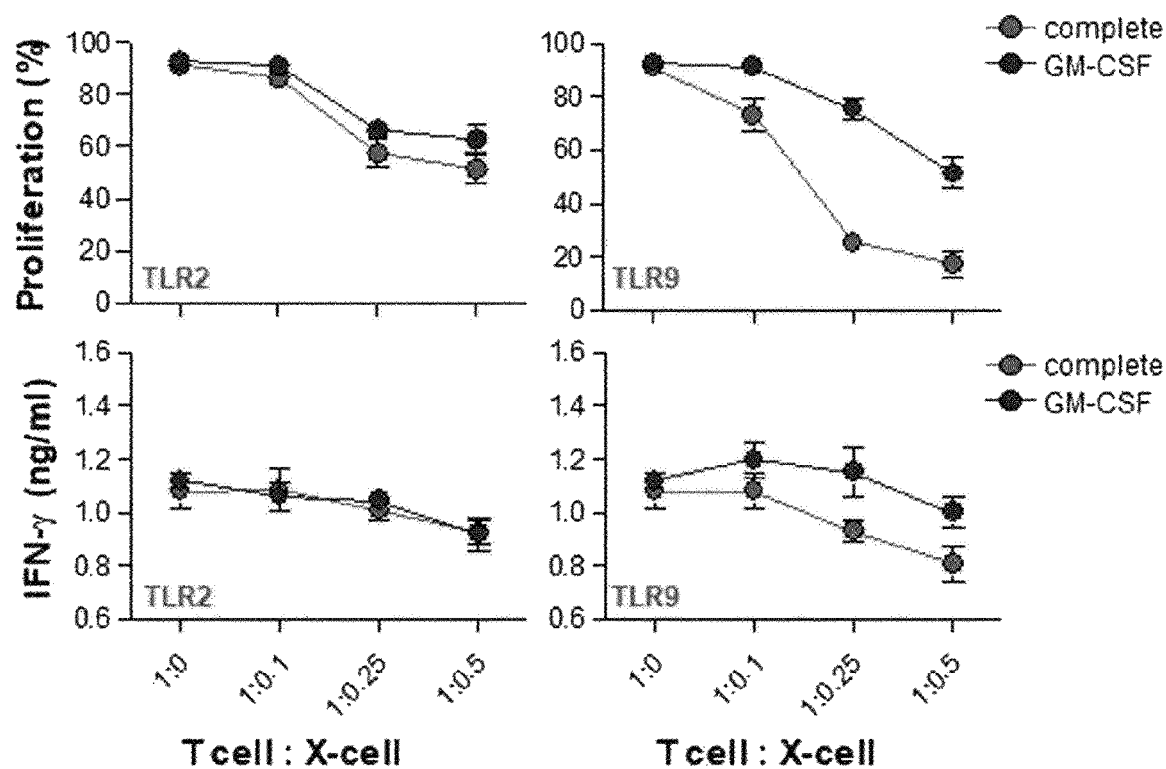

[FIG. 39]
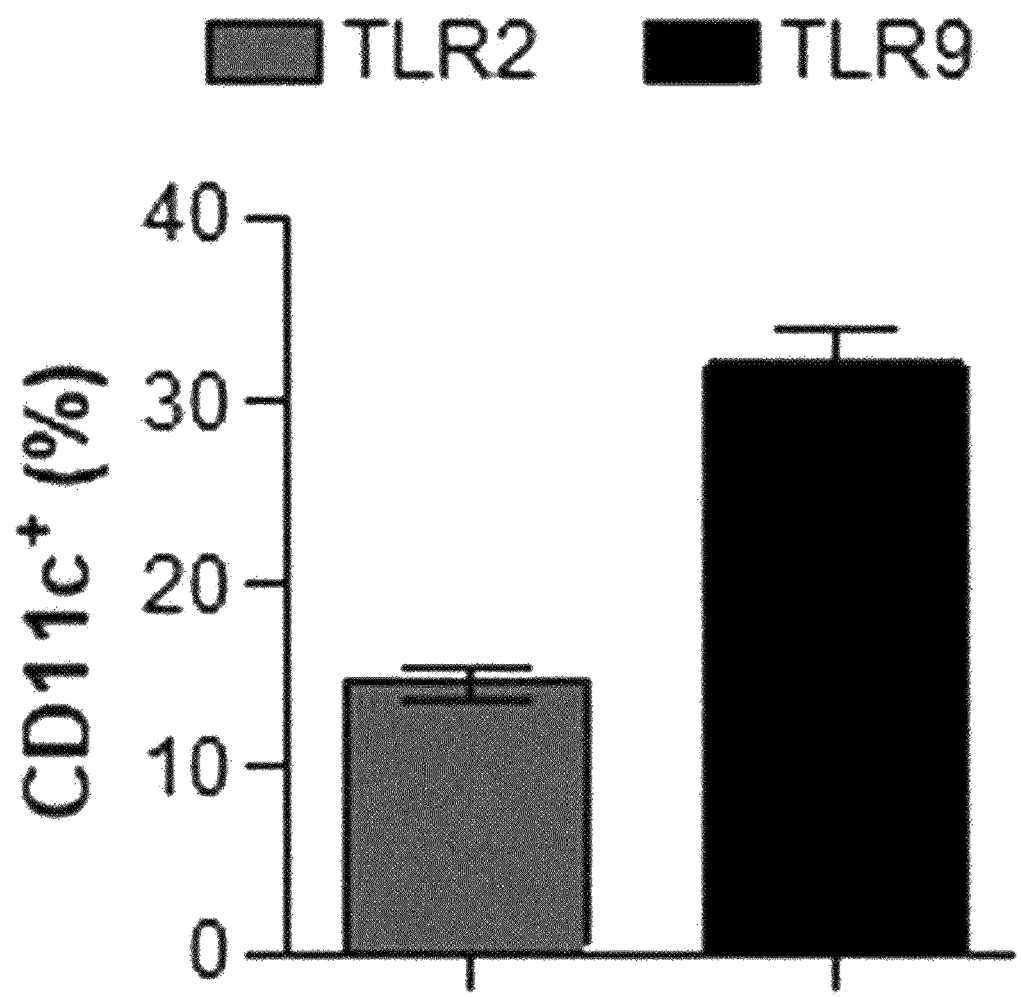

[FIG. 40]
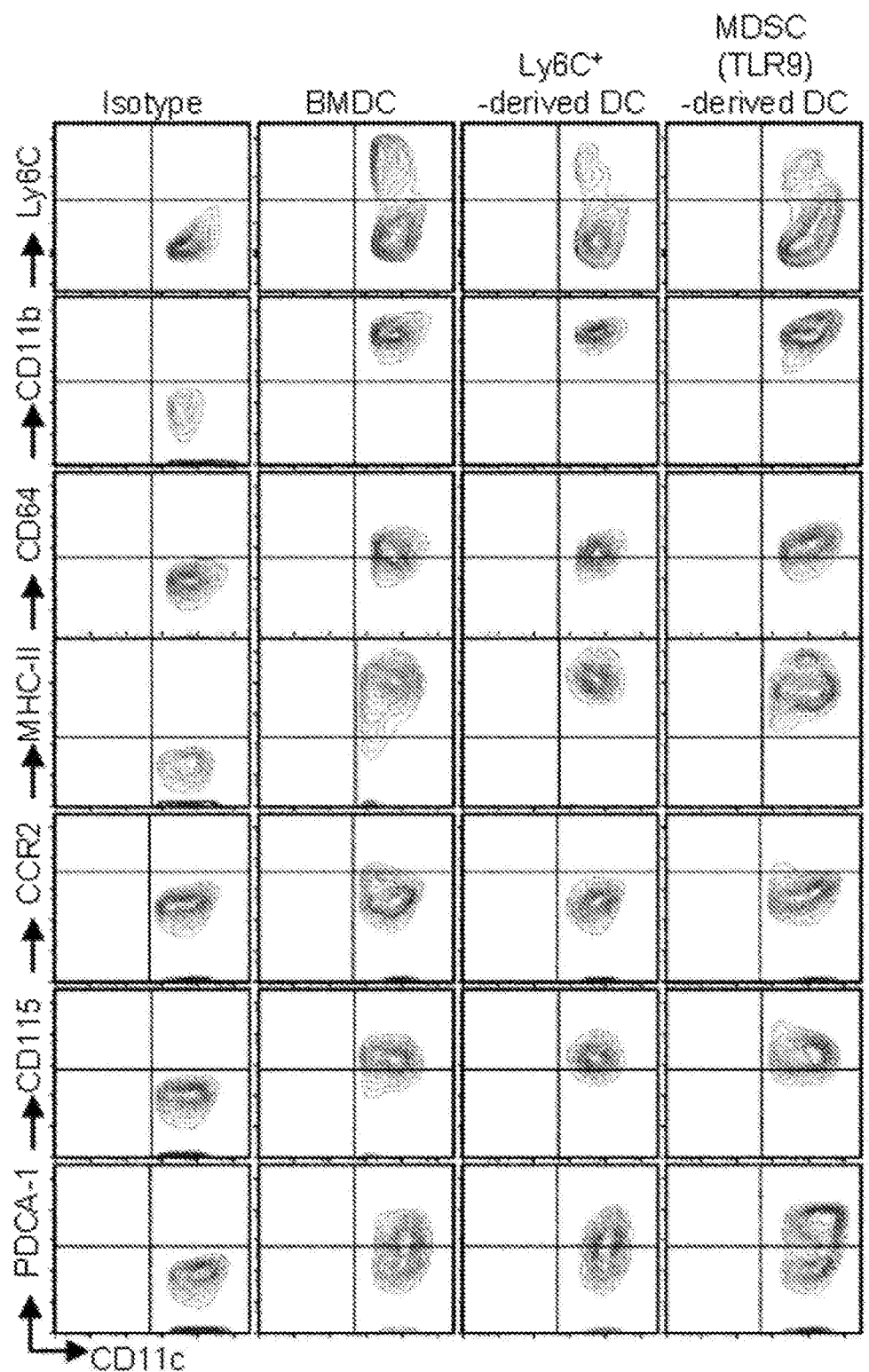

[FIG. 41]
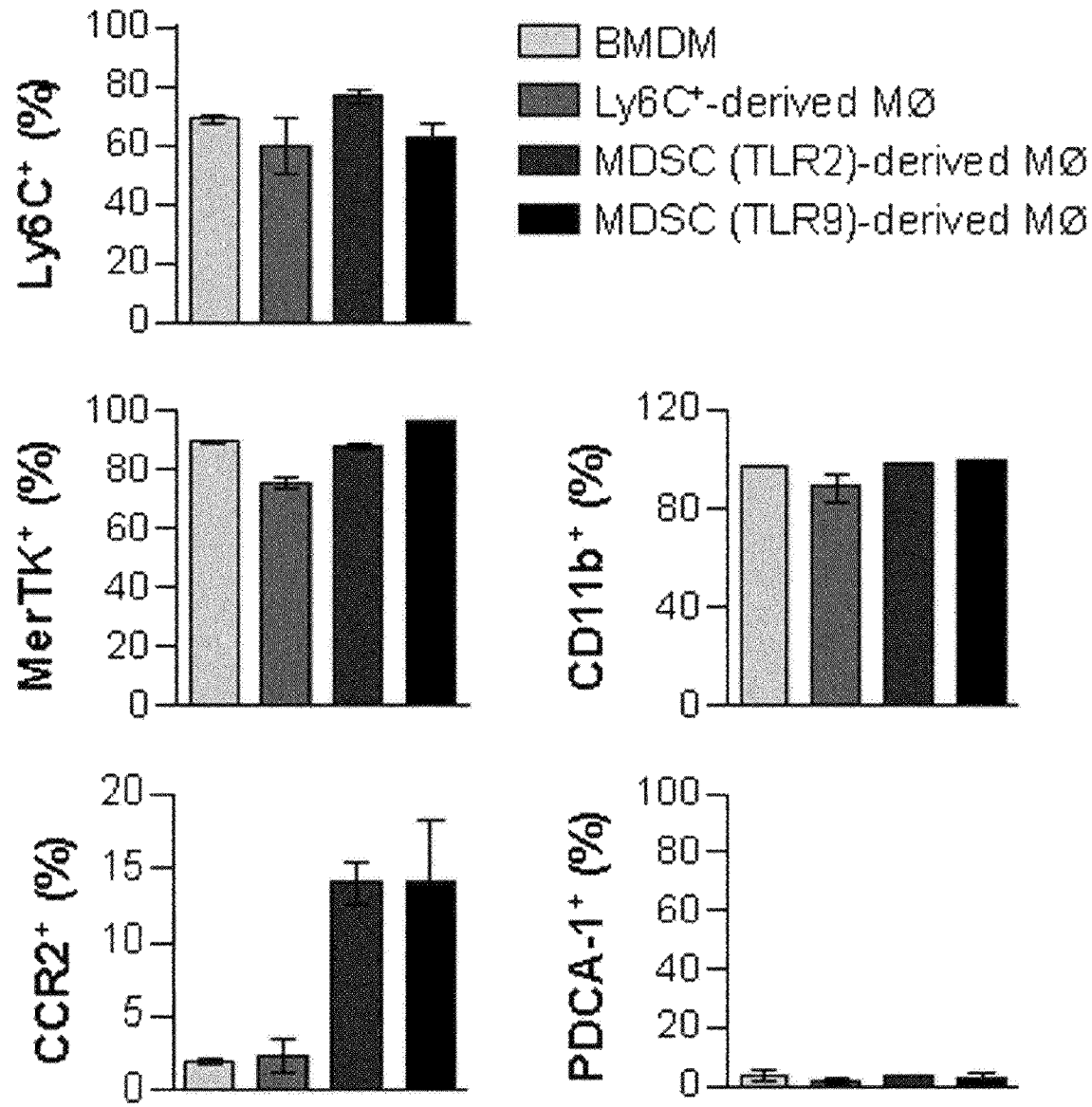

[FIG. 42]
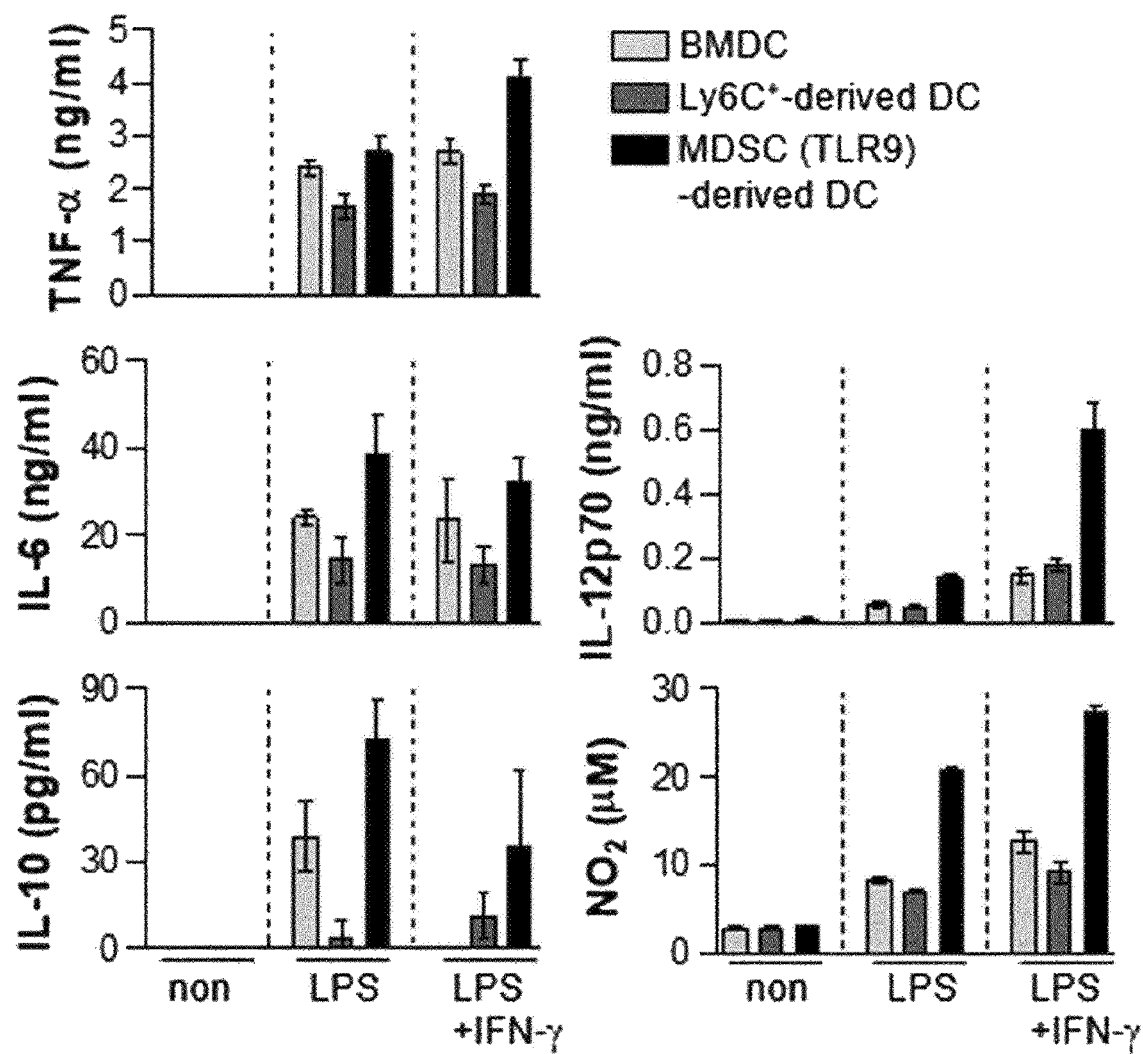

[FIG. 43]
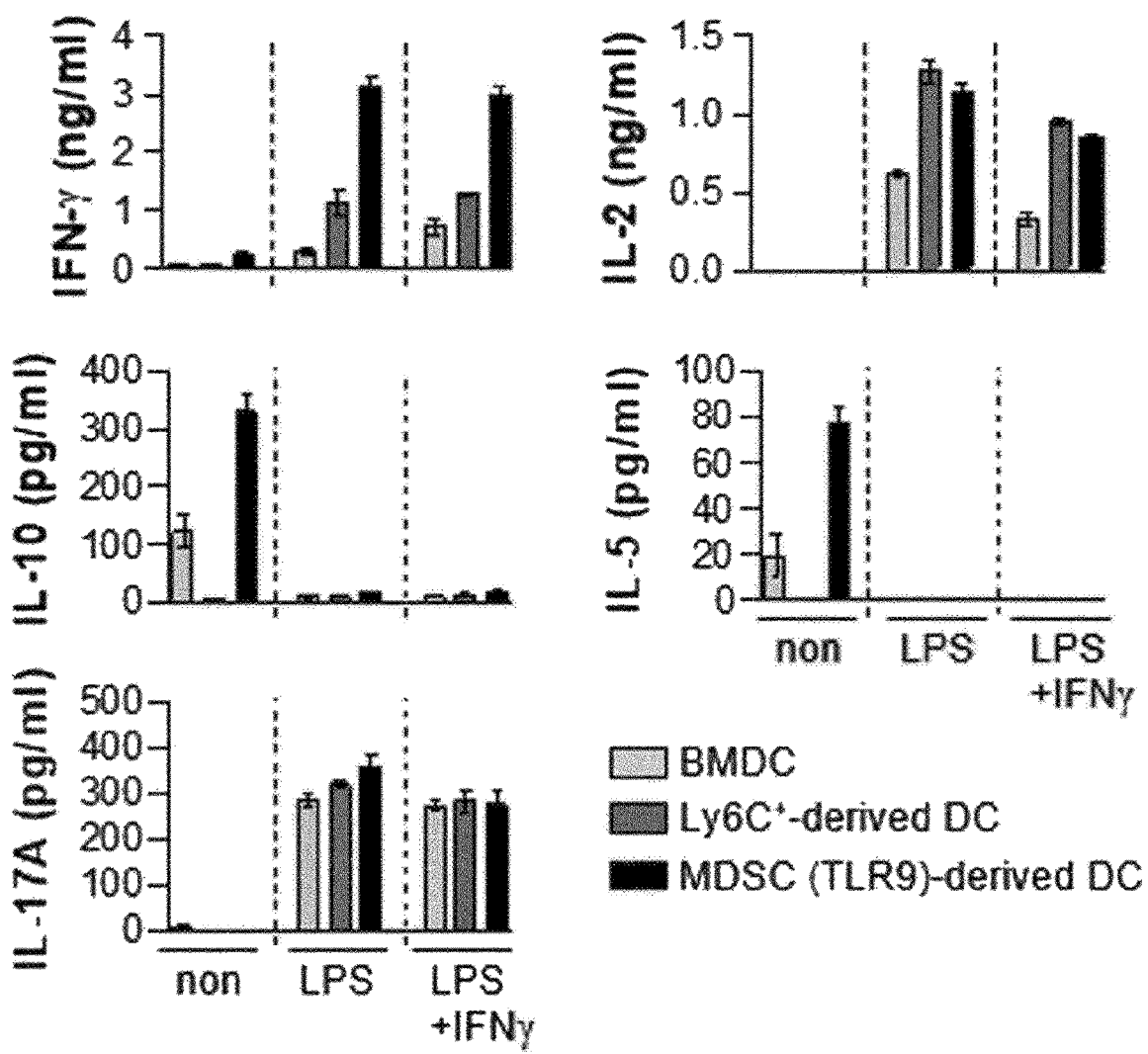

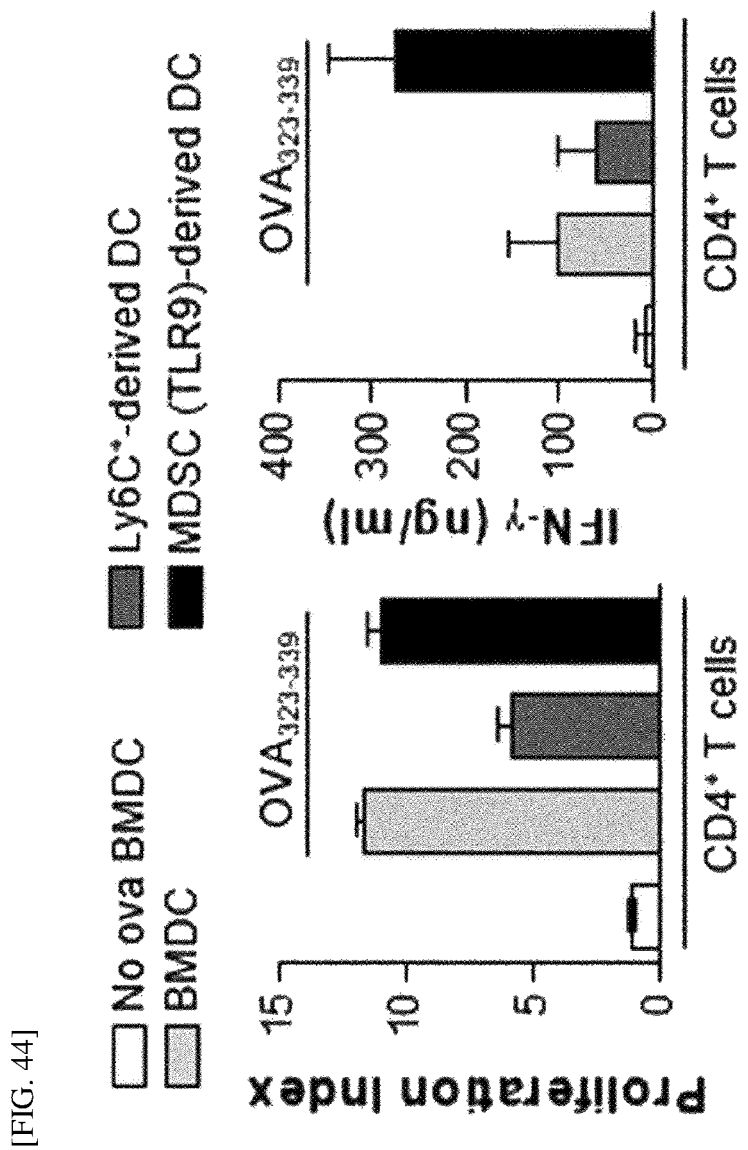
[FIG. 44]

[FIG. 45]
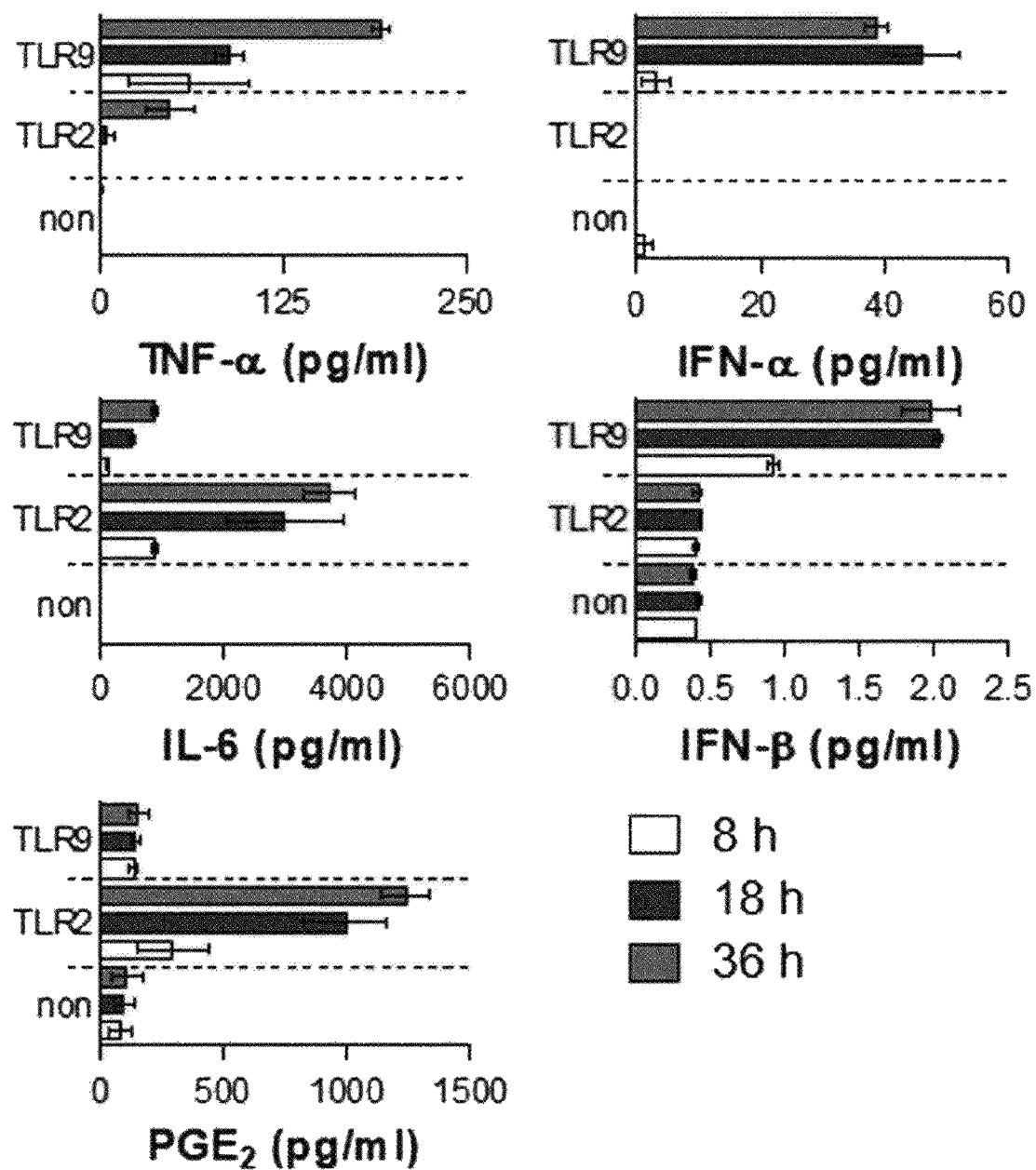

[FIG. 46]
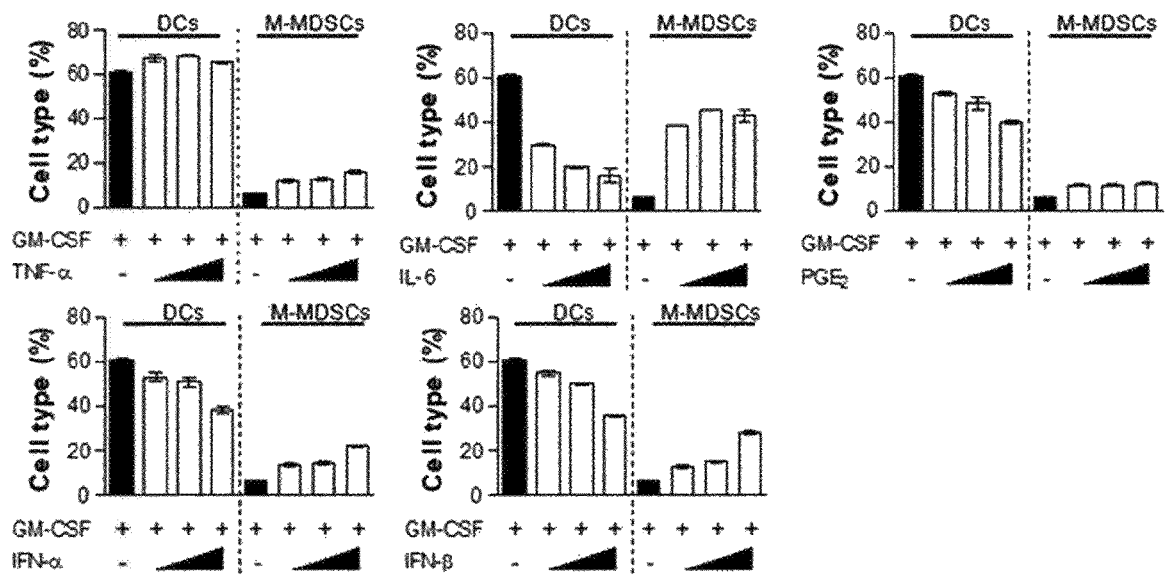
[FIG. 47]
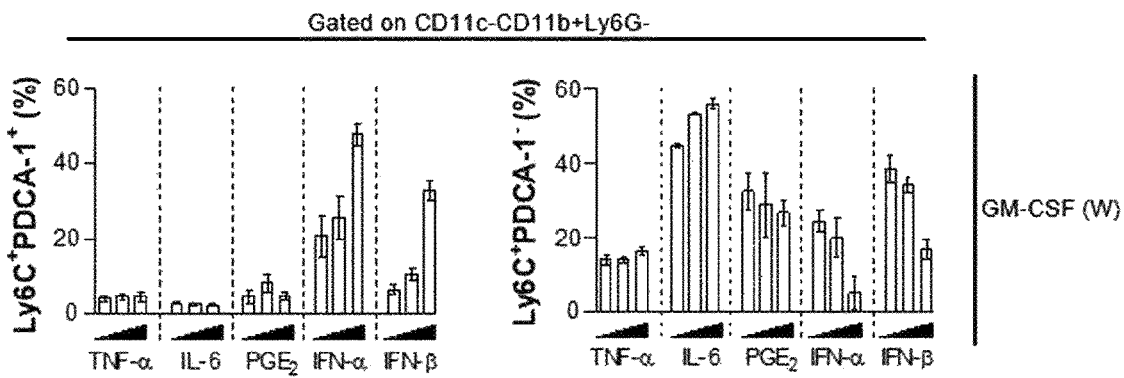

[FIG. 48]
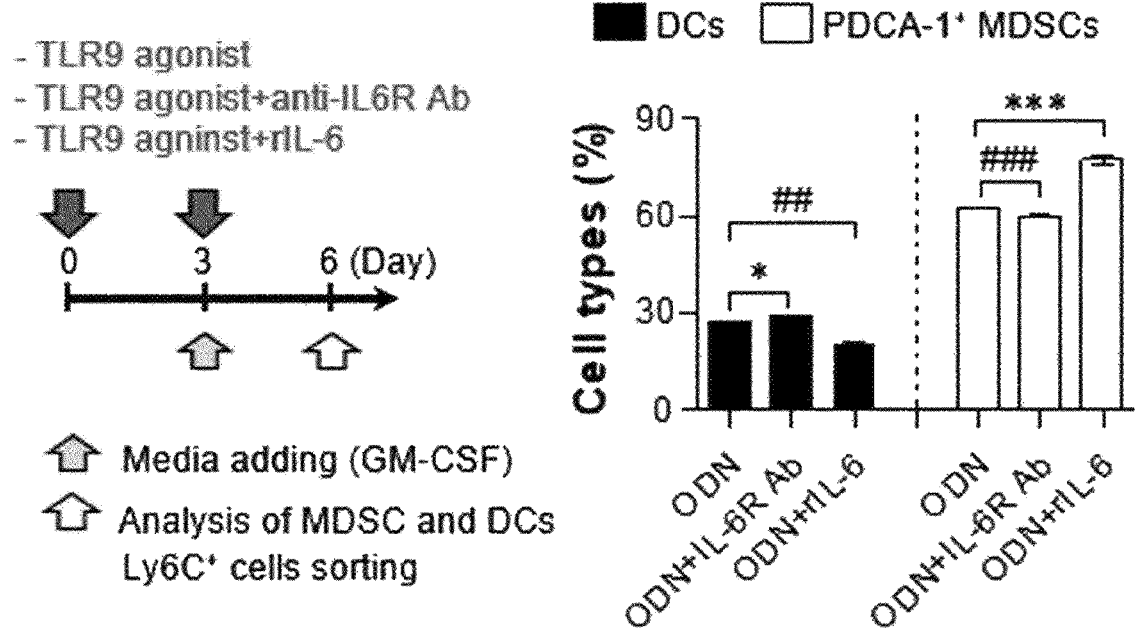
[FIG. 49]
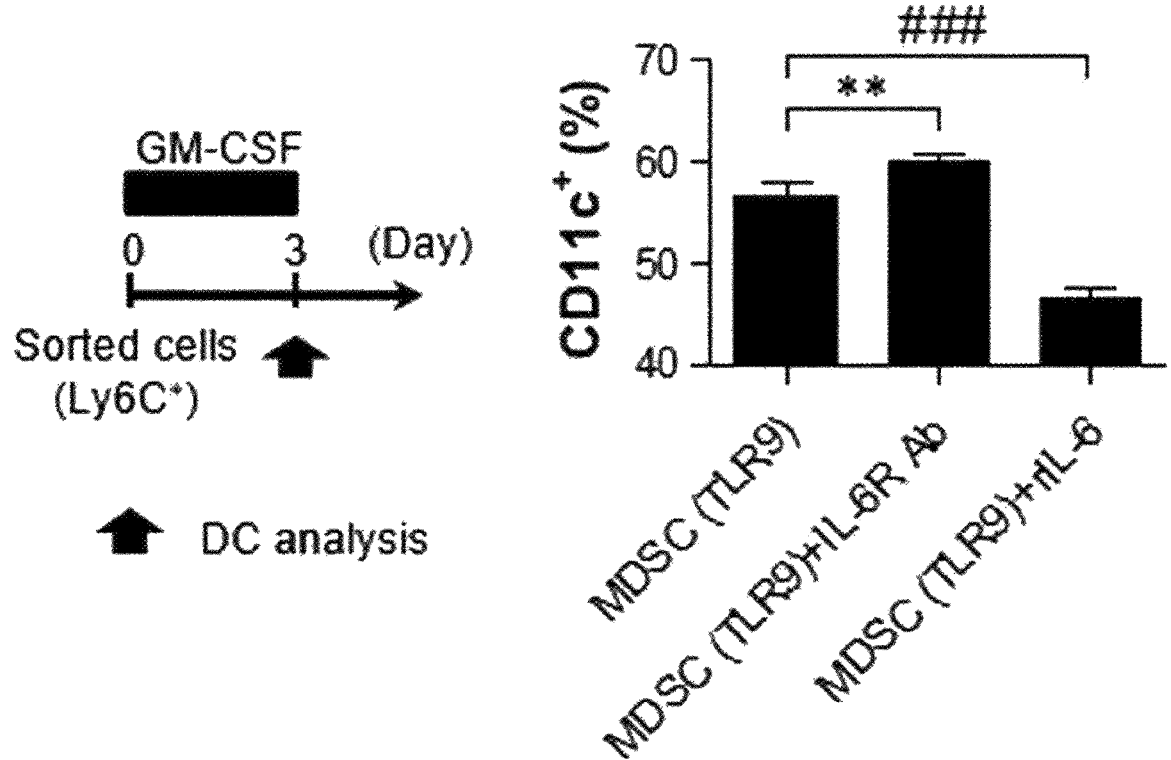

[FIG. 50]
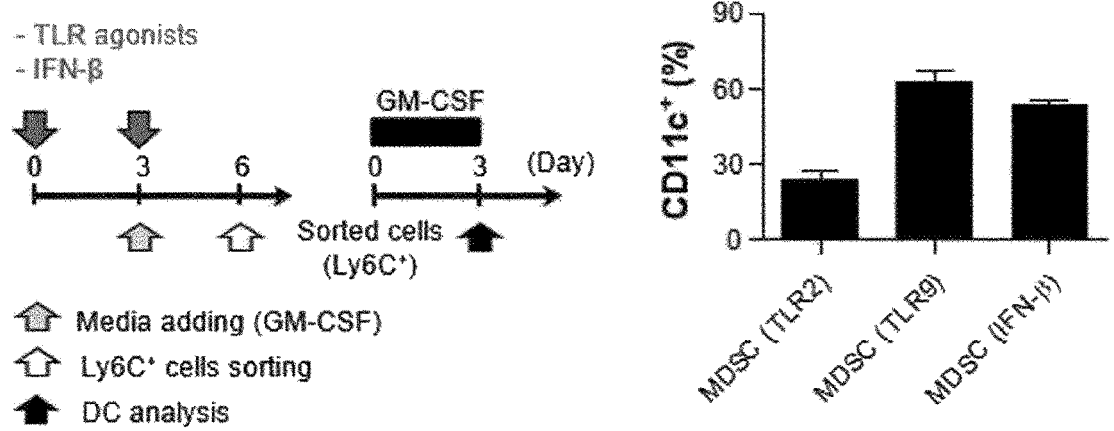
[FIG. 51]
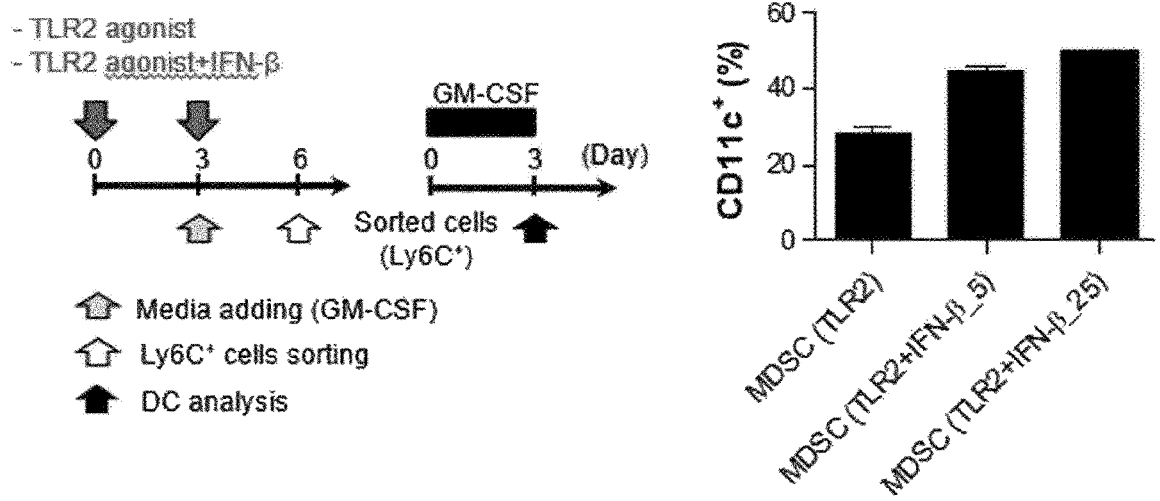
[FIG. 52]
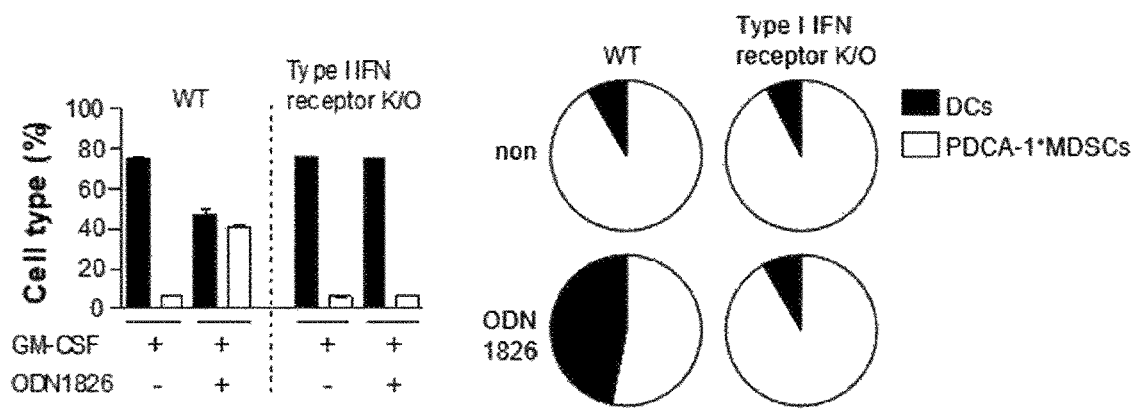

METHOD FOR PRODUCING MYELOID-DERIVED SUPPRESSOR CELLS, MYELOID-DERIVED SUPPRESSOR CELLS PRODUCED THEREBY, AND METHODS THEREOF

CROSS-REFERENCE TO RELATED APPLICATIONS

This application is a U.S. national phase application pursuant to 35 U.S.C. § 371 of International Patent Application No. PCT/KR2018/011558 filed Sep. 28, 2018, which claims priority to Korean Patent Application No. 10-2017-0125968, filed on Sep. 28, 2017, Korean Patent Application No. 10-2017-0125990, filed on Sep. 28, 2017, Korean Patent Application No. 10-2017-0126379, filed on Sep. 28, 2017, the disclosures of which are incorporated herein by reference in its entirety.

TECHNICAL FIELD

The present invention relates to a method for producing myeloid-derived suppressor cells, a myeloid-derived suppressor cell produced thereby, and uses thereof. In addition, the present invention relates to a method for producing dendritic cells, a dendritic cell produced thereby, and uses thereof.

BACKGROUND ART 20 years ago, it was reported that myeloid-derived suppressor cells (MDSCs) are increased in an animal model for which cancer has been caused; and the MDSCs have been known to affect progression and metastasis of cancer. Recently, these cells have been evaluated to play a functionally important role in immune responses. One of the immune suppression mechanisms induced by cancer cells is that myeloid-derived suppressor cells, which are cells having the myeloid lineage phenotype $CD11b^+Gr-1^+$, are increased by cancer. MDSCs are immature myeloid-lineage cells, and exist in an immature state in tumors, autoimmune diseases, and infections because such cells do not completely differentiate into granulocytes or the like. These MDSCs are known to increase in patients with cancer as well as acute inflammatory diseases, trauma, sepsis, and parasite and fungal infections.

The function of the aforementioned MDSCs is to effectively inhibit activated T cells. Regarding the mechanism by which MDSCs regulate T cells, it is known that nitric oxide synthase, reactive oxygen species (ROS), and an enzyme called arginase maximize the metabolism of L-arginine, an essential amino acid, thereby inhibiting T cell activity. That is, in MDSCs, arginase-1, an enzyme that consumes the essential amino acid arginine, is expressed at a high level, thereby effectively lowering the concentration of arginine in the vicinity thereof. In a case where arginine is present at a low level, T cells which are immune cells do not function properly; iNOS, an enzyme that depends on arginine, no longer produces nitric oxide (NO), an important mediator for immune function; and nitrogen peroxide (NO2), a potent toxic oxidizing substance that suppresses immunity, is produced to cause oxidative damage to cell membrane phospholipids in macrophages and other cell systems. Therefore, it is known that MDSCs inhibit the proliferation of T lymphocytes through arginase and NOS activation and inhibit the function of T lymphocytes through formation of ROS.

MDSCs are a set of heterogeneous populations that commonly express the cell surface antigens, CD11b and Gr-1, but differ in expression levels thereof. Gr-1 has two antigenic determinants, Ly-6G and Ly-6C, and thus is divided into granulocytic MDSCs having $CD11b^+Ly-6G^+Ly-6C^{low}$ and monocytic MDSCs having $CD11b^+Ly-6G^-Ly-6C^{hi}$. It is known that in cancer patients, the granulocytic MDSCs account for 70% to 80% and the monocytic MDSCs account for 20% to 30%. The two MDSCs inhibit T cells with different inhibitory mechanisms. The granulocytic MDSCs show high ROS expression and the monocytic MDSCs show high NO production.

Recent studies have reported that MDSCs inhibit the function of CD8 T cells, which are important for the immune function of killing cancer cells or virus-infected cells, and that even in inflammatory responses and septic diseases, MDSCs are increased to exhibit an immunosuppressive function. However, studies on the cytological properties and cell differentiation induction mechanism of these cells are insufficient.

Meanwhile, dendritic cells are potent professional antigen presenting cells (APCs) and play an important role in immune induction and immune regulation in the body.

Dendritic cells in the human body are immune cells that are only 0.3% of the total white blood cells but are capable of activating naive T cells, which have never contacted any antigen, to induce a primary immune response, and to induce antigen-specific acquired memory immunity. The reason why the dendritic cells can serve as potent professional antigen presenting cells is that major histocompatibility complex (MHC) I/II as well as co-stimulatory molecules, such as CD80 and CD86, and adhesion molecules such as ICAM-1 are highly expressed on the cell surface, and these cells secrete large amounts of various cytokines (interferon, IL-12, IL-18, and the like) associated with T cell activation.

As such, since dendritic cells can effectively induce or regulate antigen-specific T cell activity, the possibility that these cells are used as a therapeutic agent for cancer or intractable immune diseases has been studied for a long time. It has been found that in a case where dendritic cells isolated directly from tissue or blood, or dendritic cells differentiated from monocytes are primed by antigens, and then the matured dendritic cells are injected back into the body, potent antigen-specific cytotoxic T lymphocytes (CTLs) are induced. Therefore, the possibility that dendritic cells are developed as a vaccine for treatment of cancer or an infectious disease has long been examined (Inaba, K. et al., 3. Exp. Med., 178:479, 1993; Inaba, K. et al., Int. Rev. Immunol., 6:197, 1990; Hsu, F. et al., Nature Med., 2:52, 1996).

Based on the results of these early studies, clinical studies using dendritic cell therapeutic agents for treatment of cancer are actively conducted around the world, and results have been reported for various carcinomas; however, in a case where such therapeutic agents are used as a monotherapy, clinical effects thereof are still not as expected.

The most important reason why dendritic cell therapeutic agents are not yet successful is due to low immunogenicity of tumor cells and immunosuppressive substances secreted by cancer cells. In this case, if dendritic cells can overcome low immunogenicity of tumor cells by inducing more potent anti-cancer immunity and can induce anti-cancer immunity that may surpass the immunosuppressive capacity of tumor cells, a therapeutic effect thereof may be greatly enhanced.

Technical Problem

An object of the present invention is to provide a method for producing tolerogenic myeloid-derived suppressor cells (MDSCs) from bone marrow cells.

Another object of the present invention is to provide a composition for preventing or treating an immune disease, comprising the tolerogenic myeloid-derived suppressor cell produced in the present invention.

Yet another object of the present invention is to provide a method for producing myeloid-derived suppressor cells (MDSCs) capable of inducing immunogenic dendritic cells (DCs).

Still yet another object of the present invention is to provide a method for producing immunogenic dendritic cells capable of inducing differentiation of naive T cells into Th1 cells.

Still yet another object of the present invention is to provide an immunotherapeutic agent, an antitumor vaccine, or a pharmaceutical composition for treating a tumor, comprising the dendritic cell produced in the present invention.

Other objects and advantages of the present invention will become more apparent from the following detailed description, appended claims, and accompanying drawings.

Solution to Problem

Induction of Tolerogenic Monocytic Myeloid-Derived Suppressor Cells (M-MDSCs) Using Toll-Like Receptor Agonist (TLR Agonist)

The present inventors have discovered that in a case where bone marrow cells are treated with a toll-like receptor agonist (TLR agonist), stable tolerogenic monocytic myeloid-derived suppressor cells (M-MDSCs) are induced which do not undergo further differentiation even in a case of being treated with a growth factor; and thus have arrived at the present invention.

According to an embodiment of the present invention, there is provided a method for producing myeloid-derived suppressor cells (MDSCs), comprising a step of treating bone marrow cells with a toll-like receptor agonist (TLR agonist), to induce differentiation into myeloid-derived suppressor cells.

As used herein, the term "toll-like receptor agonist" may refer to a conserved molecular substance derived from a pathogen, such as pathogen associated molecular patterns (PAMPs). Here, examples of the pathogen may include Gram-positive bacteria, Gram-negative bacteria, fungi, and viruses. In addition, the toll-like receptor agonist may include endogenous molecules released from damaged or dead cells, such as damage associated molecular patterns (DAMPs). PAMPs or DAMPs recruit adapter molecules in the cytoplasm of cells so as to initiate immune responses via TLR signals and transduce signals. The toll-like receptor agonist may include fragments, variants, analogs, homologs, and derivatives of PAMPs or DAMPs which bind to a toll-like receptor and induce TLR-mediated activation such as activation of NF-κB activity. The fragments, variants, analogs, homologs, and derivatives, which are toll-like receptor agonists, are at least 30% to 99% identical to the amino acids of a TLR agonist and induce toll-like receptor-mediated activation.

In the present invention, the toll-like receptor agonist used to treat the bone marrow cells is an agonist of a toll-like receptor (exogenous toll-like receptor) present in the plasma membrane and is preferably at least one of toll-like receptor 2 agonist or toll-like receptor 4 agonist for inducing differentiation into stable tolerogenic myeloid-derived suppressor cells having desired properties in the present invention.

Further, in the present invention, in a case where the bone marrow cells are treated with an agonist of a toll-like receptor (intracellular toll-like receptor) present inside the cell, in particular, in the endolysosomal compartment, for example, with at least one of toll-like receptor 7 agonist or toll-like receptor 9 agonist, combined treatment with interleukin 6 may induce differentiation into stable tolerogenic myeloid-derived suppressor cells as desired in the present invention.

As used herein, the term "toll-like receptor 2 (TLR2)" refers to a substance that is located on the surface of cells such as monocytes, macrophages, and neutrophils, and serves as a receptor for bacterial components (lipopolysaccharide, peptidoglycan, adipocyte protein, acid-fast *bacillus* glycolipid, and the like) and heat shock proteins (HSPs). In a case where TLR2 is stimulated, cells are activated to promote the production of inflammatory cytokines and inflammatory mediators (TNF, IL-1, IL-6, IL-8, NO, and the like).

In the present invention, the toll-like receptor 2 agonist may be, but is not limited to, at least one selected from the group consisting of peptidoglycan or lipoteichoic acid of Gram-positive bacteria; lipoarabinomannan (LAM) of Mycobacteria; lipopeptides of *Mycoplasma*; fungal-derived zymosan, glucuronoxylomannan, or phospholipomannan; porin of *Neisseria*; lipopolysaccharide of Leptospira; biglycan; carboxyalkylpyrrole; endoplasmin; high mobility group box-1 protein (HMGB1); HSP60; HSP70; human cardiac myosin; hyaluronan; monosodium urate crystals; pancreatic adenocarcinoma upregulated factor (PAUF); versican; and Pam3CSK4.

The toll-like receptor 2 agonist used in the present invention is not particularly limited to the above-mentioned types, and any substance may be used without limitation as long as the substance binds to toll-like receptor 2 and stimulates an immune response of toll-like receptor 2.

As used herein, the term "toll-like receptor 4 (TLR4)" refers to a receptor that was first identified in the TLR family and activates innate immune signaling amplified through myeloid differentiation 88 (MyD88)-dependent signaling pathway and MyD88-independent signaling pathway. Toll-like receptor 4, activated by a toll-like receptor 4 agonist, induces initial activation of nuclear factor kappa-light-chain-enhancer of activated B cells (NFκB) and its migration to the nucleus via MyD88-dependent signaling pathway, and induces activation of mitogen-activated protein kinases (MAPKs). Such activation of NFκB and MAPKs secretes inflammatory cytokines such as tumor necrosis factor α (TNF-α), interleukin 1β (IL-1β), and interleukin 6 (IL-6). The MyD88-independent signaling pathway is induced by activation of TRAM/TRW, interferon-regulatory factors (IRFs), and NFκB, thereby secreting type 1 interferon.

In the present invention, the toll-like receptor 4 agonist may be, but is not limited to, at least one selected from the group consisting of lipopolysaccharide of Gram-negative bacteria; mannan of *Candida albicans*; envelope protein of Rous sarcoma virus (RSV) or mouse mammary tumor virus (MMTV); glycoinositol phospholipids of *Trypanosoma*; biglycan; CD138; α-crystallin A chain; β-defensin 2; endoplasmin; fibrinogen; fibronectin; heparan sulfate; HMGB1; HSP22; HSP60; HSP70; HSP72; hyaluronan; monosodium urate crystals; oxidized phospholipids (OxPAPC); pancreatic adenocarcinoma upregulated factor (PAUF); peroxiredoxin 1 (Prx1); resistin; S100 proteins; serum amyloid A3; Taxol/Paclitaxel; lipid A; and monophosphoryl lipid A (MPL).

As used herein, the term "toll-like receptor 7 (TLR7)" refers to one of the factors that constitute the sensing system in innate immunity. The TLR7 protein is embedded in the cellular membrane and responds only to a specific stimulus. Once TLR7 acquires activity through a specific stimulus, the pathway that triggers the defense mechanism of the immune system begins to work in its full extent. The main agonist of TLR7 is imiquimod which is a biochemical agent that induces stimulation of TLR7 activity. Imiquimod, an immune agonist approved by the US Food and Drug Administration on Feb. 27, 1997, is used as an antiviral agent and is mainly used for external skin application.

In the present invention, the toll-like receptor 7 agonist may be, but is not limited thereto, at least one selected from the group consisting of imiquimod, imidazoquinolines, GS-9620, GSK-2245035, resiquimod, DSR-6434, DSP-3025, IMO-4200, MCT-465, 3M-051, SB-9922, 3M-052, rimtop, TMX-30X, TMX-202, RG-7863, RG-7795, R848, 7-thia-8-oxoguanosine, 7-deazaguanosine, 7-allyl-8-oxoguanosine, and 7-dezaguanosine.

In the present invention, as the toll-like receptor 7 agonist, various toll-like receptor 7 agonists may be used without limitation which are described in US Patent Application Publication No. 2012-0294885, WO 2012/066335, WO 2012/066336, WO 2015/168279, WO 2015/168269, and the like.

However, the toll-like receptor 7 agonist used in the present invention is not particularly limited to the above-mentioned types, and any substance may be used without limitation as long as the substance binds to toll-like receptor 7 and stimulates an immune response of TLR7.

As used herein, the term "toll-like receptor 9 (TLR9)" refers to a protein of the toll-like receptor (TLR) family which plays a fundamental role in pathogen recognition and activation of innate immunity. TLR9 is found mainly in the endosomal compartment of B cells, monocytes, macrophages and plasmacytoid dendritic cells (Galluzzi et al., OncoImmunology, 1:5, (2012) 699-716). The main agonist of TLR9 is bacterial or viral DNA having a higher frequency of unmethylated CpG oligodeoxynucleotides than its mammalian counterpart. The CpG oligodeoxynucleotide (or CpG ODN) is a short single-stranded synthetic DNA molecule that contains cytidine triphosphate deoxynucleotide ("C") followed by guanidine triphosphate deoxynucleotide ("G"). "p" refers to a phosphodiester linkage between consecutive nucleotides, although some ODNs have a modified phosphorothioate (PS) backbone. In a case where these CpG motifs are unmethylated, they bind to toll-like receptor 9 and stimulate an immune response of TLR9 (Weiner, G J; et al, PNAS 94 (1997) 10833-7).

In the present invention, the toll-like receptor 9 agonist may be an oligodeoxynucleotide (CpG ODN) containing an unmethylated cytosine-phosphate-guanosine (CpG) motif, and may also include various variants thereof. In the present invention, the toll-like receptor 9 agonist may be an oligodeoxynucleotide containing a motif selected from the group consisting of CpG, C*pG, CpG*, and C*pG*, and may be preferably an oligodeoxynucleotide containing a CpG motif.

Here, C may be 2'-deoxycytidine and C* may be an analog thereof; G may be 2'-deoxyguanosine and G* may be an analog thereof; and p may be an internucleoside linkage selected from the group consisting of phosphodiester, phosphorothioate, and phosphorodithioate. In the present invention, C* may be selected from, but is not limited to, the group consisting of 2'-deoxythymidine, arabinocytidine, 2'-deoxythymidine, 2'-deoxy-2'-substituted arabinocytidine, 2'-O-substituted arabinocytidine, 2'-deoxy-5-hydroxycytidine, 2'-deoxy-N4-alkyl-cytidine, and 2'-deoxy-4-thiouridine. In the present invention, G* may be, but is not limited to, 2'-deoxy-7-deazaguanosine, 2'-deoxy-6-thioguanosine, arabinoguanosine, 2'-deoxy-2'-substituted arabinoguanosine, 2'-O-substituted arabinoguanosine, and 2'-deoxyinosine.

In the present invention, the CpG ODNs may be classified into classes A (or "D"), B (or "K"), and C, which differ in immuno-stimulatory activity (Krug A. et al., 2001, Eur J Immunol, 31(7): 2154-63). Class A CpG ODN is a potent stimulator for natural killer cells and induces secretion of alpha-interferon from pDCs; class B CpG ODN is a potent stimulator for B cells and dendritic cells; and class C CpG ODN has both characteristics of class A and class B (Klinman, Nat Rev Immunol 2004; 4: 249-59; Krieg Curr Oncol Rep 2004; 6: 88-95).

In the present invention, the class A CpG ODN (Xueqing Liang, et al, Blood. 2010 Jun. 17; 115 (24): 5041-5052) may be selected from, but is not limited to, the group consisting of CpG ODN 2216, CpG ODN 1585, CpG ODN 2336, CpG ODN PB4, and CpG ODN 1002.

In the present invention, the class B CpG ODN may be selected from, but is not limited to, the group consisting of CpG ODN 1668, CpG ODN 1826, CpG ODN 2006, CpG ODN 2007, CpG ODN BW006, CpG ODN D-SL01, CpG-28, CpG-685 (GNKG168; CpG ODN; manufactured by SBI Biotech Co., Ltd.), CpG-684, and CpG-7909 (CPG-ODN 2006, PF-3512676, Agatolimod).

In the present invention, the class C CpG ODN may be selected from, but is not limited to, the group consisting of CpG ODN 2395, CpG ODN M362, and CpG ODN D-SL03.

In the present invention, the toll-like receptor 9 agonist may be, but is not limited to, IMO-2055 (manufactured by Idera Pharmaceuticals) (ODN composed of 3'-3'-linked structure and synthetic CpR (R=2'-deoxy-7-deazaguanosine) motif).

In addition, in the present invention, the toll-like receptor 9 agonist may be, but is not limited to, an oligodeoxynucleotide based on CpG motif-containing circular ODN (for example, MGN-1703, manufactured by MOLOGEN AG, as described in WO 2012/085291), the CpG motif-containing circular ODN being produced based on the dSLIM (registered trademark) technology (which is described in WO 2001/07055).

In addition, in the present invention, the toll-like receptor 9 agonist may be, but is not limited to, a naturally-occurring agonist which is described in Smith & Wickstrom (1998) J. Natl. Cancer Inst. 90:1146-1154.

In the present invention, as the toll-like receptor 9 agonist, various toll-like receptor 9 agonists may be used without limitation which are described in US Patent Application Publication No. 2009/0053206, US Patent Application Publication No. 2008/0292648, US Patent Application Publication No. 2007/0105800, US Patent Application Publication No. 2010/0016250, US Patent Application Publication No. 2009/0041809, WO 2007/7047396, WO 2007/7047396, WO 2010/088395, WO 2003/035695, WO 2012/085291, WO 1998/018810, WO 2005/042018, WO 2008/073959, WO 2009/018431, WO 2007/084237, and the like. In addition, as the toll-like receptor 9 agonist, the selective toll-like receptor 9 agonists, IMO-2055, IMO-2125, and IMO-2134 (manufactured by Idera Pharmaceuticals) which are undergoing phase 1/phase 2 clinical trials, may also be used. However, the toll-like receptor 9 agonist is not limited thereto.

The toll-like receptor 9 agonist used in the present invention is not particularly limited to the above-mentioned types, and any substance may be used without limitation as long as the substance binds to toll-like receptor 9 and stimulates an immune response of toll-like receptor 9.

In the present invention, the toll-like receptor agonist may be applied in an amount of 10 ng/ml to 1,000 ng/ml, 10 ng/ml to 5,000 ng/ml, or 10 ng/ml to 100 ng/ml. However, the present invention is not limited thereto.

In the present invention, interleukin 6 may be applied in an amount of 1 ng/ml to 100 ng/ml, 1 ng/ml to 50 ng/ml, or 1 ng/ml to 10 ng/ml. However, the present invention is not limited thereto.

In the present invention, the toll-like receptor agonist and interleukin 6, which is optionally applied, may be applied one or more times before initiation of, at the initiation time of, or during bone marrow cell differentiation; and may be preferably applied at the initiation time of bone marrow cell differentiation, and then applied one or more times during the differentiation. However, the present invention is not limited thereto.

In the present invention, the bone marrow cell differentiation may be carried out by inoculating the bone marrow cells in a medium supplemented with a growth factor and performing culture for 5 to 10 days, 5 to 7 days, or 6 days.

In addition, in the present invention, in a case where the toll-like receptor agonist and interleukin 6, which is optionally applied, are applied before the initiation of bone marrow cell differentiation, the bone marrow cells may be treated with a growth factor within 36 hours, preferably 24 hours, from the time point at which the agonist has been applied, so that the differentiation is initiated. However, the present invention is not limited thereto.

In the present invention, in a case where the toll-like receptor agonist and interleukin 6 are applied at the initiation time of bone marrow cell differentiation, the bone marrow cells may be inoculated and cultured in a medium supplemented with the toll-like receptor agonist, interleukin 6, and a growth factor. However, the present invention is not limited thereto.

In the present invention, in a case where the toll-like receptor agonist and interleukin 6 are applied during bone marrow cell differentiation, the toll-like receptor agonist and interleukin 6 may be applied within 3 days (72 hours) or 5 days (120 hours) from the initiation time of bone marrow cell differentiation. However, the present invention is not limited thereto.

As used herein, the term "initiation of differentiation" may refer to a process in which a growth factor is added to a culture medium of bone marrow cells, or bone marrow cells are inoculated in a medium supplemented with a growth factor, and culture is performed. The process is not particularly limited as long as such a process can induce differentiation of bone marrow cells using a growth factor.

In the present invention, the growth factor is a stimulant of bone marrow cells, and may be preferably at least one selected from the group consisting of granulocyte-macrophage colony stimulating factor (GM-CSF), granulocyte colony stimulating factor (G-CSF), macrophage colony stimulating factor (M-CSF), stem cell factor (SCF), FMS-like tyrosine kinase 3 (Flt3), and interleukin 3 (IL-3), with granulocyte-macrophage colony stimulating factor (GM-CSF) being more preferred.

In the present invention, the growth factor may be applied in an amount of 10 ng/ml to 500 ng/ml, 10 ng/ml to 100 ng/ml, or 10 ng/ml to 50 ng/ml. However, the present invention is not limited thereto.

In the present invention, in a case where at least one of toll-like receptor 2 agonist or toll-like receptor 4 agonist is applied at the initiation time of and during bone marrow cell differentiation using the growth factor, monocytic myeloid-derived suppressor cells (M-MDSCs) having the cellular phenotype $CD11c^-CD11b^+Ly6G^-Ly6C^{int}PDCA-1^-$ may be induced from the bone marrow cells.

In addition, in the present invention, in a case where at least one of toll-like receptor 7 agonist or toll-like receptor 9 agonist is applied in combination with interleukin 6 at the initiation time of and during bone marrow cell differentiation using the growth factor, monocytic myeloid-derived suppressor cells having the phenotype $CD11c^-CD11b^+Ly6G^-\ Ly6C^+PDCA-1^+$ may be induced from the bone marrow cells.

In the present invention, the monocytic myeloid-derived suppressor cells obtained as described above have immunogenic characteristics from the viewpoint of inhibiting expression of inflammatory cytokines and IFN-γ and inhibiting activity of T cells.

In addition, in the present invention, both monocytic myeloid-derived suppressor cells obtained as described above, that is, the monocytic myeloid-derived suppressor cells induced by treatment of bone marrow cells with a toll-like receptor 2 agonist or a toll-like receptor 4 agonist, and the monocytic myeloid-derived suppressor cells induced by treatment of bone marrow cells with a toll-like receptor 7 agonist or a toll-like receptor 9 agonist in combination with interleukin 6 may stably maintain the characteristics of monocytic myeloid-derived suppressor cells without being induced to differentiate into dendritic cells even in a case of being further treated with a growth factor.

According to another embodiment of the present invention, there is provided a composition for inducing differentiation into myeloid-derived suppressor cells, comprising a toll-like receptor agonist.

In the present invention, in a case where bone marrow cells are treated with the composition, the bone marrow cells may be induced into tolerogenic myeloid-derived suppressor cells.

In the present invention, the toll-like receptor agonist is an agonist of a toll-like receptor (exogenous toll-like receptor) present in the plasma membrane and is preferably at least one of toll-like receptor 2 agonist or toll-like receptor 4 agonist because these toll-like receptor agonists are capable of inducing differentiation into stable tolerogenic myeloid-derived suppressor cells having desired properties in the present invention.

Further, in the present invention, as the toll-like receptor agonist, an agonist of a toll-like receptor (intracellular toll-like receptor) present inside the cell, in particular, in the endolysosomal compartment, for example, at least one of toll-like receptor 7 agonist or toll-like receptor 9 agonist may be used. In this case, however, the composition must also comprise interleukin 6 as an essential ingredient so that bone marrow cells can be induced to differentiate into stable tolerogenic myeloid-derived suppressor cells as desired in the present invention.

In the present invention, specific types of the toll-like receptor agonist overlap with those described for the method for producing myeloid-derived suppressor cells, and thus the description thereof is omitted below to avoid excessive complexity of the specification.

In the present invention, the toll-like receptor agonist may be contained in an amount of 10 ng/ml to 1,000 ng/ml, 10 ng/ml to 5,000 ng/ml, or 10 ng/ml to 100 ng/ml. However, the present invention is not limited thereto.

In the present invention, interleukin 6 may be contained in an amount of 1 ng/ml to 100 ng/ml, 1 ng/ml to 50 ng/ml, or 1 ng/ml to 10 ng/ml. However, the present invention is not limited thereto.

In the present invention, a composition comprising the toll-like receptor agonist and, optionally, interleukin 6 may be applied one or more times before initiation of, at the initiation time of, or during bone marrow cell differentiation; and may be preferably applied at the initiation time of bone marrow cell differentiation, and then applied one or more times during the differentiation. However, the present invention is not limited thereto.

In a case where the composition of the present invention is applied at the initiation time of bone marrow cell differentiation, the composition of the present invention may further contain a growth factor as a stimulant of bone marrow cells to induce differentiation of the bone marrow cells. In the present invention, the growth factor may be at least one selected from the group consisting of granulocyte-macrophage colony stimulating factor (GM-CSF), granulocyte colony stimulating factor (G-CSF), macrophage colony stimulating factor (M-CSF), stem cell factor (SCF), FMS-like tyrosine kinase 3 (Flt3), and interleukin 3 (IL-3), with granulocyte-macrophage colony stimulating factor (GM-CSF) being more preferred.

In the present invention, the growth factor may be contained in an amount of 10 ng/ml to 500 ng/ml, 10 ng/ml to 100 ng/ml, or 10 ng/ml to 50 ng/ml. However, the present invention is not limited thereto.

In the present invention, in a case where bone marrow cells are treated with a toll-like receptor 2 agonist or a toll-like receptor 4 agonist in the form of the composition of the present invention, monocytic myeloid-derived suppressor cells (M-MDSCs) having the cellular phenotype $CD11c^-CD11b^+Ly6G^-Ly6C^{int}PDCA-1^-$ may be induced from the bone marrow cells.

In addition, in the present invention, in a case where bone marrow cells are treated with at least one of toll-like receptor 7 agonist or toll-like receptor 9 agonist in combination with interleukin 6 in the form of the composition of the present invention, monocytic myeloid-derived suppressor cells having $CD11c^-CD11b^+Ly6G^-Ly6C^+PDCA-1^+$ may be induced from the bone marrow cells.

In the present invention, the monocytic myeloid-derived suppressor cells obtained as described above have immunogenic characteristics from the viewpoint of inhibiting expression of inflammatory cytokines and IFN-γ and inhibiting activity of T cells.

In addition, the monocytic myeloid-derived suppressor cells induced in the present invention may stably maintain the characteristics of monocytic myeloid-derived suppressor cells without being induced to differentiate into dendritic cells even in a case of being further treated with a growth factor.

According to yet another embodiment of the present invention, there is provided a pharmaceutical composition for preventing or treating an immune disease, comprising, as an active ingredient, the myeloid-derived suppressor cell produced by the method of the present invention.

In the present invention, the immune disease may be graft rejection after organ transplantation, graft rejection after hematopoietic stem cell transplantation, an autoimmune disease, or an allergic disease, which is caused by a hypersensitive immune response.

In the present invention, the "autoimmune disease" is a non-malignant disease or disorder which arises from and is directed against the individual's own tissue. One of the most important characteristics in all normal individuals is that they are capable of recognizing, responding to, and eliminating non-self antigens while not responding harmfully to antigenic substances that make up the self. The living body's unresponsiveness to self-antigens is called immunologic unresponsiveness or tolerance. However, in a case where abnormalities arise in inducing or maintaining self-tolerance, immune responses occur against self antigens, and as a result, a phenomenon in which the self tissue is attacked occurs. The disease caused by this process is called an autoimmune disease. The autoimmune disease is an inflammatory disease in which antibodies are produced against the self organ tissue or components thereof, and may collectively refer to diseases in which chronic systemic inflammation is caused in many tissues and organs.

Specifically, in the present invention, the autoimmune disease may be, but is not limited to, at least one selected from the group consisting of rheumatoid arthritis, systemic lupus erythematosus, septic shock, allergic asthma, allergic rhinitis, atopic dermatitis, ulcerative colitis, dacryoadenitis, Alzheimer's disease, stroke, arteriosclerosis, vascular restenosis, type I diabetes, type II diabetes, urticaria, conjunctivitis, psoriasis, systemic inflammatory response syndrome, polymyositis, dermatomyositis, polyarthritis *nodosa*, mixed connective tissue disease, Sjogren's syndrome, gout, Parkinson's disease, amyotrophic lateral sclerosis, diabetic retinopathy, multiple sclerosis, Crohn's disease, chronic thyroiditis, Celiac disease, myasthenia gravis, pemphigus vulgaris, viral diseases, bacterial diseases, radiation-induced disorders, arteriosclerosis, hemangioma, angiofibroma, reperfusion injury, and cardiac hypertrophy.

As used herein, the term "prevention" refers to any act of inhibiting or delaying progression of an immune disease by administration of the composition of the present invention.

As used herein, the term "treatment" or "improvement" refers to any act of ameliorating or beneficially altering symptoms of an immune disease by administration of the composition of the present invention.

The pharmaceutical composition of the present invention may comprise a therapeutically effective amount of myeloid-derived suppressor cells for treatment of an immune disease. The therapeutically effective amount refers to an amount of an active ingredient or a pharmaceutical composition which induces a biological or medical response in a tissue system, an animal, or a human, considered by researchers, veterinarians, physicians, or other clinicians, and includes an amount that induces alleviation of symptoms of a disease or disorder to be treated. It is apparent to those skilled in the art that the amount (number) of myeloid-derived suppressor cells to be contained in the pharmaceutical composition for preventing or treating an immune disease of the present invention will vary depending on a desired effect. Therefore, an optimal amount of a cell therapeutic agent may be easily determined by those skilled in the art, and may be adjusted depending on various factors including type of disease, severity of disease, amounts of other ingredients contained in the composition, type of formulation, and the patient's age, body weight, general health status, sex, and diet, time of administration, route of administration and excretion rate of the composition, treatment duration, and simultaneously used drugs. For example, the myeloid-derived suppressor cells may be contained in an amount of $2 \times 10^4$ cells/ml to $8 \times 10^7$ cells/ml. However, the present invention is not limited thereto.

In the present invention, the pharmaceutical composition may be in the form of capsules, tablets, granules, injections, ointments, powders, or beverages, and may be intended for humans.

The pharmaceutical composition of the present invention may be formulated in the form of oral preparations such as powders, granules, capsules, tablets, aqueous suspensions, and the like, preparations for external use, suppositories, and sterile injectable solutions, respectively, according to conventional methods, and used. However, the present invention is not limited thereto. The pharmaceutical composition of the present invention may further contain a pharmaceutically acceptable carrier. As the pharmaceutically acceptable carrier, a binder, a glidant, a disintegrant, an excipient, a solubilizer, a dispersant, a stabilizer, a suspending agent, a pigment, a flavor, and the like may be used for oral administration; a buffer, a preserving agent, a pain-relieving agent, a solubilizer, an isotonic agent, a stabilizer, and the like may be used in admixture for injections; and a base, an excipient, a lubricant, a preserving agent, and the like may be used for topical administration. The preparations of the pharmaceutical composition of the present invention may be prepared in various ways by being mixed with the pharmaceutically acceptable carrier as described above. For example, for oral administration, the pharmaceutical composition may be formulated in the form of tablets, troches, capsules, elixirs, suspensions, syrups, wafers, or the like. For injections, the pharmaceutical composition may be formulated in the form of unit dosage ampoules or multiple dosage forms. Alternatively, the pharmaceutical composition may be formulated into solutions, suspensions, tablets, capsules, sustained-release preparations, or the like.

Meanwhile, as examples of carriers, excipients, or diluents suitable for making preparations, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, or the like may be used. In addition, a filler, an anti-coagulant, a lubricant, a wetting agent, a flavor, an emulsifier, a preservative, and the like may further be included.

The route of administration of the pharmaceutical composition according to the present invention includes, but is not limited to, oral, intravenous, intramuscular, intraarterial, intramedullary, intradural, intracardiac, transdermal, subcutaneous, intraperitoneal, intranasal, intestinal, topical, sublingual, or rectal route. Oral or parenteral administration is preferred.

In the present invention, the "parenteral" includes subcutaneous, intradermal, intravenous, intramuscular, intraarticular, intrabursal, intrasternal, intradural, intralesional, and intracranial injection or infusion techniques. The pharmaceutical composition of the present invention may also be administered in the form of suppositories for rectal administration.

The pharmaceutical composition of the present invention may vary depending on a variety of factors, including activity of a certain compound used, the patient's age, body weight, general health status, sex, diet, time of administration, route of administration, rate of excretion, drug combination, and severity of a certain disease to be prevented or treated. A dose of the pharmaceutical composition may vary depending on the patient's condition, body weight, severity of disease, drug form, route of administration, and duration, and may be appropriately selected by those skilled in the art.

The pharmaceutical composition may be administered in an amount of 0.0001 to 50 mg/kg or 0.001 to 50 mg/kg, per day. Administration may be made once a day or several times a day. The dose is not intended to limit the scope of the invention in any way. The pharmaceutical composition according to the present invention may be formulated in the form of pills, sugar-coated tablets, capsules, liquids, gels, syrups, slurries, or suspensions.

The composition of the present invention may be used alone or in admixture with a conventional therapeutic agent for an autoimmune disease, for example, methotrexate (MTX) that is a therapeutic agent for rheumatoid arthritis, and the like, or may be used in combination with surgery, radiation therapy, hormone therapy, chemotherapy, and methods in which a bological response modifier is used.

According to still yet another embodiment of the present invention, there is provided a method for preparing a cosmetic composition for preventing or improving an autoimmune disease, the composition comprising, as an active ingredient, the myeloid-derived suppressor cell according to the present invention.

In the present invention, detailed description of the method for producing myeloid-derived suppressor cells overlaps with that described above for the pharmaceutical composition, and thus the description thereof is omitted below to avoid excessive complexity of the specification.

In a case where the myeloid-derived suppressor cells of the present invention are contained in the cosmetic composition, these cells may be added in a cell number of $2\times10^4$ cells/ml to $8\times10^7$ cells/ml. However, the present invention is not limited thereto.

In the present invention, the cosmetic composition may be prepared in the form of skin softeners, nourishing lotions, nourishing essences, massage creams, cosmetic bath water additives, body lotions, body milks, bath oil, baby oil, baby powders, shower gels, shower creams, sun screen lotions, sun screen creams, suntan creams, skin lotions, skin creams, UV blocking cosmetics, cleansing milks, hair removing agents (for cosmetic purposes), face and body lotions, face and body creams, skin whitening creams, hand lotions, hair lotions, cosmetic creams, Jasmine oil, bath soaps, liquid soaps, cosmetic soaps, shampoos, hand cleaners, medicinal soaps (for non-medical purposes), cream soaps, facial washes, body cleansers, scalp cleansers, hair rinses, toilet soaps, tooth whitening gels, toothpastes, and the like. To this end, the composition of the present invention may further contain either a solvent which is conventionally used for the preparation of cosmetic compositions, or a suitable carrier, excipient, or diluent.

The type of solvent that may further be added to the cosmetic composition of the present invention is not particularly limited, and examples of the solvent may include water, saline, DMSO, or a combination thereof. In addition, examples of the carrier, excipient, or diluent include, but are not limited to, purified water, oil, wax, fatty acids, fatty acid alcohol, fatty acid esters, surfactants, humectants, thickeners, antioxidants, viscosity stabilizers, chelating agents, buffers, lower alcohol, and the like. In addition, the cosmetic composition of the present invention may, if necessary, contain whitening agents, moisturizing agents, vitamins, UV blocking agents, fragrances, dyes, antibiotics, antibacterial agents, and antifungal agents.

Examples of the oil may include hydrogenated vegetable oil, castor oil, cottonseed oil, olive oil, palm kernel oil, jojoba oil, and avocado oil, and examples of the wax may include beeswax, spermaceti, carnauba wax, candelilla wax, montan wax, ceresin wax, liquid paraffin, and lanolin.

Examples of the fatty acids may include stearic acid, linoleic acid, linolenic acid, and oleic acid; examples of the fatty acid alcohol may include cetyl alcohol, octyl dodecanol, oleyl alcohol, panthenol, lanolin alcohol, stearyl alcohol, and hexadecanol; and examples of the fatty acid esters may include isopropyl myristate, isopropyl palmitate, and butyl stearate. Examples of the surfactants may include cationic surfactants, anionic surfactants, and nonionic surfactants, which are known in the art. Among these, if possible, surfactants derived from natural products are preferred.

In addition, the cosmetic composition of the present invention may contain humectants, thickeners, antioxidants, and the like, which are widely known in the cosmetic field, and the types and amounts thereof are as known in the art.

According to still yet another embodiment of the present invention, there is provided a method for preparing a food composition for preventing or improving an autoimmune disease, the composition comprising, as an active ingredient, the myeloid-derived suppressor cell according to the present invention.

In the present invention, detailed description of the method for producing myeloid-derived suppressor cells overlaps with that described above for the pharmaceutical composition, and thus the description thereof is omitted below to avoid excessive complexity of the specification.

The food composition of the present invention may be prepared in the form of various foods, for example, beverages, gums, tea, vitamin complexes, powders, granules, tablets, capsules, confections, rice cakes, bread, and the like. The food composition of the present invention is composed of a plant extract having little toxicity and side effects, and thus can be used without worries in a case of being ingested for a long time for preventive purposes.

In a case where the myeloid-derived suppressor cells of the present invention are contained in the food composition, these cells may be added in a cell number of $2 \times 10^4$ cells/ml to $8 \times 10^7$ cells/ml. However, the present invention is not limited thereto.

Here, in a case where the food composition is prepared in the form of beverages, there is no particular limitation except that the beverage contains the food composition at an indicated proportion, and the beverage may contain various flavoring agents, natural carbohydrates, or the like as additional ingredients, similarly to conventional beverages. That is, examples of the natural carbohydrates may include monosaccharides such as glucose, disaccharides such as fructose, polysaccharides such as sucrose, conventional sugars such as dextrin and cyclodextrin, and sugar alcohol such as xylitol, sorbitol, and erythritol. Examples of the flavoring agents may include natural flavoring agents (thaumatin, *stevia* extracts (such as rebaudioside A), glycyrrhizin, and the like) and synthetic flavoring agents (saccharin, aspartame, and the like).

In addition, the food composition of the present invention may contain various nutrients, vitamins, minerals (electrolytes), flavorings such as synthetic flavorings and natural flavorings, colorants, pectic acid and salts thereof, alginic acid and salts thereof, organic acids, protective colloidal thickeners, pH adjusting agents, stabilizers, preservatives, glycerin, alcohol, carbonizing agents used in carbonated beverages, and the like.

These ingredients may be used individually or in combination. A proportion of such additives is not so important, and is generally selected from the range of 0.1 to about 50 parts by weight per 100 parts by weight of the food composition of the present invention.

According to still yet another embodiment of the present invention, there is provided a method for preventing or treating an immune disease, comprising a step of administering, to a target individual, the myeloid-derived suppressor cells provided in the present invention or the pharmaceutical composition provided in the present invention, so that the immune disease is prevented or treated.

As used herein, the "target individual" refers to an individual who has developed or is more likely to develop an immune disease.

In the present invention, the immune disease may be graft rejection after organ transplantation, graft rejection after hematopoietic stem cell transplantation, an autoimmune disease, or an allergic disease, which is caused by a hypersensitive immune response.

The dosage, schedule, and route of administration for myeloid-derived suppressor cells provided in the present invention may be determined depending on the size and condition of an individual and in accordance with standard pharmaceutical practice. Exemplary route of administration includes intravenous, intraarterial, intraperitoneal, intrapulmonary, intravascular, intramuscular, intratracheal, subcutaneous, intraocular, intrathecal, or transdermal route.

A dose of myeloid-derived suppressor cells to be administered to an individual may vary depending, for example, on the specific type of myeloid-derived suppressor cells to be administered, the route of administration, and the specific type and stage of an immune disease to be treated. The dose should be sufficient to produce a desired response, such as a therapeutic response to an immune disease, without severe toxicity or adverse events. The magnitude of effects may be measured using standard methods such as in vitro assays with purified enzymes, cell-based assays, animal model experiments, or human experiments. For example, the myeloid-derived suppressor cells may be administered in a cell number of $2 \times 10^4$ cells/ml to $8 \times 10^7$ cells/ml. However, the present invention is not limited thereto.

In addition, in the present invention, the myeloid-derived suppressor cells may be formulated in the form of oral preparations such as powders, granules, capsules, tablets, aqueous suspensions, and the like, preparations for external use, suppositories, and sterile injectable solutions, respectively, according to conventional methods, and administered.

In addition, in the present invention, a pharmaceutically acceptable carrier may also be administered in addition to the myeloid-derived suppressor cells. As the pharmaceutically acceptable carrier, a binder, a glidant, a disintegrant, an excipient, a solubilizer, a dispersant, a stabilizer, a suspending agent, a pigment, a flavor, and the like may be used for oral administration; a buffer, a preserving agent, a pain-relieving agent, a solubilizer, an isotonic agent, a stabilizer, and the like may be used in admixture for injections; and a base, an excipient, a lubricant, a preserving agent, and the like may be used for topical administration. In addition, in the present invention, the secretory protein may be made into preparations in various ways by being mixed with a pharmaceutically acceptable carrier. For example, for oral administration, the pharmaceutical composition may be formulated in the form of tablets, troches, capsules, elixirs, suspensions, syrups, wafers, or the like. For injections, the pharmaceutical composition may be formulated in the form of unit dosage ampoules or multiple dosage forms. Alternatively, the pharmaceutical composition may be formulated into solutions, suspensions, tablets, capsules, sustained-release preparations, or the like.

Meanwhile, as examples of carriers, excipients, or diluents suitable for making preparations, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, or the like may be used. In addition, a filler, an anti-coagulant, a lubricant, a wetting agent, a flavor, an emulsifier, a preservative, and the like may further be included.

Induction of Monocytic Myeloid-Derived Suppressor Cells (M-MDSCs) with High PDCA-1 Expression Level Using Type I Interferon The present inventors have discovered that in a case where bone marrow cells are treated with type I interferon, monocytic myeloid-derived suppressor cells (M-MDSCs) with high PDCA-1 expression level are induced, and then in a case where such M-MDSCs are treated with a growth factor, immunogenic dendritic cells are induced which are capable of inducing differentiation of naive T cells into Th1 cells; and thus have arrived at the present invention.

According to an embodiment of the present invention, there is provided a method for producing myeloid-derived suppressor cells (MDSCs), comprising a step of treating bone marrow cells with type I interferon, to induce differentiation into myeloid-derived suppressor cells.

Specifically, in the present invention, in a case where bone marrow cells are treated with type I interferon, differentiation into monocytic myeloid-derived suppressor cells (M-MDSCs) may be induced.

In the present invention, the "interferon" generally relates to a cytokine that is typically produced by cells of the immune system and by a wide variety of other cells in response to presence of double-stranded RNA or another type 1 interferon-inducing stimulus.

In the present invention, the "type I interferon" may include any member of a subgroup of interferon proteins that are known in the art and can be identified, for example, by their capacity to bind to a specific cell surface receptor complex known as interferon-α receptor (IFNAR), in which the complex is composed of IFNAR1 and IFNAR2 (De Weerd et al., 2007, J Biol Chem 282 (28): 20053-20057). IFNAR is associated with kinases TYK2 and JAK1. Once activated, the IFNAR complex phosphorylates signal transducers and activators of transcription (STAT) family members, STAT1 and STAT2, in the transcription process, which, in turn, heterotrimerize with interferon regulatory factor 9 (IRF9) to form interferon-stimulated gene factor 3 (ISGF3) complex (Janus kinase (JAK)/STAT pathway). ISGF3 migrates to the nucleus and binds to interferon-stimulated response element (ISRE), a DNA motif that can be identified in the regulatory region of various interferon-stimulated genes (ISGs) (reviewed in Hundeshagen, 2012, supra). There are also various positive and negative feedback loops in the type I interferon-related pathways. Type I interferons identified in mammalian systems include, but are not limited to, IFN-α, IFN-β, IFN-κ, IFN-δ, IFN-ε, IFN-τ, IFN-ω, and IFN-ζ (also known as limitn). Type I interferons identified in the human body are IFN-α, IFN-β, IFN-κ (also known as IFNK), and IFN-ω. Various subtypes (including IFN-α-2a and IFN-α-2b) of the IFN-α protein and various subtypes (including IFN-β-1a and IFN-β-1b) of the IFN-β protein are produced by various types of cells, including lymphocytes, macrophages, plasmacytoid dendritic cells, fibroblasts, endothelial cells, and other cells, and are typically involved in innate immune responses. IFN-α is also commercially produced for human administration to treat various diseases, including HCV, certain other viral infections, and some types of cancer, and has been commercially provided primarily as a PEGylated form (for example, pegIFN-α). IFN-β has also been commercially produced to treat a variety of diseases, including MS.

In the present invention, the type I interferon used to treat bone marrow cells may be at least one selected from the group consisting of IFN-α, IFN-β, IFN-κ, and IFN-ω, may preferably be at least one of IFN-α or IFN-β, and may more preferably be IFN-β.

In the present invention, the type I interferon may be applied in an amount of 10 ng/ml to 1,000 ng/ml, 10 ng/ml to 5,000 ng/ml, or 10 ng/ml to 100 ng/ml. However, the present invention is not limited thereto.

In the present invention, the type I interferon may be applied one or more times before initiation of, at the initiation time of, or during bone marrow cell differentiation; and may be preferably applied at the initiation time of bone marrow cell differentiation, and then applied one or more times during the differentiation. However, the present invention is not limited thereto.

In the present invention, the bone marrow cell differentiation may be carried out by inoculating the bone marrow cells in a medium supplemented with a growth factor and performing culture for 5 to 10 days, 5 to 7 days, or 6 days.

In addition, in the present invention, in a case where the type I interferon is applied one or more times before the initiation of bone marrow cell differentiation, the bone marrow cells may be treated with a growth factor within 36 hours, preferably 24 hours, from any one time point at which the type I interferon has been applied, so that the differentiation is initiated. However, the present invention is not limited thereto.

In the present invention, in a case where the type I interferon is applied at the initiation time of bone marrow cell differentiation, the bone marrow cells may be inoculated and cultured in a medium supplemented with type I interferon and a growth factor. However, the present invention is not limited thereto.

In the present invention, in a case where the type I interferon is applied one or more times during bone marrow cell differentiation, the type I interferon may be applied one or more times within 3 days (72 hours) or 5 days (120 hours) from the initiation time of differentiation. However, the present invention is not limited thereto.

As used herein, the term "initiation of differentiation" may refer to a process in which a growth factor is added to a culture medium of bone marrow cells, or bone marrow cells are inoculated in a medium supplemented with a growth factor, and culture is performed. The process is not particularly limited as long as such a process can induce differentiation of bone marrow cells using a growth factor.

In the present invention, the growth factor is a stimulant of bone marrow cells, and may be preferably at least one selected from the group consisting of granulocyte-macrophage colony stimulating factor (GM-CSF), granulocyte colony stimulating factor (G-CSF), macrophage colony stimulating factor (M-CSF), stem cell factor (SCF), FMS-like tyrosine kinase 3 (Flt3), and interleukin 3 (IL-3), with granulocyte-macrophage colony stimulating factor (GM-CSF) being more preferred.

In the present invention, the growth factor may be applied in an amount of 10 ng/ml to 500 ng/ml, 10 ng/ml to 100 ng/ml, or 10 ng/ml to 50 ng/ml. However, the present invention is not limited thereto.

In the present invention, in a case where the type I interferon is applied at the initiation time of and during bone marrow cell differentiation using the growth factor, monocytic myeloid-derived suppressor cells (M-MDSCs) having the cellular phenotype CD11c⁻CD11b⁺Ly6G⁻Ly6C⁺PDCA-1⁺ may be induced from the bone marrow cells.

In the present invention, the monocytic myeloid-derived suppressor cells induced by treatment with type I interferon, as described above, have high expression level of PDCA-1, have low expression level of CD124, and have a characteristic of expressing remarkably high levels of NOS2, arginase-1 (Arg-1), and IL-10 upon stimulation with lipopolysaccharide (LPS) and interferon-γ (IFN-gamma).

According to another embodiment of the present invention, there is provided a method for producing dendritic cells, comprising a step of treating the monocytic myeloid-derived suppressor cells having the cellular phenotype CD11c⁻CD11b⁺Ly6G⁻Ly6C⁺PDCA-1⁺ with a growth factor, to induce differentiation into dendritic cells, according to the present invention.

In the present invention, the growth factor used for inducing differentiation into dendritic cells may be at least one selected from the group consisting of granulocyte-macrophage colony stimulating factor (GM-CSF), granulocyte colony stimulating factor (G-CSF), macrophage colony stimulating factor (M-CSF), stem cell factor (SCF), FMS-like tyrosine kinase 3 (Flt3), and interleukin 3 (IL-3), with granulocyte-macrophage colony stimulating factor (GM-CSF) being preferred.

In addition, in the present invention, the growth factor may be applied in an amount of 10 ng/ml to 500 ng/ml, 10 ng/ml to 100 ng/ml, or 10 ng/ml to 50 ng/ml.

In addition, in the present invention, the growth factor may be applied for 12 hours to 7 days, preferably 24 hours to 5 days, and more preferably 3 to 5 days. However, the present invention is not limited thereto.

In the present invention, as the monocytic myeloid-derived suppressor cells having the cellular phenotype CD11c⁻CD11b⁺Ly6G⁻Ly6C⁺PDCA-1⁺ are treated with a growth factor, differentiation into immunogenic dendritic cells may be induced.

In the present invention, the dendritic cells obtained as described above have high expression levels of CD64 and CD115 in their cellular phenotype, and show significantly increased expression levels of IL-12p′70, TNF-α, IL-6, IL-10, and $NO_2$ upon stimulation with lipopolysaccharide and interferon-γ. In addition, in a case where T cells are stimulated with the dendritic cells of the present invention, the T cells show increased INF-γ secretion capacity and naive T cells are induced to differentiate into Th1 cells so that immunogenicity can be enhanced.

Based on these characteristics, according to yet another embodiment of the present invention, there is provided an immunotherapeutic agent, comprising the dendritic cell. The immunotherapeutic agent according to the present invention may increase immune responses or selectively increase some of immune responses desired for treatment or prevention of a particular disease, infection, or condition.

According to still yet another embodiment of the present invention, there is provided an antitumor vaccine or a pharmaceutical composition for treating a tumor, comprising the dendritic cell.

Based on the fact that tumors are rich in latent antigens and these tumors have immunogenicity in a case where such antigens are presented by dendritic cells, the dendritic cell according to the present invention may be used as an antitumor vaccine for tumor prevention or a therapeutic agent for tumors. Since immunogenicity of an individual can be increased by the dendritic cell according to the present invention, the dendritic cell makes it possible to prevent or inhibit tumor proliferation and/or metastasis in the individual.

In the present invention, the tumor may be, but is not limited to, at least one selected from the group consisting of liver cancer, bile duct cancer, gallbladder cancer, esophageal cancer, gastric cancer, ovarian cancer, breast cancer, uterine cancer, colon cancer, rectal cancer, cervical cancer, prostate cancer, skin cancer, pancreatic cancer, leukemia, lymphoma, Hodgkin's disease, lung cancer, bronchial cancer, multiple myeloma, leukemia, lymphoma, squamous cell carcinoma, kidney cancer, urethral cancer, bladder cancer, head and neck cancer, brain cancer, and central nervous system cancer.

For the antigens for dendritic cell vaccines which are usable in the present invention, any antigen capable of binding to a transmembrane peptide may be used, and examples thereof may include inactivated tumor cells, and tumor cell-related genes, peptides, or proteins prepared by genetic recombination methods. In a case where the antigen is intended to be obtained by a genetic recombination method, the nucleotide sequence encoding the antigen may be known. The known sequence may be used in full-length, and a portion of the full-length sequence may also be used. The nucleotide sequence encoding the antigen may be cloned into a vector so that the desired antigen is expressed.

For the antitumor vaccine according to the present invention, both the immunization method performed by single administration and the immunization method performed by continuous administration may be used.

In the present invention, for the route of administration for the immunotherapeutic agent, antitumor vaccine, or pharmaceutical composition for treating a tumor, any general route may be used for administration as long as the route allows the immunotherapeutic agent, antitumor vaccine, or pharmaceutical composition to reach a target tissue. Administration may be made via a parenteral route, for example, intraperitoneal administration, intravenous administration, intramuscular administration, subcutaneous administration, and intradermal administration. However, the present invention is not limited thereto. The composition may be formulated in a suitable form with a pharmaceutical carrier generally used for cell therapy. The term "pharmaceutically acceptable" refers to a composition which is physiologically acceptable and typically does not cause gastrointestinal disorders, allergic reactions such as dizziness, or similar reactions in a case of being administered to a human. Examples of the pharmaceutically acceptable carrier may include carriers for parenteral administration such as water, suitable oil, saline, aqueous glucose, and glycol, and the like, and may further include stabilizers and preservatives. Examples of suitable stabilizers include antioxidants such as sodium hydrogen sulfite, sodium sulfite, or ascorbic acid. Examples of suitable preservatives include benzalkonium chloride, methyl- or propyl-paraben, and chlorobutanol. For other pharmaceutically acceptable carriers, reference may be made to those described in the following literature: Remington's Pharmaceutical Sciences, 19th ed., Mack Publishing Company, Easton, Pa., 1995.

In addition, in the present invention, the immunotherapeutic agent may also be administered by any device capable of being moved to a target cell.

The immunotherapeutic agent, antitumor vaccine, or pharmaceutical composition for treating a tumor, of the present invention, may comprise a therapeutically effective amount of dendritic cells for treatment of a disease. The therapeutically effective amount refers to an amount of an active ingredient or a pharmaceutical composition which induces a biological or medical response in a tissue system, an animal, or a human, considered by researchers, veterinarians, physicians, or other clinicians, and includes an amount that induces alleviation of symptoms of a disease or disorder to be treated. It is apparent to those skilled in the art that the amount (number) of dendritic cells to be contained in the immunotherapeutic agent, antitumor vaccine, or pharmaceutical composition for treating a tumor, of the present invention, will vary depending on a desired effect. Therefore, an optimal amount of the cell therapeutic agent may be easily determined by those skilled in the art, and may be adjusted depending on various factors including type of disease, severity of disease, amounts of other ingredients contained in the composition, type of formulation, and the patient's age, body weight, general health status, sex, and diet, time of administration, route of administration and excretion rate of the composition, treatment duration, and simultaneously used drugs. For example, the dendritic cells may be contained in an amount of $2\times10^4$ cells/ml to $8\times10^7$ cells/ml. However, the present invention is not limited thereto.

The immunotherapeutic agent, antitumor vaccine, or pharmaceutical composition for treating a tumor, of the present invention, may be administered in a conventional manner via rectal, intravenous, intraarterial, intraperitoneal, intramuscular, intrasternal, transdermal, topical, intraocular, subcutaneous, or intradermal route.

According to still yet another embodiment of the present invention, there is provided a method for preventing or treating a tumor, comprising a step of administering, to a target individual, the dendritic cells provided in the present invention or the pharmaceutical composition provided in the present invention so that the tumor is prevented or treated.

As used herein, the "target individual" refers to an individual who has developed or is more likely to develop a tumor.

In the present invention, the tumor may be, but is not limited to, at least one selected from the group consisting of liver cancer, bile duct cancer, gallbladder cancer, esophageal cancer, gastric cancer, ovarian cancer, breast cancer, uterine cancer, colon cancer, rectal cancer, cervical cancer, prostate cancer, skin cancer, pancreatic cancer, leukemia, lymphoma, Hodgkin's disease, lung cancer, bronchial cancer, multiple myeloma, leukemia, lymphoma, squamous cell carcinoma, kidney cancer, urethral cancer, bladder cancer, head and neck cancer, brain cancer, and central nervous system cancer.

The dosage, schedule, and route of administration for dendritic cells provided in the present invention may be determined depending on the size and condition of an individual and in accordance with standard pharmaceutical practice. Exemplary route of administration includes intravenous, intraarterial, intraperitoneal, intrapulmonary, intravascular, intramuscular, intratracheal, subcutaneous, intraocular, intrathecal, or transdermal route.

A dose of dendritic cells to be administered to an individual may vary depending, for example, on the specific type of dendritic cells to be administered, the route of administration, and the specific type and stage of a tumor to be treated. The dose should be sufficient to produce a desired response, such as a therapeutic response to a tumor, without severe toxicity or adverse events. The magnitude of effects may be measured using standard methods such as in vitro assays with purified enzymes, cell-based assays, animal model experiments, or human experiments. For example, the dendritic cells may be administered in a cell number of $2\times10^4$ cells/ml to $8\times10^7$ cells/ml. However, the present invention is not limited thereto.

In addition, in the present invention, the dendritic cells may be formulated in the form of oral preparations such as powders, granules, capsules, tablets, aqueous suspensions, and the like, preparations for external use, suppositories, and sterile injectable solutions, respectively, according to conventional methods, and administered.

In addition, in the present invention, a pharmaceutically acceptable carrier may also be administered in addition to the dendritic cells. As the pharmaceutically acceptable carrier, a binder, a glidant, a disintegrant, an excipient, a solubilizer, a dispersant, a stabilizer, a suspending agent, a pigment, a flavor, and the like may be used for oral administration; a buffer, a preserving agent, a pain-relieving agent, a solubilizer, an isotonic agent, a stabilizer, and the like may be used in admixture for injections; and a base, an excipient, a lubricant, a preserving agent, and the like may be used for topical administration. In addition, in the present invention, the secretory protein may be made into preparations in various ways by being mixed with a pharmaceutically acceptable carrier. For example, for oral administration, the pharmaceutical composition may be formulated in the form of tablets, troches, capsules, elixirs, suspensions, syrups, wafers, or the like. For injections, the pharmaceutical composition may be formulated in the form of unit dosage ampoules or multiple dosage forms. Alternatively, the pharmaceutical composition may be formulated into solutions, suspensions, tablets, capsules, sustained-release preparations, or the like.

Meanwhile, as examples of carriers, excipients, or diluents suitable for making preparations, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, or the like may be used. In addition, a filler, an anti-coagulant, a lubricant, a wetting agent, a flavor, an emulsifier, a preservative, and the like may further be included.

Induction of Immunogenic Dendritic Cells Using Toll-Like Receptor Agonist (TLR Agonist)

The present inventors have discovered that in a case where the monocytic myeloid-derived suppressor cells (M-MDSCs) induced by treatment of bone marrow cells with a toll-like receptor agonist (TLR agonist) are treated with a growth factor, immunogenic dendritic cells are induced which are capable of inducing differentiation of naive T cells into Th1 cells; and thus have arrived at the present invention.

According to an embodiment of the present invention, there is provided a method for producing dendritic cells, comprising steps of: (1) treating bone marrow cells with a toll-like receptor agonist (TLR agonist), to induce differentiation into myeloid-derived suppressor cells (MDSCs); and (2) treating the differentiation-induced myeloid-derived suppressor cells with a growth factor, to induce differentiation into dendritic cells.

Specifically, in the present invention, in the above step (1), in a case where the bone marrow cells are treated with the toll-like receptor agonist, differentiation into monocytic myeloid-derived suppressor cells (M-MDSCs) may be induced.

In the present invention, the toll-like receptor agonist used to treat the bone marrow cells is preferably an agonist of an intracellular toll-like receptor; and is more preferably at least one of toll-like receptor 7 agonist or toll-like receptor 9 agonist, among the agonists of intracellular toll-like receptors, for inducing differentiation into dendritic cells having desired properties in the present invention.

As used herein, the term "intracellular toll-like receptor" refers to a toll-like receptor that is present in the cell in a case where toll-like receptors are classified based on their intracellular distribution, and the types belonging thereto include toll-like receptor 3 (TLR3), toll-like receptor 7 (TLR7), toll-like receptor 8 (TLR8), and toll-like receptor 9 (TLR9). Activity of the intracellular toll-like receptor depends on translocation to the endosomal/lysosomal compartment, and an acidic environment in endolysosomes is essentially required for the activity (Nishiya et al., J Biol Chem 280, 37107-17 (2005); Gibbard et al., J Biol Chem 281, 27503-11 (2006); and Ranjith-Kumar et al., J Biol Chem 282, 7668-78 (2007)). The translocation occurs only after the toll-like receptor is exposed to an agonist thereof and then binds to the vesicle protein UNC93b (Tabeta et al., Nat Immunol 7, 156-64 (2006); Kim et al., Nature 452, 234-8 (2008); Brinkmann et al., J Cell Biol 177, 265-75 (2007); Latz et al., Nat Immunol 5, 190-8 (2004); and Park et al., Nat Immunol 9, 1407-14 (2008)).

Among the terms used herein, definitions and types of "toll-like receptor 7 (TLR7)" and "toll-like receptor 9 (TLR9)" overlap with those as described above for the method for producing myeloid-derived suppressor cells, and thus the detailed description thereof is omitted below.

In the present invention, the toll-like receptor agonist may be applied in an amount of 10 ng/ml to 1,000 ng/ml, 10 ng/ml to 5,000 ng/ml, or 10 ng/ml to 100 ng/ml. However, the present invention is not limited thereto.

In the present invention, the toll-like receptor agonist may be applied one or more times before initiation of, at the initiation time of, or during bone marrow cell differentiation; and may be preferably applied at the initiation time of bone marrow cell differentiation, and then applied one or more times during the differentiation. However, the present invention is not limited thereto.

In the present invention, the bone marrow cell differentiation may be carried out by inoculating the bone marrow cells in a medium supplemented with a growth factor and performing culture for 5 to 10 days, 5 to 7 days, or 6 days.

In addition, in the present invention, in a case where the toll-like receptor agonist is applied one or more times before the initiation of bone marrow cell differentiation, the bone marrow cells may be treated with a growth factor within 36 hours, preferably 24 hours, from any one time point at which the agonist has been applied, so that the differentiation is initiated. However, the present invention is not limited thereto.

In the present invention, in a case where the toll-like receptor agonist is applied at the initiation time of bone marrow cell differentiation, the bone marrow cells may be cultured in a medium supplemented with the toll-like receptor agonist and a growth factor. However, the present invention is not limited thereto.

In the present invention, in a case where the toll-like receptor agonist is applied during bone marrow cell differentiation, the toll-like receptor agonist may be applied one or more times within 3 days (72 hours) or 5 days (120 hours) from the initiation time of bone marrow cell differentiation. However, the present invention is not limited thereto.

As used herein, the term "initiation of differentiation" may refer to a process in which a growth factor is added to a culture medium of bone marrow cells, or bone marrow cells are inoculated in a medium supplemented with a growth factor, and culture is performed. The process is not particularly limited as long as such a process can induce differentiation of bone marrow cells using a growth factor.

In the present invention, the growth factor is a stimulant of bone marrow cells, and may be preferably at least one selected from the group consisting of granulocyte-macrophage colony stimulating factor (GM-CSF), granulocyte colony stimulating factor (G-CSF), macrophage colony stimulating factor (M-CSF), stem cell factor (SCF), FMS-like tyrosine kinase 3 (Flt3), and interleukin 3 (IL-3), with granulocyte-macrophage colony stimulating factor (GM-CSF) being more preferred.

In the present invention, the growth factor may be applied in an amount of 10 ng/ml to 500 ng/ml, 10 ng/ml to 100 ng/ml, or 10 ng/ml to 50 ng/ml. However, the present invention is not limited thereto.

In the present invention, in the above step (1), in a case where at least one of the toll-like receptor 7 agonist and toll-like receptor 9 agonist is applied at the initiation time of and during bone marrow cell differentiation using the growth factor, monocytic myeloid-derived suppressor cells (M-MDSCs) having the cellular phenotype CD11c$^-$CD11b$^+$Ly6G$^-$ Ly6C$^+$PDCA-1$^+$ may be induced from the bone marrow cells.

In the present invention, unlike monocytic myeloid-derived suppressor cells induced by treatment with other types of toll-like receptor agonists (for example, toll-like receptor 2 agonist, toll-like receptor 8 agonist, and the like), the monocytic myeloid-derived suppressor cells induced by treatment with a toll-like receptor 7 agonist or a toll-like receptor 9 agonist, as described above, have high expression level of PDCA-1, have low expression level of CD124, and have a characteristic of expressing remarkably high levels of NOS2, arginase-1 (Arg-1), and IL-10 upon stimulation with lipopolysaccharide (LPS) and interferon-γ (IFN-gamma).

In the present invention, once the monocytic myeloid-derived suppressor cells are obtained as described above, the monocytic myeloid-derived suppressor cells may be treated with a growth factor to induce differentiation into dendritic cells in the above step (2).

In the present invention, the growth factor may be at least one selected from the group consisting of granulocyte-macrophage colony stimulating factor (GM-CSF), granulocyte colony stimulating factor (G-CSF), macrophage colony stimulating factor (M-CSF), stem cell factor (SCF), FMS-like tyrosine kinase 3 (Flt3), and interleukin 3 (IL-3), with granulocyte-macrophage colony stimulating factor (GM-CSF) being preferred.

In addition, in the present invention, the growth factor may be applied in an amount of 10 ng/ml to 500 ng/ml, 10 ng/ml to 100 ng/ml, or 10 ng/ml to 50 ng/ml.

In addition, in the present invention, the growth factor may be applied for 12 hours to 7 days, preferably 24 hours to 5 days, and more preferably 3 to 5 days. However, the present invention is not limited thereto.

In the present invention, in the above step (2), as the monocytic myeloid-derived suppressor cells having the cellular phenotype CD11c$^-$CD11b$^+$Ly6G$^-$Ly6C$^+$PDCA-1$^+$ are treated with a growth factor, differentiation into immunogenic dendritic cells may be induced.

In the present invention, the dendritic cells obtained as described above has high expression levels of CD64 and CD115 in their cell phenotype, and show significantly increased expression levels of IL-12p70, TNF-α, IL-6, IL-10, and $NO_2$ upon stimulation with lipopolysaccharide and interferon-γ. In addition, in a case where T cells are stimulated with the dendritic cells of the present invention, the T cells show increased INF-γ secretion capacity and naive T cells are induced to differentiate into Th1 cells so that immunogenicity can be enhanced.

Based on these characteristics, according to still yet another embodiment of the present invention, there is provided an immunotherapeutic agent, comprising the dendritic cell. The immunotherapeutic agent according to the present invention may increase immune responses or selectively increase some of immune responses desired for treatment or prevention of a particular disease, infection, or condition.

According to still yet another embodiment of the present invention, there is provided an antitumor vaccine or a pharmaceutical composition for treating a tumor, comprising the dendritic cell.

Based on the fact that tumors are enriched with latent antigens and these tumors are immunogenic in a case where such antigens are presented by dendritic cells, the dendritic cell according to the invention may be used as an antitumor vaccine for tumor prevention or a therapeutic agent for tumors. Since immunogenicity of an individual can be increased by the dendritic cells according to the present invention, the dendritic cell makes it possible to prevent or inhibit tumor proliferation and/or metastasis in the individual.

In the present invention, the tumor may be, but is not limited to, at least one selected from the group consisting of liver cancer, bile duct cancer, gallbladder cancer, esophageal cancer, gastric cancer, ovarian cancer, breast cancer, uterine cancer, colon cancer, rectal cancer, cervical cancer, prostate cancer, skin cancer, pancreatic cancer, leukemia, lymphoma, Hodgkin's disease, lung cancer, bronchial cancer, multiple myeloma, leukemia, lymphoma, squamous cell carcinoma, kidney cancer, urethral cancer, bladder cancer, head and neck cancer, brain cancer, and central nervous system cancer.

For the antigens for dendritic cell vaccines which are usable in the present invention, any antigen capable of binding to a transmembrane peptide may be used, and examples thereof may include inactivated tumor cells, and tumor cell-related genes, peptides, or proteins prepared by genetic recombination methods. In a case where the antigen is intended to be obtained by a genetic recombination method, the nucleotide sequence encoding the antigen may be known. The known sequence may be used in full-length, and a portion of the full-length sequence may also be used. The nucleotide sequence encoding the antigen may be cloned into a vector so that the desired antigen is expressed.

For the antitumor vaccine according to the present invention, both the immunization method performed by single administration and the immunization method performed by continuous administration may be used.

In the present invention, for the route of administration for the immunotherapeutic agent, antitumor vaccine, or pharmaceutical composition for treating a tumor, any general route may be used for administration as long as the route allows the immunotherapeutic agent, antitumor vaccine, or pharmaceutical composition to reach a target tissue. Administration may be made via a parenteral route, for example, intraperitoneal administration, intravenous administration, intramuscular administration, subcutaneous administration, and intradermal administration. However, the present invention is not limited thereto. The composition may be formulated in a suitable form with a pharmaceutical carrier generally used for cell therapy. The term "pharmaceutically acceptable" refers to a composition which is physiologically acceptable and typically does not cause gastrointestinal disorders, allergic reactions such as dizziness, or similar reactions in a case of being administered to a human. Examples of the pharmaceutically acceptable carrier may include carriers for parenteral administration such as water, suitable oil, saline, aqueous glucose, and glycol, and the like, and may further include stabilizers and preservatives. Examples of suitable stabilizers include antioxidants such as sodium hydrogen sulfite, sodium sulfite, or ascorbic acid. Examples of suitable preservatives include benzalkonium chloride, methyl- or propyl-paraben, and chlorobutanol. For other pharmaceutically acceptable carriers, reference may be made to those described in the following literature: Remington's Pharmaceutical Sciences, 19th ed., Mack Publishing Company, Easton, Pa., 1995.

In addition, in the present invention, the immunotherapeutic agent may also be administered by any device capable of being moved to a target cell.

The immunotherapeutic agent, antitumor vaccine, or pharmaceutical composition for treating a tumor, of the present invention, may comprise a therapeutically effective amount of dendritic cells for treatment of a disease. The therapeutically effective amount refers to an amount of an active ingredient or a pharmaceutical composition which induces a biological or medical response in a tissue system, an animal, or a human, considered by researchers, veterinarians, physicians, or other clinicians, and includes an amount that induces alleviation of symptoms of a disease or disorder to be treated. It is apparent to those skilled in the art that the amount (number) of dendritic cells to be contained in the immunotherapeutic agent, antitumor vaccine, or pharmaceutical composition for treating a tumor, of the present invention, will vary depending on a desired effect. Therefore, an optimal amount of the cell therapeutic agent may be easily determined by those skilled in the art, and may be adjusted depending on various factors including type of disease, severity of disease, amounts of other ingredients contained in the composition, type of formulation, and the patient's age, body weight, general health status, sex, and diet, time of administration, route of administration and excretion rate of the composition, treatment duration, and simultaneously used drugs. For example, the dendritic cells may be contained in an amount of $2 \times 10^4$ cells/ml to $8 \times 10^7$ cells/ml. However, the present invention is not limited thereto.

The immunotherapeutic agent, antitumor vaccine, or pharmaceutical composition for treating a tumor, of the present invention, may be administered in a conventional manner via rectal, intravenous, intraarterial, intraperitoneal, intramuscular, intrasternal, transdermal, topical, intraocular, subcutaneous, or intradermal route.

According to still yet another embodiment of the present invention, there is provided a method for preventing or treating a tumor, comprising a step of administering, to a target individual, the dendritic cells provided in the present invention or the pharmaceutical composition provided in the present invention so that the tumor is prevented or treated.

As used herein, the "target individual" refers to an individual who has developed or is more likely to develop a tumor.

In the present invention, the tumor may be, but is not limited to, at least one selected from the group consisting of liver cancer, bile duct cancer, gallbladder cancer, esophageal cancer, gastric cancer, ovarian cancer, breast cancer, uterine cancer, colon cancer, rectal cancer, cervical cancer, prostate cancer, skin cancer, pancreatic cancer, leukemia, lymphoma, Hodgkin's disease, lung cancer, bronchial cancer, multiple myeloma, leukemia, lymphoma, squamous cell carcinoma, kidney cancer, urethral cancer, bladder cancer, head and neck cancer, brain cancer, and central nervous system cancer.

The dosage, schedule, and route of administration for dendritic cells provided in the present invention may be determined depending on the size and condition of an individual and in accordance with standard pharmaceutical practice. Exemplary route of administration includes intravenous, intraarterial, intraperitoneal, intrapulmonary, intravascular, intramuscular, intratracheal, subcutaneous, intraocular, intrathecal, or transdermal route.

A dose of dendritic cells to be administered to an individual may vary depending, for example, on the specific type of dendritic cells to be administered, the route of administration, and the specific type and stage of a tumor to be treated. The dose should be sufficient to produce a desired response, such as a therapeutic response to a tumor, without severe toxicity or adverse events. The magnitude of effects may be measured using standard methods such as in vitro assays with purified enzymes, cell-based assays, animal model experiments, or human experiments. For example, the dendritic cells may be administered in a cell number of $2\times10^4$ cells/ml to $8\times10^7$ cells/ml. However, the present invention is not limited thereto.

In addition, in the present invention, the dendritic cells may be formulated in the form of oral preparations such as powders, granules, capsules, tablets, aqueous suspensions, and the like, preparations for external use, suppositories, and sterile injectable solutions, respectively, according to conventional methods, and administered.

In addition, in the present invention, a pharmaceutically acceptable carrier may also be administered in addition to the dendritic cells. As the pharmaceutically acceptable carrier, a binder, a glidant, a disintegrant, an excipient, a solubilizer, a dispersant, a stabilizer, a suspending agent, a pigment, a flavor, and the like may be used for oral administration; a buffer, a preserving agent, a pain-relieving agent, a solubilizer, an isotonic agent, a stabilizer, and the like may be used in admixture for injections; and a base, an excipient, a lubricant, a preserving agent, and the like may be used for topical administration. In addition, in the present invention, the secretory protein may be made into preparations in various ways by being mixed with a pharmaceutically acceptable carrier. For example, for oral administration, the pharmaceutical composition may be formulated in the form of tablets, troches, capsules, elixirs, suspensions, syrups, wafers, or the like. For injections, the pharmaceutical composition may be formulated in the form of unit dosage ampoules or multiple dosage forms. Alternatively, the pharmaceutical composition may be formulated into solutions, suspensions, tablets, capsules, sustained-release preparations, or the like.

Meanwhile, as examples of carriers, excipients, or diluents suitable for making preparations, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, or the like may be used. In addition, a filler, an anti-coagulant, a lubricant, a wetting agent, a flavor, an emulsifier, a preservative, and the like may further be included.

Advantageous Effects of Invention

According to an embodiment of the present invention, tolerogenic myeloid-derived suppressor cells can be induced at a high yield from bone marrow cells through a simple and easy process, which enables stable supply of a large amount of tolerogenic myeloid-derived suppressor cells. In addition, in the present invention, the tolerogenic myeloid-derived suppressor cells obtained as described above may inhibit expression of inflammatory cytokines and inflammatory factors and inhibit activity of T cells, so that various autoimmune diseases are effectively prevented or treated. Also, the tolerogenic myeloid-derived suppressor cells are safe in a case of being administered to humans.

According to another embodiment of the present invention, myeloid-derived suppressor cells, which may be induced to differentiate into immunogenic dendritic cells, can be induced from bone marrow cells through a simple and easy process, which enables stable supply of a large amount of immunogenic dendritic cells. In the present invention, the immunogenic dendritic cells supplied as described above can induce differentiation of naive T cells into Th1 cells, and thus increase immunogenicity of an individual to which such cells are administered, thereby exerting an anticancer effect. Accordingly, the immunogenic dendritic cell can be usefully used for an antitumor vaccine or composition for treating a tumor.

BRIEF DESCRIPTION OF DRAWINGS

FIG. 1 illustrates a schematic diagram for three methods in which bone marrow cells are treated with a TLR agonist, in Example 1 of the present invention.

FIG. 2 illustrates results obtained by treatment of bone marrow cells with various TLR agonists and then analyzing, by flow cytometry, whether CD11c$^+$ cells have been induced, in Example 1 of the present invention.

FIG. 3 illustrates results obtained by treatment of bone marrow cells with various TLR agonists and then measuring a proportion of CD11c$^+$ cells, in Example 1 of the present invention.

FIG. 4 illustrates results obtained by measuring changes in proportion of CD11c$^+$ cells for respective concentrations of TLR agonists used to treat bone marrow cells, in Example 1 of the present invention.

FIG. 5 illustrates results obtained by treating respective bone marrow cells of C57BL/6 mice and C57BL/6 MyD88$^{-/-}$ mice with various TLR agonists and then analyzing, by flow cytometry, whether CD11c$^+$MHC-II$^+$ cells have been induced, in Example 2 of the present invention.

FIG. 6 illustrates results obtained by treating respective bone marrow cells of C57BL/6 mice and C57BL/6 MyD88$^{-/-}$ mice with various TLR agonists and then measuring a proportion of CD11c$^+$MHC-II$^+$ cells, in Example 2 of the present invention.

FIG. 7 illustrates results obtained by analyzing the phenotypes CD11c, CD11b, Gr-1, F4/80, Ly6C, CD4, CD8a, CD103, PDCA-1, B220, NK1.1, and CD49b in the cells that have been induced by differentiation after treatment of bone marrow cells with various TLR agonists, in Example 3 of the present invention.

FIG. 8 illustrates results obtained by measuring proportions of CD11c$^+$, CD11b$^+$, Gr-1$^+$, F4/80$^+$, Ly6C$^+$, CD4$^+$, CD8α$^+$, CD103$^+$, PDCA-1$^+$, B220$^+$, NK1.1$^+$, and CD49b$^+$ cells in the cells that have been induced by differentiation after treatment of bone marrow cells with various TLR agonists, in Example 3 of the present invention.

FIG. 9 illustrates results obtained by analyzing, by flow cytometry, an expression level of Gr-1 in the cells that have been induced by differentiation after treatment of bone marrow cells with various TLR agonists, in Example 4 of the present invention.

FIG. 10 illustrates results obtained by measuring proportions of Gr-1$^+$CD11b$^+$CD11c$^-$, Gr-1$^{high}$CD11b$^+$CD11c$^-$, and Gr-1$^{int}$CD11b$^+$CD11c$^-$ cells in the cells that have been induced by differentiation after treatment of bone marrow cells with various TLR agonists, in Example 4 of the present invention.

FIG. 11 illustrates results obtained by analyzing, by flow cytometry, expression levels of LyG and LyC in the cells that have been induced by differentiation after treatment of bone marrow cells with various TLR agonists, in Example 4 of the present invention.

FIG. 12 illustrates results obtained by measuring proportions of CD11c$^-$ CD11b$^+$LyG$^+$LyC$^-$, CD11c$^-$CD11b$^+$LyG$^+$LyC$^{int}$, CD11c$^-$CD11b$^+$LyG$^-$LyC$^{int}$, and CD11c$^-$ CD11b$^+$LyG$^-$LyC$^{high}$ cells in the cells that have been induced by differentiation after treatment of bone marrow cells with various TLR agonists, in Example 4 of the present invention.

FIG. 13 illustrates results obtained by measuring proportions of CD11c$^-$ CD11b$^+$LyG$^+$LyC$^-$, CD11c$^-$CD11b$^+$LyG$^+$LyC$^{int}$, CD11c$^-$CD11b$^+$LyG$^-$LyC$^{int}$, and CD11c$^-$ CD11b$^+$LyG$^-$LyC$^{high}$ cells in the cells that have been induced by differentiation after treatment of bone marrow cells, extracted from C57BL/6 mice and C57BL/6 MyD88$^{-/-}$ mice, with various TLR agonists, in Example 5 of the present invention.

FIG. 14 graphically illustrates results obtained by measuring changes in NO$_2$ formation level in M-MDSCs, which have been induced after treatment of bone marrow cells with a TLR2 agonist or a TLR9 agonist, while applying stimulation with LPS and IFN-γ, in Example 6 of the present invention.

FIG. 15 illustrates results obtained by analyzing, with Western blotting, changes in expression levels of NOS2 and arginase-1 in M-MDSCs, which have been induced after treatment of bone marrow cells with a TLR2 agonist or a TLR9 agonist, while applying stimulation with LPS and IFN-γ, in Example 6 of the present invention.

FIG. 16 graphically illustrates results obtained by measuring changes in expression level of IL-10 in M-MDSCs, which have been induced after treatment of bone marrow cells with a TLR2 agonist or a TLR9 agonist, while applying stimulation with LPS and IFN-γ, in Example 6 of the present invention.

FIG. 17 illustrates results obtained by analyzing, with FACS, changes in expression levels of arginase-1 (Arg-1) and iNOS in M-MDSCs, which have been induced after treatment of bone marrow cells with a TLR2 agonist or a TLR9 agonist, while applying stimulation with LPS and IFN-γ, in Example 6 of the present invention.

FIG. 18 graphically illustrates results obtained by measuring changes in expression levels of arginase-1 (Arg-1) and iNOS, and in expression level ratio of Arg-1/iNOS, in M-MDSCs which have been induced after treatment of bone marrow cells with a TLR2 agonist or a TLR9 agonist, while applying stimulation with LPS and IFN-γ, in Example 6 of the present invention.

FIG. 19 illustrates results obtained by analyzing, by flow cytometry, expression levels of CD124, CD115, F4/80, and PDCA-1 in M-MDSCs which have been induced after treatment of bone marrow cells with a TLR2 agonist or a TLR9 agonist, in Example 6 of the present invention.

FIG. 20 graphically illustrates results obtained by measuring proportions of cells expressing CD124, CD115, F4/80, and PDCA-1 in M-MDSCs which have been induced after treatment of bone marrow cells with a TLR2 agonist or a TLR9 agonist, in Example 6 of the present invention.

FIG. 21 graphically illustrates changes in expression levels of TNF-α, IL-6, IL-12p70, and IFN-β in M-MDSCs, which have been induced after treatment of bone marrow cells with a TLR2 agonist or a TLR9 agonist, while applying stimulation with LPS and IFN-γ, in Example 6 of the present invention.

FIG. 22 illustrates results obtained by analyzing, with FACS, changes in expression levels of PD-L1, PD-L2, Tim-3, FasL, and IDO in M-MDSCs, which have been induced after treatment of bone marrow cells with a TLR2 agonist or a TLR9 agonist, while applying stimulation with LPS and IFN-γ, in Example 6 of the present invention.

FIG. 23 graphically illustrates results obtained by measuring proportions of cells expressing of PD-L1, PD-L2, Tim-3, FasL, and IDO in M-MDSCs, which have been induced after treatment of bone marrow cells with a TLR2 agonist or a TLR9 agonist, while applying stimulation with LPS and IFN-γ, in Example 6 of the present invention.

FIG. 24 illustrates results obtained by analyzing, with FACS, changes in expression levels of PD-L1, PD-L2, Tim-3, FasL, and IDO in M-MDSCs, which have been induced after treatment of bone marrow cells with a TLR2 agonist or a TLR9 agonist, while applying stimulation with LPS and IFN-γ, in Example 6 of the present invention.

FIG. 25 illustrates results obtained by subjecting M-MDSCs, which have been induced after treatment of bone marrow cells with a TLR2 agonist using the 3 method, to treatment with a co-culture of OVA-pulsed DCs and CD4 T cells, and then identifying their T cell inhibition capacity, in Example 7 of the present invention.

FIG. 26 illustrates results obtained by subjecting M-MDSCs, which have been induced after treatment of bone marrow cells with a TLR9 agonist using the 3 method, to treatment with a co-culture of OVA-pulsed DCs and CD4 T cells, and then identifying their T cell inhibition capacity, in Example 7 of the present invention.

FIG. 29 illustrates results obtained by subjecting M-MDSCs, which have been induced after treatment of bone marrow cells with a TLR2 agonist using the 3 method, to treatment with a co-culture of OVA-pulsed DCs and CD4 T cells, and then analyzing, by flow cytometry, an expression level of Foxp3, in Example 7 of the present invention.

FIG. 30 illustrates results obtained by subjecting M-MDSCs, which have been induced after treatment of bone marrow cells with a TLR9 agonist using the 3 method, to treatment with a co-culture of OVA-pulsed DCs and CD4 T cells, and then analyzing, by flow cytometry, an expression level of Foxp3, in Example 7 of the present invention.

FIG. 31 graphically illustrates results obtained by subjecting M-MDSCs, which have been induced after treatment of bone marrow cells with a TLR2 agonist using the 3 method, to treatment with a co-culture of OVA-pulsed DCs and CD4 T cells, and then measuring a proportion of regulatory T cells, in Example 7 of the present invention.

FIG. 32 graphically illustrates results obtained by subjecting M-MDSCs, which have been induced after treatment of bone marrow cells with a TLR9 agonist using the 3 method, to treatment with a co-culture of OVA-pulsed DCs and CD4 T cells, and then measuring a proportion of regulatory T cells, in Example 7 of the present invention.

FIG. 33 illustrates results obtained by analyzing, by flow cytometry, expression levels of CD11c and MHC-II in the cells induced by subjecting M-MDSCs, which have been obtained by treatment of bone marrow cells with a TLR2 agonist or a TLR9 agonist using the 3 method, to treatment with GM-CSF, in Example 8 of the present invention.

FIG. 34 graphically illustrates results obtained by measuring changes in proportion of CD11c$^+$MHC-II$^+$ cells in the cells induced by subjecting M-MDSCs, which have been obtained by treatment of bone marrow cells with a TLR2 agonist or a TLR9 agonist using the 3 method, to treatment with GM-CSF, while applying stimulation with LPS and IFN-γ, in Example 8 of the present invention.

FIG. 35 illustrates results obtained by analyzing, by flow cytometry, expression levels of CD11b and F4/80 in the cells induced by subjecting M-MDSCs, which have been obtained by treatment of bone marrow cells with a TLR2 agonist or a TLR9 agonist using the 3 method, to treatment with M-CSF, in Example 8 of the present invention.

FIG. 36 graphically illustrates results obtained by measuring changes in proportion of F4/80$^+$CD11b$^+$ cells in the cells induced by subjecting M-MDSCs, which have been obtained by treatment of bone marrow cells with a TLR2 agonist or a TLR9 agonist using the 3 method, to treatment with M-CSF, while applying stimulation with LPS and IFN-γ, in Example 8 of the present invention.

FIG. 37 illustrates results obtained by analyzing T-cell proliferation inhibition capacity of M-MDSCs, which have been obtained by treatment of bone marrow cells with a TLR2 agonist or a TLR9 agonist using the 3 method, while performing culture with addition of GM-CSF, in Example 8 of the present invention.

FIG. 38 graphically illustrates results obtained by measuring changes in T-cell proliferation inhibition capacity and IFN-γ secretion capacity of M-MDSCs, which have been obtained by treatment of bone marrow cells with a TLR2 agonist or a TLR9 agonist using the 3 method, while performing culture with addition of GM-CSF, in Example 8 of the present invention.

FIG. 39 graphically illustrates results obtained by measuring a proportion of CD11c$^+$ cells in the cells induced by culturing M-MDSCs, which have been obtained by treatment of bone marrow cells with a TLR2 agonist or a TLR9 agonist using the 3 method, with addition of GM-CSF, in Example 8 of the present invention.

FIG. 40 illustrates results obtained by analyzing, by flow cytometry, expression levels of CD11c, PDCA-1, CD115, CCR2, MHC-II, CD64, CD11b, and Ly6C in the cells induced by subjecting M-MDSCs, which have been obtained by treatment of bone marrow cells with a TLR2 agonist or a TLR9 agonist using the 3 method, to treatment with GM-CSF, myeloid-derived dendritic cells, or Ly6$^+$ cell-derived dendritic cells, in Example 9 of the present invention.

FIG. 41 graphically illustrates results obtained by measuring proportions of Ly6C$^+$, MerTK$^+$, CD11b$^+$, CCR2$^+$, and PDCA-1$^+$ cells in the cells induced by subjecting M-MDSCs, which have been obtained by treatment of bone marrow cells with a TLR2 agonist or a TLR9 agonist using the 3 method, to treatment with GM-CSF, myeloid-derived dendritic cells, or Ly6$^+$ cell-derived dendritic cells, in Example 9 of the present invention.

FIG. 42 graphically illustrates changes in expression levels of TNF-α, IL-6, IL-10, IL-12p70, and NO$_2$ which are observed in a case where dendritic cells induced by subjecting M-MDSCs, which have been obtained by treatment of bone marrow cells with a TLR2 agonist or a TLR9 agonist using the 3 method, to treatment with GM-CSF, myeloid-derived dendritic cells, or Ly6$^+$ cell-derived dendritic cells are stimulated with LPS and/or IFN-γ, in Example 9 of the present invention.

FIG. 43 graphically illustrates changes in expression levels of IFN-γ, IL-2, IL-10, IL-5 and IL-17A which are observed in a case where dendritic cells induced by subjecting M-MDSCs, which have been obtained by treatment of bone marrow cells with a TLR2 agonist or a TLR9 agonist using the 3 method, to treatment with GM-CSF, myeloid-derived dendritic cells, or Ly6$^+$ cell-derived dendritic cells are stimulated with LPS and/or IFN-γ, in Example 9 of the present invention.

FIG. 44 graphically illustrates changes in T cell proliferation capacity and expression level of IFN-γ observed after subjecting CD4 T cells to treatment with dendritic cells induced by subjecting M-MDSCs, which have been obtained by treatment of bone marrow cells with a TLR2 agonist or a TLR9 agonist using the 3 method, to treatment with GM-CSF, with myeloid-derived dendritic cells, or with Ly6$^+$ cell-derived dendritic cells, in Example 9 of the present invention.

FIG. 45 graphically illustrates results obtained by analyzing expression levels of the cytokines TNF-α, IL-6, PGE2, IFN-α, and IFN-β which are induced at early differentiation stages (8, 18, and 36 hours after TLR stimulation) after treatment of bone marrow cells with a TLR2 agonist or a TLR9 agonist using the 3 method, in Example 10 of the present invention.

FIG. 46 graphically illustrates proportions of M-MDSCs and dendritic cells, obtained after treatment of bone marrow cells with TNF-α, IL-6, PGE2, IFN-α, or IFN-β, in place of a TLR agonist, using the 3 method, in Example 11 of the present invention.

FIG. 47 graphically illustrates proportions of CD11c$^-$CD11b$^+$Ly6G$^-$Ly6C$^+$PDCA-1$^+$ and CD11c$^-$CD11b$^+$Ly6G$^-$Ly6C$^+$PDCA-1$^-$ for respective treatment concentrations after treatment of bone marrow cells with TNF-α, IL-6, PGE2, IFN-α, or IFN-β, in place of a TLR agonist, using the 3 method, in Example 11 of the present invention.

FIG. 48 graphically illustrates changes in proportions of MDSCs and dendritic cells in the cells harvested after treatment of bone marrow cells with recombinant IL-6 protein or an IL-6 receptor blocker together with a TLR9 agonist using the 3 method, in Example 12 of the present invention.

FIG. 49 graphically illustrates a proportion of CD11c$^+$ cells induced in a case where M-MDSCs, which have been induced after treatment of bone marrow cells with recombinant IL-6 protein or an IL-6 receptor blocker together with a TLR9 agonist using the 3 method, are subjected to treatment with GM-CSF, in Example 12 of the present invention.

FIG. 50 graphically illustrates proportions of CD11c$^+$ cells for respective treatments in a case where Ly6C$^+$ M-MDSCs, which have been induced by treatment of bone marrow cells with a TLR2 agonist, a TLR9 agonist, or IFN-β using the 3 method, are subjected to treatment with GM-CSF, in Example 13 of the present invention.

Figure 27:
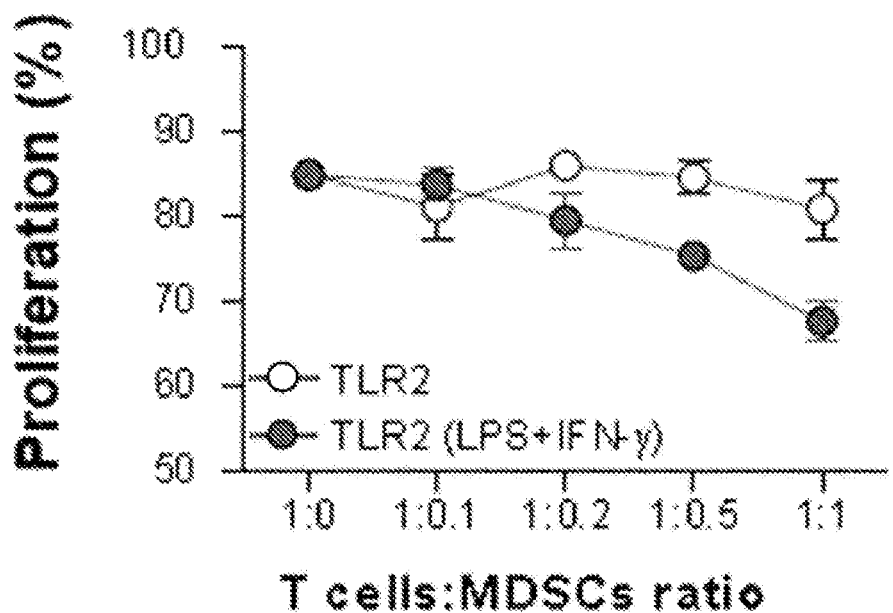
FIG. 27 graphically illustrates results obtained by subjecting M-MDSCs, which have been induced after treatment of bone marrow cells with a TLR2 agonist using the 3 method, to treatment with a co-culture of OVA-pulsed DCs and CD4 T cells, and then measuring changes in T cell proliferation capacity, in Example 7 of the present invention.

FIG. 51 graphically illustrates proportions of CD11c+ cells for respective treatments in a case where Ly6C+ M-MDSCs, which have been induced by treatment of bone marrow cells with a TLR2 agonist and further with IFN-β at 5 ng/ml or 25 ng/ml using the 3 method, are subjected to treatment with GM-CSF, in Example 13 of the present invention.

FIG. 52 graphically illustrates proportions of PDCA-1+ M-MDSCs and dendritic cells after treatment of bone marrow cells, which have been harvested from wild-type mice and type I IFN receptor knockout mice, with a TLR9 agonist using the 3 method, in Example 13 of the present invention.

DETAILED DESCRIPTION OF INVENTION

According to an embodiment of the present invention, there is provided a method for producing myeloid-derived suppressor cells (MDSCs), comprising a step of treating bone marrow cells with a toll-like receptor agonist (TLR agonist), to induce differentiation into myeloid-derived suppressor cells. Here, the toll-like receptor agonist used to treat the bone marrow cells is an agonist of a toll-like receptor (exogenous toll-like receptor) present in the plasma membrane and is preferably at least one of toll-like receptor 2 agonist or toll-like receptor 4 agonist for inducing differentiation into stable tolerogenic myeloid-derived suppressor cells having desired properties in the present invention. Further, in the present invention, in a case where the bone marrow cells are treated with an agonist of a toll-like receptor (intracellular toll-like receptor) present inside the cell, in particular, in the endolysosomal compartment, for example, with at least one of toll-like receptor 7 agonist or toll-like receptor 9 agonist, combined treatment with interleukin 6 may induce differentiation into stable tolerogenic myeloid-derived suppressor cells as desired in the present invention.

According to another embodiment of the present invention, there is provided a method for producing myeloid-derived suppressor cells (MDSCs), comprising a step of treating bone marrow cells with type I interferon, to induce differentiation into myeloid-derived suppressor cells. Here, the type I interferon used to treat the bone marrow cells may be at least one selected from the group consisting of IFN-α, IFN-β, IFN-κ, and IFN-ω, may preferably be at least one of IFN-α or IFN-β, and may more preferably be IFN-β.

According to yet another embodiment of the present invention, there is provided a method for producing dendritic cells, comprising steps of: (1) treating bone marrow cells with a toll-like receptor agonist (TLR agonist), to induce differentiation into myeloid-derived suppressor cells (MDSCs); and (2) treating the differentiation-induced myeloid-derived suppressor cells with a growth factor, to induce differentiation into dendritic cells. Here, the toll-like receptor agonist used to treat the bone marrow cells is preferably an agonist of an intracellular toll-like receptor; and is more preferably at least one of toll-like receptor 7 agonist or toll-like receptor 9 agonist, among the agonists of intracellular toll-like receptors, for inducing differentiation into dendritic cells having desired properties in the present invention.

Hereinafter, the present invention will be described in more detail by way of examples. These examples are merely given to illustrate the present invention in more detail, and it will be apparent to those skilled in the art that according to the gist of the present invention, the scope of the present invention is not limited by these examples.

EXAMPLES

[Example 1] Treatment of Bone Marrow Cells with Toll-Like Receptor Agonist

Whole bone marrow cells in the femurs were harvested from C57BL/6 mice using a bone marrow harvesting needle. The harvested bone marrow cells were washed with PBS and red blood cells (RBCs) were removed using a red blood cell lysis buffer (Sigma Aldrich). The bone marrow cells were dispensed in a 6-well plate ($1\times10^6$ cells/ml; 2 ml/well) and cultured, under a condition of 5% $CO_2$ and 37° C., in complete RPMI 1640 (c-RPMI 1640) medium supplemented with 100 U/mL of penicillin/streptomycin (Lonza, Basel, Switzerland), 10% fetal bovine serum (Lonza), 50 μM mercaptoethanol (Lonza), 0.1 mM non-essential amino acids (Lonza), and GM-CSF (20 ng/mL). Here, as illustrated in FIG. 1, each of a TLR2 agonist (Pam3CSK4), a TLR3 agonist (poly I:C), a TLR4 agonist (LPS, from *Escherichia coli* O111:B4), a TLR7 agonist (imiquimod, R837), and a TLR9 agonist (ODN1826) was added to the medium in an amount of 50 ng/ml at the initiation time of differentiation (1 method), on day 3 after the initiation of differentiation (2 method), or at the initiation time of differentiation and on day 3 after the initiation of differentiation (3 method). On day 3 of culture, the bone marrow cells and 1 ml of c-RPMI 1640 medium were added to each well. On day 6 of culture, the cells were collected and stained with Fluorescein-conjugated CD11c mAb to measure a proportion of CD11c+ cells. The results are illustrated in FIGS. 2 and 3. As a result, in a case where the TLR2 agonist, TLR4 agonist, TLR7 agonist, or TLR9 agonist is applied using the 3 method, capacity of inhibiting dendritic cells was strongly induced. In addition, in a case where the 3 method is used, proportions of CD11c+ cells were checked for respective treatment concentrations of each TLR agonist (TLR2 agonist (Pam3)—1, 10, and 50 ng/ml; TLR3 agonist (Poly I:C)—10, 100, and 500 ng/ml; TLR4 agonist (LPS)—1, 10, and 50 ng/ml; TLR7 agonist (imiquimod)—1, 10, and 50 ng/ml; TLR9 agonist (CPG:ODN)—1, 10, and 50 ng/ml). As a result, as illustrated in FIG. 4, it was found that differentiation into dendritic cells is inhibited in a concentration-dependent manner by the TLR agonist treated. However, in a case where the TLR3 agonist is applied, an effect of inhibiting differentiation into dendritic cells was not observed.

[Example 2] Identification of Relationship Between Inhibition of Differentiation into Dendritic Cells and MyD88

Additionally, in order to identify whether an effect of inhibiting differentiation into dendritic cells is induced in a MyD88-dependent manner, C57BL/6 mice and C57BL/6 MyD88−/− mice were treated with a TLR agonist in the same manner as the 3 method in Example 1, to induce differentiation, and then a proportion of CD11c+MHC-II+ cells was measured. The results are illustrated in FIGS. 5 and 6.

As illustrated in FIGS. 5 and 6, except a case where a TLR3 agonist is applied, in a case where a TLR2 agonist, a TLR4 agonist, a TLR7 agonist, or a TLR9 agonist is applied, a proportion of CD11c+MHC-II+ cells was decreased. However, in a case where MyD88 is knocked out, a proportion of CD11c⁺MHC-II⁺ cells was maintained at 80% or higher, indicating that differentiation into dendritic cells is induced.

From these results, it was found that differentiation into dendritic cells is induced in a MyD88-dependent manner.

[Example 3] Phenotypic Analysis of Cells Induced by TLR Stimulation

The results obtained by analyzing phenotypes of cells harvested after treating bone marrow cells with a TLR agonist in the same manner as the 3 method in Example 1 and performing culture for 6 days are illustrated in FIGS. 7 and 8. As a result, it was found that in the cells induced by TLR stimulation, all dendritic cell phenotypes (CD11c, CD4, CD103, CD8a) decrease, whereas expression of Gr-1, Ly6C, and CD11b is induced at a high level. From these expression patterns, it was predictable that the cells induced by differentiation from the bone marrow cells are myeloid-derived suppressor cells (MDSCs).

Here, it was found that in a case where among TLR agonists, especially a TLR7 or TLR9 agonist is applied, PDCA-1, a marker of plasmacytoid dendritic cells (pDCs) is highly induced; however, from the viewpoint that B220, another marker of pDCs, shows no significant difference, it can be seen that pDCs are not induced.

From these results, it can be seen that different types of MDSCs are induced in a case of being treated with a TLR2 or TLR4 agonist, and in a case of being treated with a TLR7 or TLR9 agonist.

[Example 4] Identification of Phenotypes of MDSCs Induced by TLR Stimulation

As illustrated in Example 3, it can be seen that the cells, which have been induced by differentiation from bone marrow cells after TLR stimulation according to the 3 method in Example 1, are MDSCs. On the other hand, subtypes of the MDSCs may be divided into monocytic-MDSCs (M-MDSCs) and granulocytic-MDSCs (G-MDSCs). Gr-1$^{high}$ cells mostly correspond to G-MDSCs, and Gr-1$^{low}$ cells may be classified as M-MDSCs.

Thus, for MDSCs harvested after performing culture for 6 days with a Gr-1 antibody using the 3 method in Example 1, an expression level of Gr-1 was checked. The results are illustrated in FIGS. 9 and 10. As a result, in the cells induced by a TLR2 or TLR4 agonist, Gr-1$^{low}$ MDSCs were induced at a high level; on the contrary, in the cells induced by a TLR7 or TLR9 agonist, Gr-1$^{high}$ MDSCs were induced at a high level.

Furthermore, in order to accurately classify subtypes of MDSCs, their expression patterns were identified using Ly6G and Ly6C antibodies. As a result, as illustrated in FIGS. 11 and 12, it was found that G-MDSCs ($X_2$ cells) and M-MDSCs ($X_3$ cells and $X_4$ cells) are induced from bone marrow cells by TLR stimulation, and among these, a proportion of M-MDSCs is high; however, it was found that Ly6C$^{int}$ M-MDSCs ($X_3$ cells) are induced in a case of being treated with a TLR2 or TLR4 agonist, and that Ly6C$^{high}$ M-MDSCs ($X_4$ cells) are induced in a case of being treated with a TLR7 or TLR9 agonist.

[Example 5] Identification of Relationship Between Differentiation into MDSCs and MyD88

In order to identify whether differentiation into respective MDSCs' subtypes is induced in a MyD88-dependent manner, C57BL/6 mice and C57BL/6 MyD88$^{-/-}$ mice were treated in the same manner as the 3 method in Example 1, and then expression patterns of Ly6G and Ly6C were identified in the same manner as in Example 4 (FIG. 13). As a result, it can be seen that Ly6C$^{int}$ M-MDSCs ($X_3$ cells) are induced in a case of being treated with a TLR2 or TLR4 agonist, and that Ly6C$^{high}$ M-MDSCs ($X_4$ cells) are induced in a case of being treated with a TLR7 or TLR9 agonist, indicating that differentiation into MDSCs is MyD88-dependent.

[Example 6] Molecular Parameters Induced by TLR2 or TLR9 Agonist

As shown in Example 4, various factors induced in M-MDSCs were analyzed to accurately determine whether the cells induced by differentiation from bone marrow cells after TLR stimulation using the 3 method are M-MDSCs. In addition, in this analysis, in order to identify functional differences between Ly6C$^{int}$ M-MDSCs induced by a TLR2 or TLR4 agonist, and Ly6C$^{high}$ M-MDSCs induced by a TLR7 or TLR9 agonist, TLR2-M-MDSCs and TLR9-M-MDSCs were separated using a MACS system. Here, treatment with LPS and IFN-γ was performed for 24 hours to induce activity of M-MDSCs.

Specifically, a NO$_2$ formation level was analyzed using a NO kit, expression levels of NOS2 and arginase-1 were analyzed through Western blotting, and an expression level of IL-10 was analyzed through ELISA. The results are illustrated in FIGS. 14, 15, and 16, respectively. In addition, expression levels of arginase-1 and iNOS were identified with FACS. The results are illustrated in FIGS. 17 and 18. As illustrated in FIGS. 14 to 18, it was found that expression of anti-inflammatory cytokine (IL-10) and immunosuppressive agents (Arg-1, NOS) is increased upon stimulation of M-MDSCs induced by treatment with a TLR2 or TLR9 agonist.

In addition, expression levels of various markers including CD124, CD115, F4/80, and PDCA-1 were analyzed to identify phenotypes of M-MDSCs induced in a case of being treated with a TLR2 or TLR9 agonist. As a result, as illustrated in FIGS. 19 and 20, CD124 was expressed at a high level in M-MDSCs induced after TLR2 stimulation, and CD115, F4/60, and PDCA-1 were expressed at a low level in M-MDSCs induced after TLR2 stimulation.

Additionally, for M-MDSCs induced in a case of being treated with a TLR2 or TLR9 agonist, expression levels of inflammatory cytokines were analyzed with ELISA, and the results are illustrated in FIG. 21. Expression levels of immunosuppressive factors were identified with FACS, and the results are illustrated in FIGS. 22 to 24. As a result, it was found that in a case of being activated, M-MDSCs induced after treatment with the TLR2 agonist inhibit expression of inflammatory cytokines at a higher level than M-MDSCs induced after treatment with the TLR9 agonist.

Figure 28:
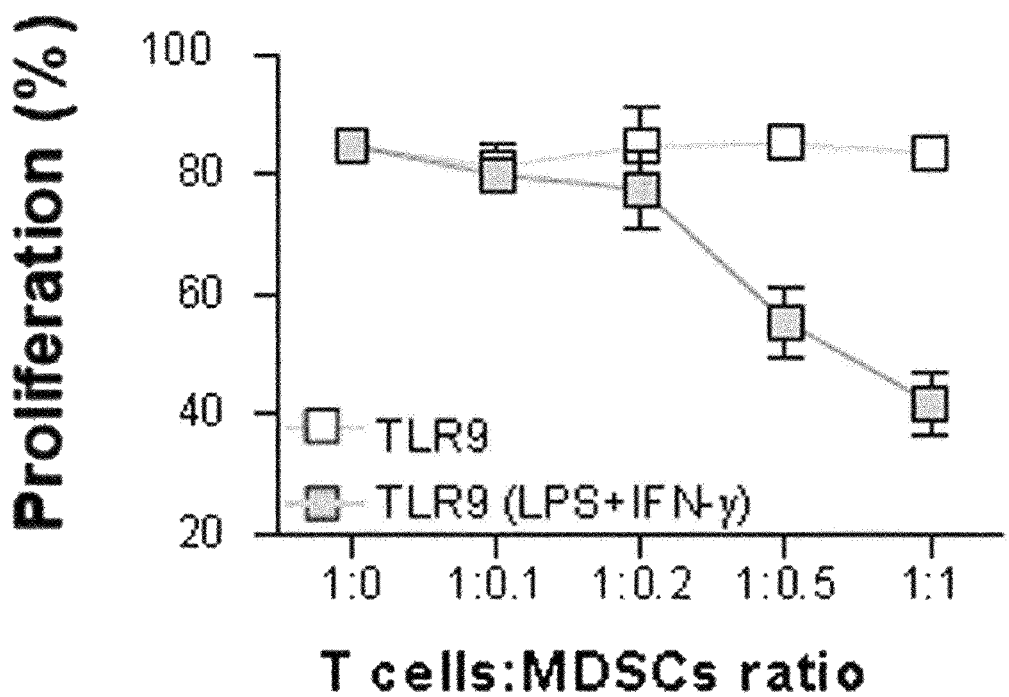
FIG. 28 graphically illustrates results obtained by subjecting M-MDSCs, which have been induced after treatment of bone marrow cells with a TLR9 agonist using the 3 method, to treatment with a co-culture of OVA-pulsed DCs and CD4 T cells, and then measuring changes in T cell proliferation capacity, in Example 7 of the present invention.

[Example 7] Identification of T Cell Proliferation Inhibition and Induction of Differentiation into Regulatory T Cells by M-MDSCs Induced by TLR2 or TLR9 Agonist Hereinafter, T-cell proliferation inhibition capacity and induction of differentiation into regulatory T cells, which are other characteristics of M-MDSCs, were identified. More specifically, T cells were activated through co-culture of OVA-pulsed DCs and CellTrace-labeled CD4 T cells of OT-II mice, and M-MDSCs which had been induced by differentiation using the 3 method in Example 1 were added thereto. Then, T cell inhibition capacity of M-MDSCs was identified, and the results are illustrated in FIGS. 25 to 28. An expression level of Foxp3 was checked to identify a proportion of regulatory T cells, and the results are illustrated in FIGS. 29 to 32.

As illustrated in FIGS. 25 to 32, it was found that both M-MDSCs induced after TLR2 stimulation and M-MDSCs induced after TLR9 stimulation inhibit proliferation of T cells in a number-dependent manner and remarkably induce differentiation into Foxp3$^+$CD4 T cells.

[Example 8] Evaluation of Differences, in Terms of Secondary Differentiation, Between M-MDSCs Induced by TLR2 Agonist and M-MDSCs Induced by TLR9 Agonist Respective M-MDSCs which had been induced by differentiation using the 3 method in Example 1 were dispensed in 6-well plates ($1 \times 10^6$ cells/ml; 2 ml/well), and then cultured for 5 days in cRPMI 1640 supplemented with 10% fetal bovine serum, 100 U/ml penicillin/streptomycin, 50 µM mercaptoethanol, 0.1 mM non-essential amino acids, and 20 ng/ml GM-CSF or M-CSF. The resulting cells were harvested. In order to identify whether differentiation into dendritic cells has been induced by the culture, staining with anti-CD11c and anti-MHC-II was performed for dendritic cells, and then analysis was performed through the flow cytometer FACSverse. The results are illustrated in FIGS. 33 and 34. In addition, in order to identify whether differentiation into macrophages has been induced by the culture, staining with anti-CD11b and anti-F40/80 was performed for macrophages, and then analysis was performed through the flow cytometer FACSverse. The results are illustrated in FIGS. 35 and 36.

As illustrated in FIGS. 33 to 36, it was found that M-MDSCs induced by a TLR2 agonist have been partially induced to differentiate into macrophages and have hardly differentiated into dendritic cells, whereas M-MDSCs induced by a TLR9 agonist have been induced to differentiate into dendritic cells and macrophages.

Additionally, T cell proliferation inhibition capacity and degree of secondary differentiation into dendritic cells were evaluated while culturing respective M-MDSCs, which had been induced by differentiation using the 3 method in Example 1, with addition of GM-CSF in the presence of T cells. As a result, as illustrated in FIGS. 37 and 38, it was found that M-MDSCs induced by TLR2 stimulation do not show such changes and show consistently T cell proliferation inhibition capacity and IFN-γ inhibition capacity, whereas M-MDSCs induced by TLR9 stimulation show remarkably decreased T cell proliferation inhibition capacity and IFN-γ inhibition capacity in the presence of GM-CSF.

In addition, degree of secondary differentiation into CD11c was identified under these conditions. As a result, as illustrated in FIG. 39, it was found that M-MDSCs induced by TLR2 stimulation stably maintain cellular characteristics, whereas M-MDSCs induced by TLR9 stimulation have been induced to differentiate into dendritic cells.

From these results, it can be seen that M-MDSCs induced by differentiation using a TLR2 agonist have not been induced to differentiate into dendritic cells and stably maintain characteristics of M-MDSCs even in a case of being treated with a growth factor, whereas M-MDSCs induced by differentiation using a TLR9 agonist have been secondarily induced to differentiate into dendritic cells in a case of being further treated with a growth factor.

[Example 9] Functional Analysis for Dendritic Cells and Macrophages which had been Secondarily Differentiated from M-MDSCs Induced by TLR9 Agonist Hereinafter, characteristics of the dendritic cells, which had been secondarily differentiated from M-MDSCs induced by differentiation using the TLR9 agonist in the present invention, were analyzed by comparison with those of dendritic cells obtained by differentiation using other methods.

In vitro methods of inducing differentiation into dendritic cells include a method of inducing differentiation using bone marrow cells and a method of inducing differentiation via Ly6C$^+$ cells. Here, using the method of inducing differentiation using bone marrow cells, cells isolated from the mouse femoral bone marrow were cultured for 5 days in the same manner as the method of inducing differentiation into dendritic cells in Example 8 (bone marrow-derived dendritic cells, BMDCs). In addition, Ly6C$^+$ cells were isolated from the mouse femoral bone marrow through Ly6C MicroBeads and then cultured as described above (Ly6C$^+$-derived DCs). After 5 days, these cells were subjected to CD11c MicroBeads, to reisolate only dendritic cells (>90%).

The dendritic cells isolated by the above methods and the dendritic cells obtained by secondary differentiation in Example 8 were analyzed in terms of phenotypes, and the results are illustrated in FIGS. 40 and 41.

In addition, the respective three dendritic cells were dispensed in cRPMI 1640 medium in 48-well plates ($1 \times 10^5$ cells/ml), and then treated with LPS and IFN-γ as stimulants for the dendritic cells. Expression levels of cytokines induced by the respective dendritic cells were analyzed with ELISA, and their NO$_2$ formation levels were analyzed with a NO kit. The results are illustrated in FIGS. 42 and 43. As a result, it was found that the dendritic cells, which have been secondarily differentiated from M-MDSCs induced by differentiation using a TLR9 agonist induce IL-12p70 and IL-10, which are important for differentiation into Th1- and Th2-type cells, at higher levels than the dendritic cells induced by other methods.

Additionally, in order to identify an effect of the dendritic cells according to the present invention on T cells, the three dendritic cells as obtained above were stimulated with OVA323-339 peptide for 1 hour and then co-cultured, at a ratio of 1:5 (DCs: T cells), with CD4 T cells isolated from OT-II mice for 3 days. Subsequently, T cell proliferation capacity and IFN-γ expression levels were analyzed. As illustrated in FIG. 44, it was found that the dendritic cells, which have been secondarily differentiated from M-MDSCs induced by differentiation using the TLR9 agonist, exhibit remarkably superior T cell proliferation capacity as compared with Ly6C$^+$-derived dendritic cells; and it was found that the dendritic cells, which have been secondarily differentiated from M-MDSCs induced by differentiation using the TLR9 agonist, allow Th1 cell-induced IFN-γ to be induced at a very high level as compared with the dendritic cells obtained by differentiation using other methods.

From these results, it can be seen that the dendritic cells, which have been secondarily differentiated from M-MDSCs induced by differentiation using the TLR9 agonist, can effectively induce naive T cells into Th1 cells.

[Example 10] Effect of Cytokine on M-MDSCs
Induced by TLR2 or TLR9

Hereinafter, experiments were conducted assuming that for respective M-MDSCs induced by differentiation upon treatment with a TLR2 or TLR9 agonist, differences in phenotype, T cell inhibition capacity, regulatory T cell formation capacity, and differentiation into dendritic cells are due to different cytokine secretion induced by each TLR stimulation. Therefore, cytokines induced at early differentiation stages (8, 18, and 36 hours after stimulation with TLR agonist) after treatment of bone marrow cells with a TLR2 or TLR9 agonist were analyzed. As a result, as illustrated in FIG. 45, it was found that TNF-α, IL-6, and PGE2 are induced in a case of being treated with the TLR2 agonist, and TNF-α, IL-6, IFN-α, and IFN-β are induced in a case of being treated with the TLR9 agonist; and in particular, it was found that IL-6 is remarkably induced in a case of being treated with the TLR2 agonist as compared with a case of being treated with the TLR9 agonist. Here, although not shown by data, it was found that IFN-γ, IL-15, IL-1β, TGF-β, IL-4, IL-12p70, IL-10, and FLT2L are not induced upon TLR2 or TLR9 stimulation.

[Example 11] Analysis of Association of Cytokines with Differentiation into M-MDSCs In order to identify association of TLR stimulation-induced cytokines with formation of M-MDSCs and inhibition of secondary differentiation as identified in Example 10, the 3 method in Example 1 was performed, except that TNF-α, IL-6, PGE2, IFN-α, or IFN-β is applied in place of the TLR agonist. On day 6 of culture, it was identified whether M-MDSCs and dendritic cells are formed. As illustrated in FIG. 46, it was found that in a concentration-dependent manner, M-MDSCs are formed and differentiation into dendritic cells is inhibited in a case of being treated with IL-6, PGE2, IFN-α, or IFN-β.

Additionally, in order to identify whether formation of PDCA-1$^+$ M-MDSCs, which had been induced in a case of being treated with a TLR9 agonist, was caused by such a cytokine, distribution of CD11c$^-$CD11b$^+$Ly6G$^-$Ly6C$^+$PDCA-1$^+$ and CD11c$^-$CD11b$^+$Ly6G$^-$Ly6C$^+$PDCA-1$^-$ was checked for the cells obtained on day 6 of culture as described above. As a result, as illustrated in FIG. 47, it was found that M-MDSCs having the phenotype CD11c$^-$CD11b$^+$Ly6G$^-$ Ly6C$^+$PDCA-1$^-$ are induced in large quantities, in particular, upon stimulation with IL-6.

[Example 12] Evaluation of M-MDSC Induction Capacity Caused by TLR9 and IL-6

In order to evaluate differentiation into M-MDSCs caused by IL-6 and functions of the M-MDSCs, recombinant IL-6 or an IL-6 receptor blocker was applied together with a TLR9 agonist using the 3 method in Example 1, and then the cells were harvested on day 6 of culture. Among the cells harvested according to the respective treatments, proportions of MDSCs and dendritic cells were checked. As a result, as illustrated in FIG. 48, it was found that in a case of being treated with IL-6, differentiation into PDCA-1$^+$ M-MDSCs is increased and differentiation into dendritic cells is further decreased; and it was found that in a case of being treated with an IL-6 receptor blocker, differentiation into dendritic cells is increased and differentiation into PDCA-1$^+$ M-MDSCs is decreased.

In order to identify whether the M-MDSCs induced according to respective treatments as described above are secondarily differentiated into dendritic cells, culture was performed for 5 days in the same manner as the method of inducing differentiation into dendritic cells in Example 8. As a result, as illustrated in FIG. 49, it was found that degree of differentiation of M-MDSCs into dendritic cells is remarkably decreased and thus M-MDSCs are maintained in a case of being further treated with IL-6, as compared with a case of being treated with only TLR9 agonist, and that the degree of differentiation is increased in a case of being treated with an IL-6 receptor blocker.

From there results, it can be seen that in a case where bone marrow cells are treated with an agonist of an intracellular toll-like receptor such as a TLR9 agonist, combined treatment with IL-6 makes it possible to obtain stable tolerogenic myeloid-derived suppressor cells that are not induced to differentiate into dendritic cells.

[Example 13] Evaluation of M-MDSCs' Capacity to Differentiate into Dendritic Cells, Induced by Type I IFN The 3 method in Example 1 was performed, except that a TLR2 agonist, a TLR9 agonist, or IFN-β is applied, and then only Ly6C$^+$ M-MDSCs are collected on day 6 of culture. Then, GM-CSF was applied in the same manner as in Example 8 and culture was performed for 3 days. Subsequently, proportions of CD11c$^+$ cells were checked for the respective treatments. As a result, as illustrated in FIG. 50, it was found that in a case of being treated with IFN-β which is type I IFN, differentiation into dendritic cells is induced similarly to a case of being treated with a TLR9 agonist.

Additionally, a TLR2 agonist was applied using the 3 method in Example 1, with IFN-β being further applied in an amount of 5 ng/ml or 25 ng/ml. Then, on day 6 of culture, only Ly6C$^+$ M-MDSCs were collected. Subsequently, GM-CSF was applied in the same manner as in Example 8 and culture was performed for 3 days. Then, proportions of CD11c$^+$ cells were checked for the respective treatments. As a result, as illustrated in FIG. 51, it was found that differentiation into dendritic cells is hardly induced in a case of being treated with the TLR2 agonist, whereas differentiation into dendritic cells is increased in a concentration-dependent manner in a case where the TLR2 agonist is applied in combination with IFN-β which is type I IFN.

Finally, in order to accurately check the function of type I IFN, bone marrow cells harvested from wild-type mice and type I IFN receptor knockout mice were treated with a TLR9 agonist using the 3 method in Example 1; and on day 6 of culture, degree of formation of PDCA-1$^+$ M-MDSCs and dendritic cells was evaluated. As a result, as illustrated in FIG. 52, it was found that MDSCs themselves are not induced from type I IFN receptor knockout mice.

From these results, it can be seen that in the present invention, the type I IFN receptor plays an important role in inducing differentiation of bone marrow cells into PDCA-1$^+$ M-MDSCs and inducing differentiation of the PDCA-1$^+$ M-MDSCs into immunogenic dendritic cells.

As stated above, specific parts of the present invention have been described in detail. However, it is apparent to those skilled in the art that such specific description is only for illustrating preferred embodiments, and the scope of the present invention is not limited thereto. Accordingly, the substantial scope of the present invention will be defined by the appended claims and equivalents thereof.

INDUSTRIAL APPLICABILITY

According to an embodiment of the present invention, there are provided a method for producing myeloid-derived suppressor cells, a myeloid-derived suppressor cell produced thereby, and uses thereof.

According to another embodiment of the present invention, there are provided a method for producing dendritic cells, a dendritic cell produced thereby, and uses thereof.

The invention claimed is:

1. A method for producing myeloid-derived suppressor cells (MDSCs), comprising: a step of treating bone marrow cells with a toll-like receptor agonist (TLR agonist) or type I interferon, to induce differentiation into myeloid-derived suppressor cells,
    wherein the toll-like receptor agonist is at least one of toll-like receptor 7 agonist and toll-like receptor 9 agonist,
    wherein the myeloid-derived suppressor cells comprise MDSCs having phenotype PDCA-1+, and
    wherein the toll-like receptor agonist or the type I interferon is applied at the initiation time of bone marrow cell differentiation, and then is applied one or more times within 3 days after the initiation of differentiation.

2. The method according to claim 1, wherein the toll-like receptor agonist is an agonist of an intracellular toll-like receptor.

3. The method according to claim 1, wherein the bone marrow cells are further treated with interleukin 6 together with the toll-like receptor agonist.

4. The method according to claim 3, wherein the interleukin 6 is applied in an amount of 1 to 100 ng/ml.

5. The method according to claim 1, wherein the toll-like receptor agonist or the type I interferon is applied one or more times before initiation of, at the initiation time of, or during bone marrow cell differentiation.

6. The method according to claim 5, wherein the bone marrow cell differentiation is carried out by inoculating the bone marrow cells in a medium supplemented with a growth factor and performing culture for 5 to 10 days.

7. The method according to claim 6, wherein the growth factor is at least one selected from the group consisting of granulocyte-macrophage colony stimulating factor (GM-CSF), granulocyte colony stimulating factor (G-CSF), macrophage colony stimulating factor (M-CSF), stem cell factor (SCF), and interleukin 3 (IL-3).

8. The method according to claim 6, wherein the growth factor is added in an amount of 10 ng/ml to 500 ng/ml.

9. The method according to claim 1, wherein the toll-like receptor agonist or the type I interferon is applied in an amount of 10 ng/ml to 1,000 ng/ml.

10. The method according to claim 1, wherein the step to induce differentiation into myeloid-derived suppressor cells is performed by culturing the bone marrow cells in a medium supplemented with a growth factor and at least one of the toll-like receptor agonist or the type I interferon.

11. The method according to claim 1, wherein the myeloid-derived suppressor cells are monocytic myeloid-derived suppressor cells (M-MDSCs).

12. The method of claim 1, wherein the type I interferon is at least one selected from the group consisting of IFN-α, IFN-β, IFN-κ, and IFN-ω.

13. A method for preventing or treating an immune disease, the method comprising treating bone marrow cells with a toll-like receptor agonist (TLR agonist) or type 1 interferon to induce differentiation into myeloid-derived suppressor cells, and administering the myeloid-derived suppressor cells to a subject in need thereof,
    wherein the toll-like receptor agonist is at least one of toll-like receptor 7 agonist and toll-like receptor 9 agonist, and
    wherein the myeloid-derived suppressor cells comprise MDSCs having phenotype PDCA-1+.

14. The method according to claim 13, wherein the immune disease is graft rejection after organ transplantation, graft rejection after hematopoietic stem cell transplantation, an autoimmune disease, or an allergic disease.

15. The method according to claim 13, wherein the bone marrow cells are further treated with interleukin 6 together with the toll-like receptor agonist.

* * * * *